United States Patent
Nicholas et al.

(10) Patent No.: US 12,054,718 B2
(45) Date of Patent: Aug. 6, 2024

(54) RNAi AGENTS FOR INHIBITING EXPRESSION OF PNPLA3, PHARMACEUTICAL COMPOSITIONS THEREOF, AND METHODS OF USE

(71) Applicant: Arrowhead Pharmaceuticals, Inc., Madison, WI (US)

(72) Inventors: Anthony Nicholas, Oregon, WI (US); Tao Pei, Middleton, WI (US); Zhao Xu, Brookfield, WI (US); Casi Schienebeck, Deerfield, WI (US); Zhi-Ming Ding, Waunakee, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 73 days.

(21) Appl. No.: 17/213,787

(22) Filed: Mar. 26, 2021

(65) Prior Publication Data
US 2021/0301294 A1    Sep. 30, 2021

Related U.S. Application Data

(60) Provisional application No. 63/000,137, filed on Mar. 26, 2020.

(51) Int. Cl.
*C12N 15/113*    (2010.01)
*A61K 47/54*    (2017.01)
*A61P 1/16*    (2006.01)

(52) U.S. Cl.
CPC ........ *C12N 15/1137* (2013.01); *A61K 47/549* (2017.08); *A61P 1/16* (2018.01);
(Continued)

(58) Field of Classification Search
CPC ............ C12N 15/1137; C12N 2310/14; C12N 2310/315; C12N 2310/321;
(Continued)

(56) References Cited

U.S. PATENT DOCUMENTS 4,522,811 A    6/1985    Eppstein et al.
5,885,968 A    3/1999    Biessen et al.
(Continued)

FOREIGN PATENT DOCUMENTS

WO    2000/053722 A2    9/2000
WO    2008/022309 A2    2/2008
(Continued)

OTHER PUBLICATIONS

Watts et al. 2009. Studies on the hydrolytic stability of 2'-fluoroarabinonucleic acid (2'F-ANA). Organic & Biomolecular Chemistry 7: 1904-1910. DOI: 10.1039/b900443b (Year: 2009).*
(Continued)

*Primary Examiner* — Kimberly Chong
*Assistant Examiner* — Ruth Sophia Arieti
(74) *Attorney, Agent, or Firm* — BakerHostetler

(57) ABSTRACT

Described are RNAi agents, e.g., double stranded RNAi agents, for inhibiting patatin-like phospholipase domain-containing protein 3 (PNPLA3) gene expression. Also disclosed are pharmaceutical compositions that include PNPLA3 RNAi agents and methods of use thereof. The PNPLA3 RNAi agents disclosed herein may be conjugated to targeting ligands to facilitate the delivery to cells, including to hepatocytes. Delivery of the PNPLA3 RNAi agents in vivo provides for inhibition of PNPLA3 gene expression. The RNAi agents can be used in methods of treatment of PNPLA3-related diseases and disorders, including non-alcoholic fatty liver disease (NAFLD), nonalcoholic steatohepatitis (NASH), hepatic fibrosis, and alcoholic or non-alcoholic liver diseases, including cirrhosis.

34 Claims, 2 Drawing Sheets
Specification includes a Sequence Listing.

(52) U.S. Cl.
CPC .... *C12N 2310/14* (2013.01); *C12N 2310/315* (2013.01); *C12N 2310/321* (2013.01); *C12N 2310/322* (2013.01); *C12N 2310/346* (2013.01); *C12N 2310/351* (2013.01); *C12N 2320/35* (2013.01)

(58) Field of Classification Search
CPC ........ C12N 2310/322; C12N 2310/346; C12N 2310/351; C12N 2320/35; C12N 2310/317; C12N 2310/331; C12N 2310/333; C12N 2310/335; C12N 2310/3533; C12N 2310/3535; C12N 2310/3521; C12N 2310/32; A61K 47/549; A61K 45/06; A61K 31/713; A61P 1/16; C12Y 301/01003; C12Y 301/01004
See application file for complete search history.

(56) References Cited

U.S. PATENT DOCUMENTS

| | | | |
|---|---|---|---|
| 5,998,203 | A | 12/1999 | Matulic-Adamic et al. |
| 10,231,988 | B2* | 3/2019 | Fitzgerald ............... C12P 19/34 |
| 11,149,276 | B2* | 10/2021 | Tremblay ............... A61K 47/02 |
| 2017/0349903 | A1 | 12/2017 | Liu et al. |
| 2018/0064819 | A1* | 3/2018 | Li ........................... C07H 5/06 |

FOREIGN PATENT DOCUMENTS

| | | |
|---|---|---|
| WO | 2011/104169 A1 | 9/2011 |
| WO | 2012/083185 A2 | 6/2012 |
| WO | 2013/032829 A1 | 3/2013 |
| WO | 2013/158141 A1 | 10/2013 |
| WO | 2016/130806 A2 | 8/2016 |
| WO | 2017/156012 A1 | 9/2017 |
| WO | 2018/044350 A1 | 3/2018 |
| WO | 2019/118638 A2 | 6/2019 |

OTHER PUBLICATIONS

NCBI. Novel Human Gene Mapping to Chromosome 22. https://www.ncbi.nlm.nih.gov/nuccore/17059635. Accessed May 4, 2023. (Year: 2008).*

ClinVar. 2019. ClinVar Exon 9 Pathogenic SNPs. From https://www.ncbi.nlm.nih.gov/ClinVar. Search term: PNPLA3[GENE]. Accessed May 4, 2023 (Year: 2019).*

Landrum et al. 2019. ClinVar: improvements to accessing data. Nuc. Ac. Res. 48:D835-D844. (Year: 2019).*

Rady et al. 2012. PNPLA3 downregulation exacerbates the fibrotic response in human hepatic stellate cells. PloS ONE 16[12]: e0260721 (Year: 2012).*

Huang et al. 2015. Association of diabetes and PNPLA3 genetic variants with disease severity of patients with chronic hepatitis C virus infection. J. Hepatol. 62:512-518 (Year: 2015).*

Trepo et al. 2016. PNPLA3 gene in liver diseases. J. Hepatol. 65:399-412 (Year: 2016).*

Grgurevic et al. 2021. Hepatocellular carcinoma in NAFLD: from epidemiology to diagnostic approach. Cancers 13[22]:5844 (Year: 2021).*

Basuray, S., et al., "Accumulation of PNPLA3 on lipid droplets is the basis of associated hepatic steatosis," Proceedings of the National Academy of Sciences, vol. 116, No. 19, Apr. 24, 2019, pp. 9521-9526.

Qiao, A., et al., "Mouse patatin-like phospholipase domain-containing 3 influences systemic lipid and glucose homeostasis," Hepatology, vol. 54, No. 2, Jun. 20, 2011, pp. 509-521.

Biessen et al., "Synthesis of Cluster Galactosides with High Affinity for the Hepatic Asialoglycoprotein Receptor", J. Med. Chem., 1995, vol. 39, 1538-1546.

Connolly et al., "Binding and Endocytosis of Cluster Glycosides by Rabbit Hepatocytes Evidence for a short-circuit pathway that does not lead to degradation", J. Biol. Chem., 1982, 257, 939-945.

Czaudema et al., "Structural variations and stabilizing modi® cations of synthetic siRNAs in mammalian cells", Nucleic Acids Res., 2003, 31(11), 2705-2716.

Iobst et al., "Selective Sugar Binding to the Carbohydrate Recognition Domains of the Rat Hepatic and Macrophage Asialoglycoprotein Receptors", Journal Biological Chemistry, 1996, 271, 6686-6693.

Zhang et al., "High levels of foreign gene expression in hepatocytes after tail vein injection of naked plasmid DNA", Human Gene Therapy, 1999, vol. 10, p. 1735-1737.

Jackson et al., "Expression profiling reveals off-target gene regulation by RNAi", Nature Biotechnology, vol. 21, No. 6, Jun. 2003, 635-638.

Kamola et al., "The siRNA Non-seed Region and Its Target Sequences Are Auxiliary Determinants of Off-Target Effects", PLoS Comput Biol, Dec. 11, 2015, 1-17.

* cited by examiner

SEQUENCE LISTING

```
<160> NUMBER OF SEQ ID NOS: 258

<210> SEQ ID NO 1
<211> LENGTH: 2805
<212> TYPE: DNA
<213> ORGANISM: Homo sapiens

<400> SEQUENCE: 1
atggtccgag gggggcgggg ctgacgtcgc gctgggaatg ccctggccga gacactgagg      60
cagggtagag agcgcttgcg ggcgccgggc ggagctgctg cggatcagga cccgagccga     120
ttcccgatcc cgacccagat cctaacccgc gccccgccc cgccgccgcc gccatgtacg     180
acgcagagcg cggctggagc ttgtccttcg cgggctgcgg cttcctgggc ttctaccacg     240
tcggggcgac ccgctgcctg agcgagcacg ccccgcacct cctccgcgac gcgcgcatgt     300
tgttcggcgc ttcggccggg gcgttgcact gcgtcggcgt cctctccggt atcccgctgg     360
agcagactct gcaggtcctc tcagatcttg tgcggaaggc caggagtcgg aacattggca     420
tcttccatcc atccttcaac ttaagcaagt tcctccgaca gggtctctgc aaatgcctcc     480
cggccaatgt ccaccagctc atctccggca aaataggcat ctctcttacc agagtgtctg     540
atggggaaaa cgttctggtg tctgactttc ggtccaaaga cgaagtcgtg gatgccttgg     600
tatgttcctg cttcatcccc ttctacagtg gccttatccc tccttccttc agaggcgtgc     660
gatatgtgga tggaggagtg agtgacaacg tacccttcat tgatgccaaa caaccatca     720 ccgtgtcccc cttctatggg gagtacgaca tctgccctaa agtcaagtcc acgaactttc     780
ttcatgtgga catcaccaag ctcagtctac gcctctgcac agggaacctc taccttctct     840
cgagagcttt tgtcccccg gatctcaagg tgctgggaga gatatgcctt cgaggatatt     900
tggatgcatt caggttcttg gaagagaagg gcatctgcaa caggccccag ccaggcctga     960
agtcatcctc agaagggatg gatcctgagg tcgccatgcc cagctgggca aacatgagtc    1020
tggattcttc cccggagtcg gctgccttgg ctgtgaggct ggagggagat gagctgctag    1080
accacctgcg tctcagcatc ctgccctggg atgagagcat cctggacacc ctctcgccca    1140
ggctcgctac agcactgagt gaagaaatga aagacaaagg tggatacatg agcaagattt    1200
gcaacttgct acccattagg ataatgtctt atgtaatgct gccctgtacc ctgcctgtgg    1260
aatctgccat tgcgattgtc cagagactgg tgacatggct tccagatatg cccgacgatg    1320
tcctgtggtt gcagtgggtg acctcacagg tgttcactcg agtgctgatg tgtctgctcc    1380
ccgcctccag gtcccaaatg ccagtgagca gccaacaggc ctccccatgc acacctgagc    1440
aggactggcc ctgctggact ccctgctccc caagggctg tccagcagag accaaagcag    1500
aggccacccc gcggtccatc ctcaggtcca gcctgaactt cttcttgggc aataaagtac    1560
ctgctggtgc tgagggctc tccaccttc ccagttttc actagagaag agtctgtgag    1620
```

-continued

```
tcacttgagg aggcgagtct agcagattct ttcagaggtg ctaaagtttc ccatctttgt    1680
gcagctacct ccgcattgct gtgtagtgac ccctgcctgt gacgtggagg atcccagcct    1740
ctgagctgag ttggttttat gaaaagctag gaagcaacct ttcgcctgtg cagcggtcca    1800
gcacttaact ctaatacatc agcatgcgtt aattcagctg gttgggaaat gacaccagga    1860
agcccagtgc agagggtccc ttactgactg tttcgtggcc ctattaatgg tcagactgtt    1920
ccagcatgag gttcttagaa tgacaggtgt ttggatgggg gggggccttg tgatgggggg    1980
taggctggcc catgtgtgat cttgtggggt ggagggaaga gaatagcatg atcccacttc    2040
cccatgctgt gggaaggggt gcagttcgtc cccaagaacg acactgcctg tcaggtggtc    2100
tgcaaagatg ataaccttga ctactaaaaa cgtctccatg gcgggggtaa caagatgata    2160
atctacttaa ttttagaaca ccttttttcac ctaactaaaa taatgtttaa agagttttgt    2220
ataaaaatgt aaggaagcgt tgttacctgt tgaattttgt attatgtgaa tcagtgagat    2280
gttagtagaa taagccttaa aaaaaaaaaa atcggttggg tgcagtggca cacggctgta    2340
atcccagcac tttgggaggc caaggttggc agatcacctg aggtcaggag ttcaagacca    2400
gtctggccaa catagcaaaa ccctgtctct actaaaaata caaaaattat ctgggcatgg    2460
tggtgcatgc ctgtaatccc agctattcgg aaggctgagg caggagaatc acttgaaccc    2520
aggaggcgga ggttgcggtg agctgagatt gcaccatttc attccagcct gggcaacatg    2580
agtgaaagtc tgactcaaaa aaaaaaaatt taaaaacaa aataatctag tgtgcagggc    2640
attcacctca gccccccagg caggagccaa gcacagcagg agcttccgcc tcctctccac    2700
tggagcacac aacttgaacc tggcttattt tctgcaggga ccagcccac atggtcagtg    2760 agtttctccc catgtgtggc gatgagagag tgtagaaata aagac                    2805
```

<210> SEQ ID NO 2
<211> LENGTH: 19
<212> TYPE: RNA
<213> ORGANISM: Homo sapiens

<400> SEQUENCE: 2
accuuuuuca ccuaacuaa                                                 19

<210> SEQ ID NO 3
<211> LENGTH: 19
<212> TYPE: RNA
<213> ORGANISM: Homo sapiens

<400> SEQUENCE: 3
cuuucccagu uuucacua                                                  19

<210> SEQ ID NO 4
<211> LENGTH: 19
<212> TYPE: RNA
<213> ORGANISM: Homo sapiens

<400> SEQUENCE: 4
gguggauaca ugagcaaga                                                 19

<210> SEQ ID NO 5
<211> LENGTH: 19
<212> TYPE: RNA
<213> ORGANISM: Homo sapiens

<400> SEQUENCE: 5

-continued gguccaaaga cgaagucgu                                              19

<210> SEQ ID NO 6
<211> LENGTH: 19
<212> TYPE: RNA
<213> ORGANISM: Homo sapiens

<400> SEQUENCE: 6
aacguacccu ucauugaug                                              19

<210> SEQ ID NO 7
<211> LENGTH: 19
<212> TYPE: RNA
<213> ORGANISM: Homo sapiens

<400> SEQUENCE: 7
cugaguuggu uuuaugaaa                                              19

<210> SEQ ID NO 8
<211> LENGTH: 19
<212> TYPE: RNA
<213> ORGANISM: Homo sapiens

<400> SEQUENCE: 8
agcaagauuu gcaacuugc                                              19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 9
accuuuuuca ccuaacuan                                              19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 10
nccuuuuuca ccuaacuan                                              19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (18)..(18)
<223> OTHER INFORMATION: 2-aminoadenine nucleotide

<400> SEQUENCE: 11
accuuuuuca ccuaacuaa                                                  19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2-aminoadenine nucleotide
<220> FEATURE:
<221> NAME/KEY: modified_base
<222> LOCATION: (19)..(19)
<223> OTHER INFORMATION: Any nucleobase

<400> SEQUENCE: 12
accuuuuuca ccuaacuan                                                  19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (18)..(18)
<223> OTHER INFORMATION: 2-aminoadenine nucleotide
<220> FEATURE:
<221> NAME/KEY: modified_base
<222> LOCATION: (19)..(19)
<223> OTHER INFORMATION: Any nucleobase

<400> SEQUENCE: 13
nccuuuuuca ccuaacuan                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 14
cuuucccagu uuuucacun                                                  19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 15
nuuucccagu uuuucacun                                              19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 16
gguggauaca ugagcaagn                                              19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 17
nguggauaca ugagcaagn                                              19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: Hypoxanthine

<400> SEQUENCE: 18
gguggauaca ugancaaga                                              19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
```

<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 19
gguggauaca ugancaagn                                                                19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (14)..(14)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 20
nguggauaca ugancaagn                                                                19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gguccaaaga cgaagucga                                                                19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 22
gguccaaaga cgaagucgn                                                                19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 23
nguccaaaga cgaagucgn                                                  19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Hypoxanthine

<400> SEQUENCE: 24
gguccaaaga cgaagucnu                                                  19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Hypoxanthine

<400> SEQUENCE: 25
gguccaaaga cgaagucna                                                  19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 26
gguccaaaga cgaagucnn                                                  19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (18)..(18)
<223> OTHER INFORMATION: Hypoxanthine
<220> FEATURE:

<221> NAME/KEY: modified_base
<222> LOCATION: (19)..(19)
<223> OTHER INFORMATION: Any nucleobase

<400> SEQUENCE: 27
nguccaaaga cgaagucnn                                                19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Hypoxanthine
<220> FEATURE:
<221> NAME/KEY: modified_base
<222> LOCATION: (18)..(18)
<223> OTHER INFORMATION: Hypoxanthine

<400> SEQUENCE: 28
gguccaaaga cnaagucnu                                                19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Hypoxanthine
<220> FEATURE:
<221> NAME/KEY: modified_base
<222> LOCATION: (18)..(18)
<223> OTHER INFORMATION: Hypoxanthine

<400> SEQUENCE: 29
gguccaaaga cnaagucna                                                19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Hypoxanthine
<220> FEATURE:
<221> NAME/KEY: modified_base
<222> LOCATION: (18)..(18)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 30
gguccaaaga cnaagucnn                                                19

<210> SEQ ID NO 31
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (12)..(12)
<223> OTHER INFORMATION: Hypoxanthine
<220> FEATURE:
<221> NAME/KEY: modified_base
<222> LOCATION: (18)..(18)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 31
nguccaaaga cnaagucnn                                                19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: Hypoxanthine

<400> SEQUENCE: 32
gguccaaaga cgaanucgu                                                19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: Hypoxanthine

<400> SEQUENCE: 33
gguccaaaga cgaanucga                                                19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 34
gguccaaaga cgaanucgn                                                19
```

```
<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (15)..(15)
<223> OTHER INFORMATION: Hypoxanthine
<220> FEATURE:
<221> NAME/KEY: modified_base
<222> LOCATION: (19)..(19)
<223> OTHER INFORMATION: Any nucleobase

<400> SEQUENCE: 35
nguccaaaga cgaanucgn                                                19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aacguacccu ucauugaua                                                19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 37
aacguacccu ucauugaun                                                19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 38
nacguacccu ucauugaun                                                19

<210> SEQ ID NO 39
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 39
cugaguuggu uuuaugaan                                                   19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 40
nugaguuggu uuuaugaan                                                   19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
agcaagauuu gcaacuuga                                                   19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cgcaagauuu gcaacuuga                                                   19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 43
agcaagauuu gcaacuugn                                                   19
```

```
<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Any nucleobase

<400> SEQUENCE: 44
cgcaagauuu gcaacuugn                                                 19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 45
ngcaagauuu gcaacuugn                                                 19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uuaguuaggu gaaaaaggu                                                 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 47
nuaguuaggu gaaaaaggu                                                 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

-continued

<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 48
nuaguuaggu gaaaaaggn                                                19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uuaguuaggu gaaaaaggu                                                19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 50
nuaguuaggu gaaaaaggu                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 51
nuaguuaggu gaaaaaggn                                                19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uagugaaaaa cugggaaag                                                19

<210> SEQ ID NO 53
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 53
nagugaaaaa cugggaaag                                                    19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 54
nagugaaaaa cugggaaan                                                    19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ucuugcucau guauccacc                                                    19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 56
ncuugcucau guauccacc                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase
```

<400> SEQUENCE: 57
ncuugcucau guauccacn                                          19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ucuugcucau guauccacc                                          19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 59
ncuugcucau guauccacc                                          19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 60
ncuugcucau guauccacn                                          19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
acgacuucgu cuuuggacc                                          19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ucgacuucgu cuuuggacc                                              19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 63
ncgacuucgu cuuuggacc                                              19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 64
ncgacuucgu cuuuggacn                                              19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
acgacuucgu cuuuggacc                                              19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ucgacuucgu cuuuggacc                                              19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 67
ncgacuucgu cuuuggacc					19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 68
ncgacuucgu cuuuggacn					19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
acgacuucgu cuuuggacc					19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ucgacuucgu cuuuggacc					19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 71
ncgacuucgu cuuuggacc					19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 72
ncgacuucgu cuuggacn                                                 19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
acgacuucgu cuuggacc                                                 19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ucgacuucgu cuuggacc                                                 19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 75
ncgacuucgu cuuggacc                                                 19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 76
ncgacuucgu cuuggacn                                                 19

<210> SEQ ID NO 77
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 77
naucaaugaa ggguacguu                                                        19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uaucaaugaa ggguacguu                                                        19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 79
naucaaugaa ggguacgun                                                        19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 80
nuucauaaaa ccaacucag                                                        19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
```

<223> OTHER INFORMATION: Any nucleobase

<400> SEQUENCE: 81
nuucauaaaa ccaacucan                                                    19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gcaaguugca aaucuugcu                                                    19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ucaaguugca aaucuugcu                                                    19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ucaaguugca aaucuugcg                                                    19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 85
ncaaguugca aaucuugcu                                                    19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase

<400> SEQUENCE: 86
ncaaguugca aaucuugcg                                                    19

```
<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any nucleobase
<220> FEATURE:
<221> NAME/KEY: modified_base
<222> LOCATION: (19)..(19)
<223> OTHER INFORMATION: Any nucleobase

<400> SEQUENCE: 87
ncaaguugca aaucuugcn                                                    19

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
```

```
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 88
ucaucaauga aggguacguu g                                               21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorouridine-3'-phosphate
```

```
-continued

<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 89
ucaucaauga aggguacguc g                                           21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
```

<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 90
uagugaaaaa cugggaaagg u                                              21

<210> SEQ ID NO 91
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
```

```
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 91
uagugaaaaa cugggaaagg g                                          21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
```

```
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluoroadenosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 92
aaaucuugcu cauguaucca c                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
```

```
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methyluridine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 93
uacuugacuu uagggcagau g                                         21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
```

```
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methyluridine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 94
uacuugacuu uagggcagac g                                           21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

```
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
```

<222> LOCATION: (21)..(21)
<223> OTHER INFORMATION: 2'-O-methyluridine-3'-phosphate

<400> SEQUENCE: 95
uuaguuaggu gaaaaaggug u                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorocytidine-3'-phosphate

```
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 96
ucuugcucau guauccaccu g                                          21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
```

-continued

```
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 97
acgacuucgu cuuuggaccg a                                          21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorocytidine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyluridine-3'-phosphate
```

```
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluorouridine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 98
uaucaaugaa ggguacguug g                                          21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
```

```
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluoroadenosine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 99
uccaaauauc cucgaaggca g                                              21
```

```
<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
```

<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 100
uugaaaaacu gggaaaggug g                                          21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:

```
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 101
uucauaaaac caacucagcu c                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
```

<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 102
ucuugcucau guauccaccu g                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:

```
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluoroadenosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 103
agaacguuuu ccccaucaga c                                          21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
```

```
<222> LOCATION: (20)..(20)
<223> OTHER INFORMATION: 2'-O-methyluridine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 104
agaacguuuu ccccaucagu u                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-O-methyladenosine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methyluridine-3'-phosphate
```

```
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 105
uacaccagaa cguuuucccc a                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
```

```
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 106
ugaaagucag acaccagaac g                                             21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluoroguanosine-3'-phosphate
```

```
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-O-methyluridine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluorouridine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluoroadenosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 107
uaaggguacg uugucacuca c                                         21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
```

```
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-O-methylguanosine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate
```

<400> SEQUENCE: 108
uacuuuaggg cagaugucgu g                                                21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methyluridine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)

```
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 109
uguagcaagu ugcaaaucuc g                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2',3'-seco-uridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
```

<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroguanosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 110
acgacuucgu cuuuggaccg a                                               21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)

```
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 111
acaagaucug agaggaccug c                                           21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
```

```
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluoroguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 112
ucaaugaagg guacguuguc g                                           21

<210> SEQ ID NO 113
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorocytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
```

<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 113
aaucuugcuc auguauccac c                                    21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate

```
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 114
uugucauuuc ccaaccagcu g                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroadenosine-3'-phosphorothioate
<220> FEATURE:
<221> NAME/KEY: modified_base
<222> LOCATION: (3)..(3)
<223> OTHER INFORMATION: 2'-O-methylguanosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
```

<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-fluoroguanosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 115
uagugaaaaa cugggaaagg c                                           21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate

```
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 116
ucuugcucau guaccaccu u                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorocytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
```

<221> NAME/KEY: modified_base
<222> LOCATION: (21)..(21)
<223> OTHER INFORMATION: 2'-O-methylcytidine-3'-phosphate

<400> SEQUENCE: 117
ucuugcucau guauccaccu c                                         21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)

-continued

```
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 118
uuaguuaggu gaaaaaggug c                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5'-cyclopropyl phosphonate-2'-O-methyl
      uridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
```

-continued

```
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 119
uuaguuaggu gaaaaaggug u                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2',3'-seco-uridine-3'-phosphate
<220> FEATURE:
<221> NAME/KEY: modified_base
```

```
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 120
uuaguuaggu gaaaaaggug u                                           21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
```

```
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2',3'-seco-adenosine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 121
```

-continued uuaguuaggu gaaaaaggug u                                                    21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroguanosine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2',3'-seco-guanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:

```
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluoroguanosine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 122
uuaguuaggu gaaaaaggug u                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyladenosine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
<223> OTHER INFORMATION: 2'-fluorocytidine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
```

-continued

```
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-fluoroadenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-fluoroguanosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 123
auccaaauau ccucgaaggc a                                         21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluorouridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
```

```
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-fluorouridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluorouridine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 124
ucauguaucc accuuugucu u                                         21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluoroguanosine-3'-phosphorothioate
<220> FEATURE:
<221> NAME/KEY: modified_base
<222> LOCATION: (3)..(3)
<223> OTHER INFORMATION: 2'-O-methylcytidine-3'-phosphorothioate
<220> FEATURE:
<221> NAME/KEY: modified_base
<222> LOCATION: (4)..(4)
```

<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluoroadenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorocytidine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-O-methylguanosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluorouridine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-fluorouridine-3'-phosphorothioate
<220> FEATURE:
<221> NAME/KEY: modified_base
<222> LOCATION: (21)..(21)
<223> OTHER INFORMATION: 2'-O-methylcytidine-3'-phosphate

<400> SEQUENCE: 125
ugcaaaucuu gcucauguau c                                          21

<210> SEQ ID NO 126
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methyluridine-3'-phosphate
```

```
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methyladenosine-3'-phosphate

<400> SEQUENCE: 126
ucaaguugca aaucuugcuc a                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorocytidine-3'-phosphorothioate
<220> FEATURE:
<221> NAME/KEY: modified_base
<222> LOCATION: (3)..(3)
<223> OTHER INFORMATION: 2'-O-methyladenosine-3'-phosphorothioate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-fluorocytidine-3'-phosphate
<220> FEATURE:
<221> NAME/KEY: modified_base
```

<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-fluorocytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methylguanosine-3'-phosphate

<400> SEQUENCE: 127
ucaaguugca aaucuugcuc g                                          21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyluridine-3'-phosphorothioate
<220> FEATURE:
<221> NAME/KEY: modified_base
<222> LOCATION: (2)..(2)
<223> OTHER INFORMATION: 2'-fluorouridine-3'-phosphorothioate
<220> FEATURE:
<221> NAME/KEY: modified_base
<222> LOCATION: (3)..(3)
<223> OTHER INFORMATION: 2'-O-methyluridine-3'-phosphorothioate
<220> FEATURE:
<221> NAME/KEY: modified_base
<222> LOCATION: (4)..(4)
<223> OTHER INFORMATION: 2'-fluorocytidine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-fluorouridine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-fluoroadenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate

```
<220> FEATURE:
<221> NAME/KEY: modified_base
<222> LOCATION: (11)..(11)
<223> OTHER INFORMATION: 2'-O-methylcytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-fluoroadenosine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-fluorouridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-fluoroadenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-fluorocytidine-3'-phosphorothioate
<220> FEATURE:
<221> NAME/KEY: modified_base
<222> LOCATION: (21)..(21)
<223> OTHER INFORMATION: 2'-O-methyluridine-3'-phosphate

<400> SEQUENCE: 128
uuucauaaaa ccaacucagc u                                          21

<210> SEQ ID NO 129
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
```

```
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 129
ncaacguacc cuucauugau gan                                           23
```

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:

```
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 130
ncgacguacc cuucauugau gan                                          23

<210> SEQ ID NO 131
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
```

```
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 131
naccuuuccc aguuuuucac uan                                           23

<210> SEQ ID NO 132
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
```

```
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
```

<222> LOCATION: (23)..(23)
<223> OTHER INFORMATION: inverted abasic deoxyribonucleotide

<400> SEQUENCE: 132
ncccuuuccc aguuuuucac uan                                           23

<210> SEQ ID NO 133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methyluridine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:

<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 133
nguggauaca ugagcaagau uun                                           23

<210> SEQ ID NO 134
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methyluridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylcytidine-3'-phosphate

```
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 134
ncaucugccc uaaagucaag uan                                             23

<210> SEQ ID NO 135
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
```

```
        phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyluridine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
```

```
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 135
ncgucugccc uaaagucaag uan                                          23

<210> SEQ ID NO 136
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
```

<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 136
nacaccuuuu ucaccuaacu aan                                          23

<210> SEQ ID NO 137
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate

```
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 137
ncagguggau acaugagcaa gan                                          23

<210> SEQ ID NO 138
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylinosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
```

-continued

```
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 138
ncagguggau acaugancaa gan                                              23

<210> SEQ ID NO 139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylcytidine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
```

<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methylinosine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 139
nucgguccaa agacgaaguc nun                                           23

<210> SEQ ID NO 140
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate

```
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 140
```
nccaacguac ccuucauuga uan                                                      23

<210> SEQ ID NO 141
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyluridine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base

```
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylinosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 141
ncugccuucg aggauauuun gan                                          23

<210> SEQ ID NO 142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
```

```
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 142
nccaccuuuc ccaguuuuuc aan                                             23

<210> SEQ ID NO 143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
```

```
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
```

```
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 143
ngagcugagu ugguuuuaug aan                                         23

<210> SEQ ID NO 144
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methyluridine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
```

```
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylcytidine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 144
ngucugaugg ggaaaacguu cun                                           23

<210> SEQ ID NO 145
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyluridine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
```

```
<221> NAME/KEY: modified_base
<222> LOCATION: (8)..(8)
<223> OTHER INFORMATION: 2'-fluoroguanosine-3'-phosphate
<220> FEATURE:
<221> NAME/KEY: modified_base
<222> LOCATION: (9)..(9)
<223> OTHER INFORMATION: 2'-fluoroguanosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-O-methyladenosine-3'-phosphate
<220> FEATURE:
<221> NAME/KEY: modified_base
<222> LOCATION: (12)..(12)
<223> OTHER INFORMATION: 2'-O-methyladenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methylguanosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 145
ncugaugggg aaaacguucu uun                                           23

<210> SEQ ID NO 146
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
```

```
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methylguanosine-3'-phosphate
<220> FEATURE:
<221> NAME/KEY: modified_base
<222> LOCATION: (18)..(18)
<223> OTHER INFORMATION: 2'-O-methylinosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
```

```
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 146 nugggggaaaaa cguucugnug uan                                          23

<210> SEQ ID NO 147
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyluridine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
```

```
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylcytidine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 147
ncguucuggu gucugacuuu can                                              23

<210> SEQ ID NO 148
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methyluridine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
```

```
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 148
ngugagugac aacguacccu uan                                          23

<210> SEQ ID NO 149
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-O-methylcytidine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
```

<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 149
ncacgacauc ugcccuaaag uan                                              23

<210> SEQ ID NO 150
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base

```
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluoroadenosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methylinosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylcytidine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 150
ncgagauuug caacuuncua can                                            23

<210> SEQ ID NO 151
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
```

```
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylcytidine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide
```

<400> SEQUENCE: 151
nucgguccaa agacgaaguc gun                                           23

<210> SEQ ID NO 152
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylcytidine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)

```
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylinosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 152
nucgguccaa agacgaanuc gun                                          23

<210> SEQ ID NO 153
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
```

```
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyl-2-aminoadenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 153
nccaccuuuu ucaccuaacu aan                                           23

<210> SEQ ID NO 154
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
```

```
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methylinosine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorocytidine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
```

```
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 154
ngcagnuccu cucagaucuu gun                                            23

<210> SEQ ID NO 155
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyladenosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methylcytidine-3'-phosphate
<220> FEATURE:
<221> NAME/KEY: modified_base
<222> LOCATION: (14)..(14)
```

```
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methylcytidine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 155
ncgacaacgu acccuucauu gan                                              23

<210> SEQ ID NO 156
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyluridine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
```

```
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methylcytidine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 156
ngguggauac augagcaaga uun                                        23

<210> SEQ ID NO 157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylguanosine-3'-phosphate
<220> FEATURE:
<221> NAME/KEY: modified_base
<222> LOCATION: (19)..(19)
<223> OTHER INFORMATION: 2'-O-methyladenosine-3'-phosphate
```

```
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 157
ncagcugguu gggaaaugac aan                                           23

<210> SEQ ID NO 158
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylcytidine-3'-phosphate
<220> FEATURE:
<221> NAME/KEY: modified_base
<222> LOCATION: (10)..(10)
<223> OTHER INFORMATION: 2'-fluorocytidine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
```

```
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methylcytidine-3'-phosphate
<220> FEATURE:
<221> NAME/KEY: modified_base
<222> LOCATION: (21)..(21)
<223> OTHER INFORMATION: 2'-O-methyluridine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 158
ngccuuuccc aguuuuucac uan                                             23

<210> SEQ ID NO 159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
```

```
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylinosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 159
naagguggau acaugancaa gan                                           23
```

```
<210> SEQ ID NO 160
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylinosine-3'-phosphate
```

```
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 160
ngagguggau acaugancaa gan                                              23

<210> SEQ ID NO 161
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyl-2-aminoadenosine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methylguanosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
```

```
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroadenosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methylinosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 161
naagguggau acaugancaa gan                                           23

<210> SEQ ID NO 162
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
```

```
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
```

```
<221> NAME/KEY: modified_base
<222> LOCATION: (23)..(23)
<223> OTHER INFORMATION: inverted abasic deoxyribonucleotide

<400> SEQUENCE: 162
ngcaccuuuu ucaccuaacu aan                                            23

<210> SEQ ID NO 163
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
```

<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyl-2-aminoadenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 163
ngcaccuuuu ucaccuaacu aan                                            23

<210> SEQ ID NO 164
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyl-2-aminoadenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)

```
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 164
nacaccuuuu ucaccuaacu aan                                            23

<210> SEQ ID NO 165
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
```

```
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
```

```
<221> NAME/KEY: modified_base
<222> LOCATION: (21)..(21)
<223> OTHER INFORMATION: 2'-O-methyl-2-aminoadenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 165
nacaccuuuu ucaccuaacu aan                                             23

<210> SEQ ID NO 166
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyl-2-aminoadenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
```

```
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyl-2-aminoadenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 166
nacaccuuuu ucaccuaacu aan                                              23

<210> SEQ ID NO 167
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methylcytidine-3'-phosphate
<220> FEATURE:
<221> NAME/KEY: modified_base
<222> LOCATION: (4)..(4)
<223> OTHER INFORMATION: 2'-fluoroadenosine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
```

```
<223> OTHER INFORMATION: 2'-fluorocytidine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-fluorouridine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methylcytidine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyladenosine-3'-phosphate
<220> FEATURE:
<221> NAME/KEY: modified_base
<222> LOCATION: (19)..(19)
<223> OTHER INFORMATION: 2'-O-methylcytidine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 167
nacaccuuuu ucaccuaacu aan                                          23

<210> SEQ ID NO 168
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methylcytidine-3'-phosphate
<220> FEATURE:
<221> NAME/KEY: modified_base
<222> LOCATION: (6)..(6)
<223> OTHER INFORMATION: 2'-O-methyluridine-3'-phosphate
<220> FEATURE:
<221> NAME/KEY: modified_base
<222> LOCATION: (7)..(7)
<223> OTHER INFORMATION: 2'-O-methyluridine-3'-phosphate
<220> FEATURE:
<221> NAME/KEY: modified_base
<222> LOCATION: (8)..(8)
<223> OTHER INFORMATION: 2'-O-methylcytidine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
```

<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
<222> LOCATION: (22)..(22)
<223> OTHER INFORMATION: 2'-O-methyluridine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 168
nugccuucga ggauauuugg aun                                            23

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyl-2-aminoadenosine-3'-phosphate
<220> FEATURE:
<221> NAME/KEY: modified_base
<222> LOCATION: (3)..(3)
<223> OTHER INFORMATION: 2'-O-methyladenosine-3'-phosphate
<220> FEATURE:
<221> NAME/KEY: modified_base
<222> LOCATION: (4)..(4)
<223> OTHER INFORMATION: 2'-O-methylguanosine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methyladenosine-3'-phosphate
<220> FEATURE:
<221> NAME/KEY: modified_base
<222> LOCATION: (10)..(10)
<223> OTHER INFORMATION: 2'-fluoroguanosine-3'-phosphate
<220> FEATURE:
<221> NAME/KEY: modified_base
<222> LOCATION: (11)..(11)
<223> OTHER INFORMATION: 2'-fluoroguanosine-3'-phosphate

```
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methylguanosine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methyladenosine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyladenosine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 169
naagacaaag guggauacau gan                                           23

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylguanosine-3'-phosphate
<220> FEATURE:
<221> NAME/KEY: modified_base
<222> LOCATION: (3)..(3)
<223> OTHER INFORMATION: 2'-O-methyl-2-aminoadenosine-3'-phosphate
<220> FEATURE:
<221> NAME/KEY: modified_base
<222> LOCATION: (4)..(4)
```

<223> OTHER INFORMATION: 2'-O-methyluridine-3'-phosphate
<220> FEATURE:
<221> NAME/KEY: modified_base
<222> LOCATION: (5)..(5)
<223> OTHER INFORMATION: 2'-O-methyladenosine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyluridine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluorocytidine-3'-phosphate
<220> FEATURE:
<221> NAME/KEY: modified_base
<222> LOCATION: (13)..(13)
<223> OTHER INFORMATION: 2'-O-methyladenosine-3'-phosphate
<220> FEATURE:
<221> NAME/KEY: modified_base
<222> LOCATION: (14)..(14)
<223> OTHER INFORMATION: 2'-O-methyladenosine-3'-phosphate
<220> FEATURE:
<221> NAME/KEY: modified_base
<222> LOCATION: (15)..(15)
<223> OTHER INFORMATION: 2'-O-methylguanosine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyluridine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methylguanosine-3'-phosphate
<220> FEATURE:
<221> NAME/KEY: modified_base
<222> LOCATION: (21)..(21)
<223> OTHER INFORMATION: 2'-O-methylcytidine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 170
ngauacauga gcaagauuug can                                       23

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methyluridine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylguanosine-3'-phosphate
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:

<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 171
nugagcaaga uuugcaacuu gan                                    23

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
<223> OTHER INFORMATION: 2'-O-methylcytidine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methyladenosine-3'-phosphate
<220> FEATURE:
<221> NAME/KEY: modified_base
<222> LOCATION: (5)..(5)
<223> OTHER INFORMATION: 2'-O-methylguanosine-3'-phosphate
<220> FEATURE:
<221> NAME/KEY: modified_base
<222> LOCATION: (6)..(6)
<223> OTHER INFORMATION: 2'-O-methylcytidine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methyladenosine-3'-phosphate
<220> FEATURE:
<221> NAME/KEY: modified_base
<222> LOCATION: (9)..(9)
<223> OTHER INFORMATION: 2'-O-methylguanosine-3'-phosphate

```
<220> FEATURE:
<221> NAME/KEY: modified_base
<222> LOCATION: (10)..(10)
<223> OTHER INFORMATION: 2'-fluoroadenosine-3'-phosphate
<220> FEATURE:
<221> NAME/KEY: modified_base
<222> LOCATION: (11)..(11)
<223> OTHER INFORMATION: 2'-fluorouridine-3'-phosphate
<220> FEATURE:
<221> NAME/KEY: modified_base
<222> LOCATION: (12)..(12)
<223> OTHER INFORMATION: 2'-fluorouridine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methylguanosine-3'-phosphate
<220> FEATURE:
<221> NAME/KEY: modified_base
<222> LOCATION: (15)..(15)
<223> OTHER INFORMATION: 2'-O-methylcytidine-3'-phosphate
<220> FEATURE:
<221> NAME/KEY: modified_base
<222> LOCATION: (16)..(16)
<223> OTHER INFORMATION: 2'-O-methyladenosine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methylcytidine-3'-phosphate
<220> FEATURE:
<221> NAME/KEY: modified_base
<222> LOCATION: (19)..(19)
<223> OTHER INFORMATION: 2'-O-methyluridine-3'-phosphate
<220> FEATURE:
<221> NAME/KEY: modified_base
<222> LOCATION: (20)..(20)
<223> OTHER INFORMATION: 2'-O-methyluridine-3'-phosphate
<220> FEATURE:
<221> NAME/KEY: modified_base
<222> LOCATION: (21)..(21)
<223> OTHER INFORMATION: 2'-O-methylguanosine-3'-phosphate
<220> FEATURE:
<221> NAME/KEY: modified_base
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 172
ncgagcaaga uuugcaacuu gan                                            23

<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NAG37-phosphorothioate
<220> FEATURE:
<221> NAME/KEY: modified_base
<222> LOCATION: (1)..(1)
<223> OTHER INFORMATION: inverted abasic deoxyribonucleotide-5'-
      phosphorothioate
<220> FEATURE:
<221> NAME/KEY: modified_base
<222> LOCATION: (2)..(2)
```

```
<223> OTHER INFORMATION: 2'-O-methyladenosine-3'-phosphate
<220> FEATURE:
<221> NAME/KEY: modified_base
<222> LOCATION: (3)..(3)
<223> OTHER INFORMATION: 2'-O-methylguanosine-3'-phosphate
<220> FEATURE:
<221> NAME/KEY: modified_base
<222> LOCATION: (4)..(4)
<223> OTHER INFORMATION: 2'-O-methylcytidine-3'-phosphate
<220> FEATURE:
<221> NAME/KEY: modified_base
<222> LOCATION: (5)..(5)
<223> OTHER INFORMATION: 2'-O-methyluridine-3'-phosphate
<220> FEATURE:
<221> NAME/KEY: modified_base
<222> LOCATION: (6)..(6)
<223> OTHER INFORMATION: 2'-O-methylguanosine-3'-phosphate
<220> FEATURE:
<221> NAME/KEY: modified_base
<222> LOCATION: (7)..(7)
<223> OTHER INFORMATION: 2'-O-methyladenosine-3'-phosphate
<220> FEATURE:
<221> NAME/KEY: modified_base
<222> LOCATION: (8)..(8)
<223> OTHER INFORMATION: 2'-O-methylguanosine-3'-phosphate
<220> FEATURE:
<221> NAME/KEY: modified_base
<222> LOCATION: (9)..(9)
<223> OTHER INFORMATION: 2'-O-methyluridine-3'-phosphate
<220> FEATURE:
<221> NAME/KEY: modified_base
<222> LOCATION: (10)..(10)
<223> OTHER INFORMATION: 2'-fluorouridine-3'-phosphate
<220> FEATURE:
<221> NAME/KEY: modified_base
<222> LOCATION: (11)..(11)
<223> OTHER INFORMATION: 2'-fluoroguanosine-3'-phosphate
<220> FEATURE:
<221> NAME/KEY: modified_base
<222> LOCATION: (12)..(12)
<223> OTHER INFORMATION: 2'-fluoroguanosine-3'-phosphate
<220> FEATURE:
<221> NAME/KEY: modified_base
<222> LOCATION: (13)..(13)
<223> OTHER INFORMATION: 2'-O-methyluridine-3'-phosphate
<220> FEATURE:
<221> NAME/KEY: modified_base
<222> LOCATION: (14)..(14)
<223> OTHER INFORMATION: 2'-O-methyluridine-3'-phosphate
<220> FEATURE:
<221> NAME/KEY: modified_base
<222> LOCATION: (15)..(15)
<223> OTHER INFORMATION: 2'-O-methyluridine-3'-phosphate
<220> FEATURE:
<221> NAME/KEY: modified_base
<222> LOCATION: (16)..(16)
<223> OTHER INFORMATION: 2'-O-methyluridine-3'-phosphate
<220> FEATURE:
<221> NAME/KEY: modified_base
<222> LOCATION: (17)..(17)
<223> OTHER INFORMATION: 2'-O-methyladenosine-3'-phosphate
<220> FEATURE:
<221> NAME/KEY: modified_base
<222> LOCATION: (18)..(18)
<223> OTHER INFORMATION: 2'-O-methyluridine-3'-phosphate
<220> FEATURE:
<221> NAME/KEY: modified_base
<222> LOCATION: (19)..(19)
<223> OTHER INFORMATION: 2'-O-methylguanosine-3'-phosphate
<220> FEATURE:
<221> NAME/KEY: modified_base
<222> LOCATION: (20)..(20)
<223> OTHER INFORMATION: 2'-O-methyladenosine-3'-phosphate
<220> FEATURE:
<221> NAME/KEY: modified_base
<222> LOCATION: (21)..(21)
<223> OTHER INFORMATION: 2'-O-methyladenosine-3'-phosphate
<220> FEATURE:
<221> NAME/KEY: modified_base
```

```
<222> LOCATION: (22)..(22)
<223> OTHER INFORMATION: 2'-O-methyladenosine-3'-phosphorothioate
<220> FEATURE:
<221> NAME/KEY: modified_base
<222> LOCATION: (23)..(23)
<223> OTHER INFORMATION: inverted abasic deoxyribonucleotide

<400> SEQUENCE: 173
nagcugaguu gguuuuauga aan                                              23

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ucaucaauga aggguacguu g                                                21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ucaucaauga aggguacguc g                                                21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uagugaaaaa cugggaaagg u                                                21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uagugaaaaa cugggaaagg g                                                21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
aaaucuugcu cauguaucca c                                                21

<210> SEQ ID NO 179
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uacuugacuu uagggcagau g                                           21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uacuugacuu uagggcagac g                                           21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uuaguuaggu gaaaaaggug u                                           21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ucuugcucau guauccaccu g                                           21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
acgacuucgu cuuuggaccg a                                           21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uaucaaugaa ggguacguug g                                           21

<210> SEQ ID NO 185
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 185
uccaaauauc cucgaaggca g                                                   21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uugaaaaacu gggaaaggug g                                                   21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uucauaaaac caacucagcu c                                                   21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ucuugcucau guauccaccu g                                                   21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
agaacguuuu ccccaucaga c                                                   21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
agaacguuuu ccccaucagu u                                                   21

<210> SEQ ID NO 191
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 191
uacaccagaa cguuucccc a                                                    21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ugaaagucag acaccagaac g                                                   21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uaaggguacg uugucacuca c                                                   21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uacuuuaggg cagaugucgu g                                                   21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uguagcaagu ugcaaaucuc g                                                   21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
acgacuucgu cuuuggaccg a                                                   21

<210> SEQ ID NO 197
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 197
acaagaucug agaggaccug c                                               21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ucaaugaagg guacguuguc g                                               21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
aaucuugcuc auguauccac c                                               21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uugucauuuc ccaaccagcu g                                               21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uagugaaaaa cugggaaagg c                                               21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ucuugcucau guauccaccu u                                               21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 203
ucuugcucau guauccaccu c                                              21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uuaguuaggu gaaaaaggug c                                              21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uuaguuaggu gaaaaaggug u                                              21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
auccaaauau ccucgaaggc a                                              21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ucauguaucc accuuugucu u                                              21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
ugcaaaucuu gcucauguau c                                              21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ucaaguugca aaucuugcuc a                                              21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ucaaguugca aaucuugcuc g                                              21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uuucauaaaa ccaacucagc u                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
caacguaccc uucauugaug a                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cgacguaccc uucauugaug a                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
accuuuccca guuuuucacu a                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
-continued

<400> SEQUENCE: 215
cccuuuccca guuuuucacu a                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
guggauacau gagcaagauu u                                              21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
caucugcccu aaagucaagu a                                              21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cgucugcccu aaagucaagu a                                              21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
acaccuuuuu caccuaacua a                                              21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cagguggaua caugagcaag a                                              21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (16)..(16)
<223> OTHER INFORMATION: Hypoxanthine

<400> SEQUENCE: 221
cagguggaua caugancaag a                                              21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Hypoxanthine

<400> SEQUENCE: 222
ucgguccaaa gacgaagucn u                                              21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ccaacguacc cuucauugau a                                              21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Hypoxanthine

<400> SEQUENCE: 224
cugccuucga ggauauuung a                                              21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ccaccuuucc caguuuuuca a                                              21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gagcugaguu gguuuuauga a                                              21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gucugauggg gaaaacguuc u                                                 21

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228 cugauggga aaacguucuu u                                                  21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Hypoxanthine

<400> SEQUENCE: 229 ugggaaaac guucugnugu a                                                  21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230 cguucggug ucugacuuuc a                                                  21

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
gugagugaca acguacccuu a                                                 21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 232
cacgacaucu gcccuaaagu a                                              21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Hypoxanthine

<400> SEQUENCE: 233
cgagauuugc aacuuncuac a                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ucgguccaaa gacgaagucg u                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Hypoxanthine

<400> SEQUENCE: 235
ucgguccaaa gacgaanucg u                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2-aminoadenine nucleotide

<400> SEQUENCE: 236
ccaccuuuuu caccuaacua a                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
```

<223> OTHER INFORMATION: Hypoxanthine

<400> SEQUENCE: 237
gcagnuccuc ucagaucuug u                                           21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cgacaacgua cccuucauug a                                           21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
gguggauaca ugagcaagau u                                           21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cagcugguug ggaaaugaca a                                           21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gccuuuccca guuuuucacu a                                           21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Hypoxanthine

<400> SEQUENCE: 242
aagguggaua caugancaag a                                           21

<210> SEQ ID NO 243
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Hypoxanthine

<400> SEQUENCE: 243
gagguggaua caugancaag a                                              21

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-aminoadenine nucleotide
<220> FEATURE:
<221> NAME/KEY: modified_base
<222> LOCATION: (16)..(16)
<223> OTHER INFORMATION: Hypoxanthine

<400> SEQUENCE: 244
aagguggaua caugancaag a                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gcaccuuuuu caccuaacua a                                              21

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gcaccuuuuu caccuaacua a                                              21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-aminoadenine nucleotide

<400> SEQUENCE: 247
acaccuuuuu caccuaacua a                                              21

<210> SEQ ID NO 248
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2-aminoadenine nucleotide

<400> SEQUENCE: 248
acaccuuuuu caccuaacua a                                                   21

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-aminoadenine nucleotide

<400> SEQUENCE: 249
acaccuuuuu caccuaacua a                                                   21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
acaccuuuuu caccuaacua a                                                   21

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ugccuucgag gauauuugga u                                                   21

<210> SEQ ID NO 252
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-aminoadenine nucleotide

<400> SEQUENCE: 252
aagacaaagg uggauacaug a                                                   21

<210> SEQ ID NO 253
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2-aminoadenine nucleotide

<400> SEQUENCE: 253
gauacaugag caagauuugc a                                              21

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ugagcaagau uugcaacuug a                                              21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
cgagcaagau uugcaacuug a                                              21

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
agcugaguug guuuuaugaa a                                              21

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
caucaaugaa ggguacguu                                                 19

<210> SEQ ID NO 258
<211> LENGTH: 19
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 258
uuucauaaaa ccaacucag                                                  19
```

RNAi AGENTS FOR INHIBITING EXPRESSION OF PNPLA3, PHARMACEUTICAL COMPOSITIONS THEREOF, AND METHODS OF USE

CROSS-REFERENCE TO RELATED APPLICATIONS

This application claims the benefit of U.S. Provisional Appl. No. 63/000,137, filed Mar. 26, 2020, which application is incorporated by reference herein in its entirety.

SEQUENCE LISTING

The instant application contains a Sequence Listing which has been submitted electronically in ASCII format and is hereby incorporated by reference in its entirety. Said ASCII copy, created on Mar. 25, 2021, is named 103693_002474_US_SL.txt and is 241,534 bytes in size.

FIELD OF THE INVENTION

The present disclosure relates to RNA interference (RNAi) agents, e.g., double stranded RNAi agents, for inhibition of Patatin-like phospholipase domain-containing protein 3 (PNPLA3), pharmaceutical compositions that include PNPLA3 RNAi agents, and methods of use thereof.

BACKGROUND

Nonalcoholic fatty liver disease (NAFLD) is the most common chronic liver disease in the world and is estimated to affect approximately 20% of the world population. In some individuals the accumulation of ectopic fat in the liver, called steatosis, triggers inflammation and hepatocellular injury leading to a more advanced stage of disease called, nonalcoholic steatohepatitis (NASH). Treatments for NAFLD are often directed towards weight loss and treatment of any secondary conditions, such as insulin resistance or dyslipidemia.

Patatin-like phospholipase domain-containing 3 (PNPLA3), a type II transmembrane protein is expressed in various cells including in the liver. In hepatocytes, PNPLA3 is expressed on the endoplasmic reticulum and lipid membranes and predominantly exhibits triacylglycerol hydrolase activity.

The present invention represents a novel approach to reducing PNPLA3 levels and treating hepatologic diseases, such as NAFLD.

SUMMARY

Disclosed herein are RNAi agents for inhibiting expression of a PNPLA3 gene, comprising an antisense strand comprising at least 17 contiguous nucleotides differing by 0 or 1 nucleotides from any one of the sequences of SEQ ID NOs: 46-60, 176, 181 and 188; and a sense strand comprising a nucleotide sequence that is at least partially complementary to the antisense strand.

In some embodiments, the antisense strand comprises nucleotides 2-18 of any one of the sequences of SEQ ID NOs: 46-60, 176, 181 and 188.

In some embodiments, the sense strand comprises a nucleotide sequence of at least 17 contiguous nucleotides differing by 0 or 1 nucleotides from any one of the sense strand sequences of SEQ ID NOs: 2, 3, 4, 9-20, 214, 219 and 220, and wherein the sense strand has a region of at least 85% complementarity over the 17 contiguous nucleotides to the antisense strand.

In some embodiments, the least one nucleotide of the RNAi agent is a modified nucleotide or includes a modified internucleoside linkage.

According to some embodiments, all or substantially all of the nucleotides of the sense and/or antisense strand of the RNAi agent are modified nucleotides.

In some embodiments, the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

In other embodiments, the all or substantially all of the modified nucleotides are 2'-O-methyl nucleotides, 2'-fluoro nucleotides, or combinations thereof.

In some embodiments, the antisense strand consists of, consists essentially of, or comprises the nucleotide sequence of any one of the modified antisense strand sequences of SEQ ID NOs: 90, 95 and 102.

In some embodiments, the sense strand consists of, consists essentially of, or comprises the nucleotide sequence of any of the modified sense strand sequences of SEQ ID NOs: 131, 136 and 137.

In some embodiments, the antisense strand comprises the nucleotide sequence of any one of the modified sequences of SEQ ID NOs: 90, 95 and 102 and the sense strand comprises the nucleotide sequence of any one of the modified sequences of SEQ ID NOs: 131, 136 and 137.

In other embodiments, the RNAi agents are linked to a targeting ligand. In some embodiments, the targeting ligand comprises N-acetyl-galactosamine. In yet other embodiments, the targeting ligand comprises the structure of (NAG37) or (NAG37)s. In further embodiments, the targeting ligand is linked to the sense strand. In some embodiments, the targeting ligand is linked to the 5' terminal end of the sense strand.

In some embodiments, the targeting sense strand is between 18 and 30 nucleotides in length, and the antisense strand is between 18 and 30 nucleotides in length. In other embodiments, the targeting the sense strand and the antisense strand are each between 18 and 27 nucleotides in length. In other embodiments, the targeting the sense strand and the antisense strand are each between 18 and 24 nucleotides in length. In still other embodiments, sense strand and the antisense strand are each 21 nucleotides in length.

In some embodiments, the RNAi agents have two blunt ends.

In some embodiments, the sense strand comprises one or two terminal caps. In other embodiments, the sense strand comprises one or two inverted abasic residues.

In some embodiments, the RNAi agents are comprised of a sense strand and an antisense strand that form a duplex sequence with SEQ ID NOs: (176 and 214); (90 and 131); (181 and 219); (95 and 136); (188 and 220) and/or (102 and 137).

In some embodiments, the sense strand further includes inverted abasic residues at the 3' terminal end of the nucleotide sequence, at the 5' end of the nucleotide sequence, or at both.

In some aspects, the RNAi agents provided herein comprise an antisense strand that comprises, consists of, or consists essentially of a modified nucleotide sequence that differs by 0 or 1 nucleotides from one of the nucleotide sequences of SEQ ID NOs: 90, 95 and 102; wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; s represents a phosphorothioate linkage; and wherein all or substantially all of the nucleotides on the sense strand are modified nucleotides.

In some embodiments, the disclosed sense strand comprises, consists of, or consists essentially of a modified nucleotide sequence that differs by 0 or 1 nucleotides from one of the nucleotide sequences of SEQ ID NOs: 214, 219 and 256; wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; s represents a phosphorothioate linkage; and wherein all or substantially all of the nucleotides on the antisense strand are modified nucleotides. In other embodiments, the sense strand further includes inverted abasic residues at the 3' terminal end of the nucleotide sequence, at the 5' end of the nucleotide sequence, or at both. In other embodiments, the sense strand of the RNAi agents is linked to a targeting ligand.

In some embodiments, the targeting ligand has affinity for the asialoglycoprotein receptor. In some embodiments, the targeting ligand comprises N-acetyl-galactosamine.

In further embodiments, the targeting ligand comprises:

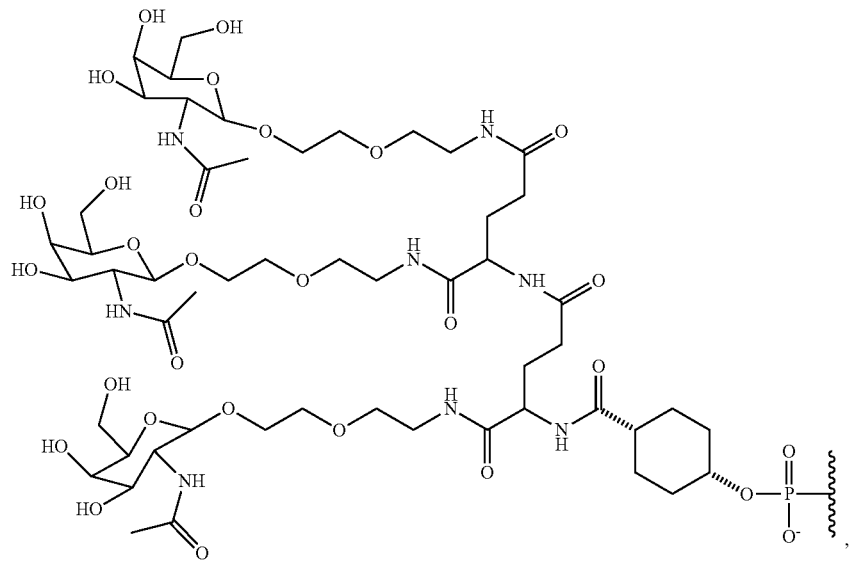

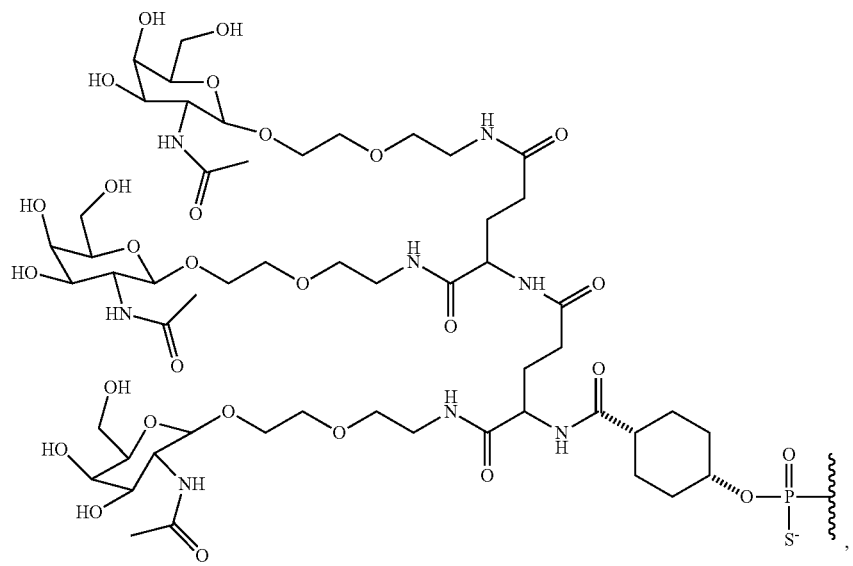

In further embodiments, the antisense strand consists of the modified nucleotide sequence of SEQ ID NOs: 90, 95 and 102, and the sense strand consists of the modified nucleotide sequence of SEQ ID NOs: 131, 136 and 137; wherein a, c, g, and u are 2'-O-methyl adenosine, cytidine, guanosine, and uridine, respectively; Af, Cf, Gf, and Uf are 2'-fluoro adenosine, cytidine, guanosine, and uridine, respectively; s is a phosphorothioate linkage; (invAb) is an inverted abasic deoxyribose residue; and (NAG37)s has the following chemical structure:

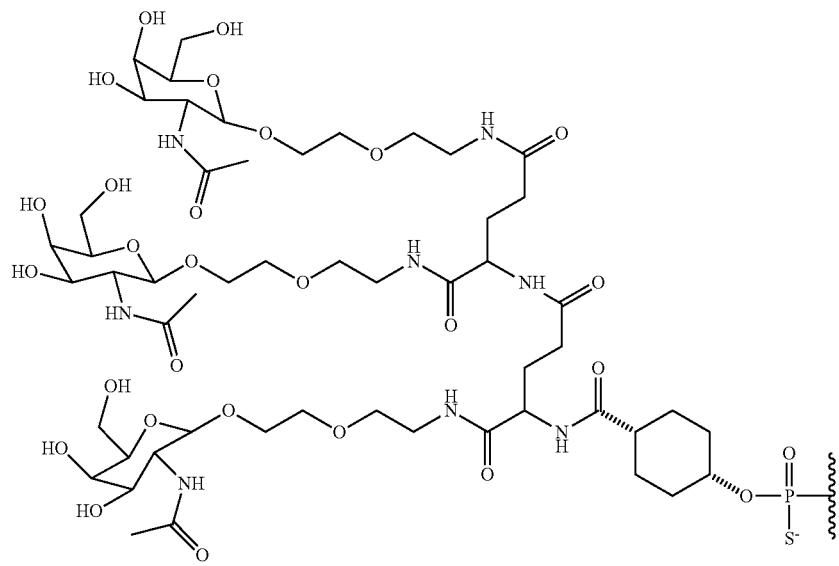

Also disclosed herein are compositions comprising the disclosed RNAi agents, wherein the compositions further comprise a pharmaceutically acceptable excipient.

Also provided herein are methods for inhibiting expression of a PNPLA3 gene in a cell, the methods comprising introducing into a cell an effective amount of the disclosed RNAi agents or the disclosed compositions.

In some embodiments, the cell is within a subject. In some embodiments, the subject is a human subject.

In other embodiments, the PNPLA3 gene expression is inhibited by at least about 30%. In some embodiments, the PNPLA3 gene expression is inhibited by at least about 50% in the cytoplasm of hepatocytes.

Further provided herein are methods of treating a PNPLA3-related disease or disorder, the methods comprising administering to a human subject in need thereof a therapeutically effective amount of the disclosed compositions.

In some embodiments, the disease is NAFLD, NASH, hepatic fibrosis, alcoholic fatty liver disease, or cirrhosis.

In some embodiments, the RNAi agents are administered at a dose of about 0.05 mg/kg to about 5.0 mg/kg of body weight of the human subject.

In other embodiments, the RNAi agent is administered in two or more doses.

Also provided herein are usages of the disclosed RNAi agents or the disclosed compositions, for the treatment of a disease, disorder, or symptom that is mediated at least in part PNPLA3 gene expression.

In some embodiments, the symptom is cirrhosis of the liver.

Further provided herein are usages of the disclosed RNAi agents or the disclosed compositions, for the preparation of a pharmaceutical compositions for treating a disease, disorder, or symptom that is mediated at least in part by PNPLA3 gene expression.

In some embodiments, the disease is NAFLD, NASH, hepatic fibrosis, or an alcoholic or non-alcoholic liver disease such as cirrhosis. In some embodiments, the RNAi agent is administered at a dose of about 0.05 mg/kg to about 5.0 mg/kg of body weight of the human subject.

DETAILED DESCRIPTION OF ILLUSTRATIVE EMBODIMENTS

Figure 1:
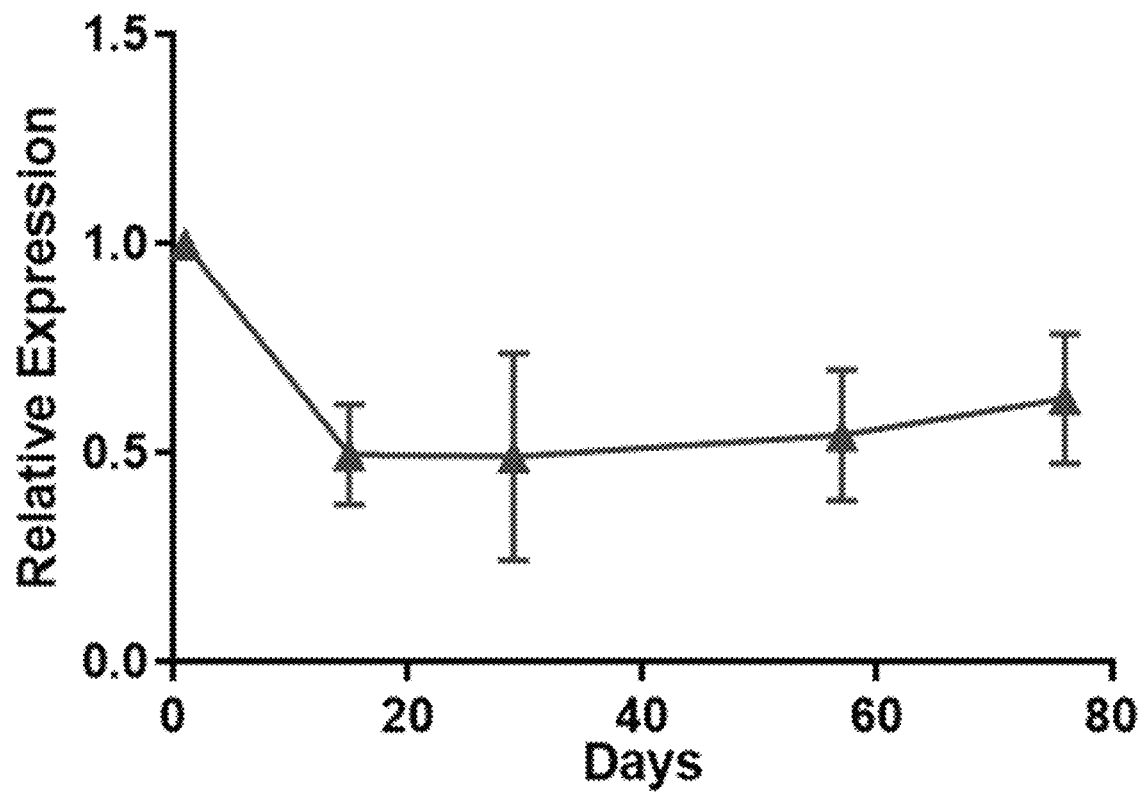
FIG. 1 is a graph depicting the baseline-relative whole liver expression of PNPLA3 by PCR from RNAi agent-treated non-human primates (NHPs). Study #1: Data are geometric mean±SD (n=4).

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

Definitions

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. PNPLA3 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature. A nucleic acid molecule can comprise unmodified and/or modified nucleotides. A nucleotide sequence can comprise unmodified and/or modified nucleotides.

As used herein, a "base," "nucleotide base," "nucleotide," or "nucleobase," is a heterocyclic pyrimidine or purine compound that is a component of a polynucleotide, and includes the primary purine bases adenine and guanine, and the primary pyrimidine bases cytosine, thymine, and uracil. A nucleotide can be unmodified. A nucleotide may further be modified to include, without limitation, universal bases, hydrophobic bases, promiscuous bases, size-expanded bases, and fluorinated bases. (See. e.g., Modified Nucleosides in Biochemistry, Biotechnology and Medicine, Herdewijn, P. ed. Wiley-VCH, 2008). The synthesis of such modified nucleotides (including phosphoramidite compounds that include modified nucleotides) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of a PNPLA3 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "individual", "patient" and "subject", are used interchangeably to refer to a member of any animal species including, but not limited to, birds, humans and other primates, and other mammals including commercially relevant mammals or animal models such as mice, rats, monkeys, cattle, pigs, horses, sheep, cats, and dogs. Preferably, the subject is a human.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol  as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used herein, the terms "comprising," "including," "containing" and "characterized by" are exchangeable, inclusive, open-ended and do not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

DETAILED DESCRIPTION

RNAi Agents

Described herein are RNAi agents for inhibiting expression of a PNPLA3 gene (referred to herein as PNPLA3 RNAi agents or PNPLA3 RNAi triggers). Each PNPLA3 RNAi agent comprises a sense strand and an antisense strand. The sense strand and the antisense strand each can be 16 to 49 nucleotides in length. The sense and antisense strands can be either the same length or they can be different lengths. In some embodiments, the sense and antisense strands are each independently 18 to 27 nucleotides in length. In some embodiments, both the sense and antisense strands are each 21-26 nucleotides in length. In some embodiments, the sense and antisense strands are each 21-24 nucleotides in length. In some embodiments, the sense and antisense strands are each independently 19-21 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, 26, 27, 28, 29, 30, 31, 32, 33, 34, 35, 36, 37, 38, or 39 nucleotides in length. In some embodiments, a double-stranded RNAi agent has a duplex length of about 16, 17, 18, 19, 20, 21, 22, 23 or 24 nucleotides.

Examples of nucleotide sequences used in forming PNPLA3 RNAi agents are provided in Tables 2, 3, and 4. Examples of RNAi agent duplexes, that include the sense strand and antisense strand sequences in Tables 2, 3, and 4, are shown in Tables 5A and 5B.

In some embodiments, the region of perfect, substantial, or partial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the PNPLA3 RNAi agents described herein includes at least 16 consecutive nucleotides that have at least 85% identity to a core stretch sequence (also referred to herein as a "core stretch" or "core sequence") of the same number of nucleotides in a PNPLA3 mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the PNPLA3 mRNA target. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of a PNPLA3 RNAi agent described herein includes at least 16 consecutive nucleotides that have at least 85% complementarity to a core stretch of the same number of nucleotides in a PNPLA3 mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the PNPLA3 mRNA target. In some embodiments, this antisense strand core stretch is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length. A sense strand core stretch sequence can be the same length as a corresponding antisense core sequence or it can be a different length.

The PNPLA3 RNAi agent sense and antisense strands anneal to form a duplex. A sense strand and an antisense strand of a PNPLA3 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of a PNPLA3 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of a PNPLA3 RNAi agent disclosed herein differs by 0, 1, 2, or 3 nucleotides from any of the antisense strand sequences in Table 2 or Table 3. In some embodiments, the sense strand of a PNPLA3 RNAi agent disclosed herein differs by 0, 1, 2, or 3 nucleotides from any of the sense strand sequences in Table 2 or Table 4.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the PNPLA3 mRNA. The sense strand additional nucleotides, if present, may or may not be identical to the corresponding sequence in the PNPLA3 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a PNPLA3 RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, a PNPLA3 RNAi agent comprises an antisense strand having a 3' extension of 1, 2, 3, 4, 5, or 6 nucleotides in length. In other embodiments, a PNPLA3 RNAi agent comprises an antisense strand having a 3' extension of 1, 2, or 3 nucleotides in length. In some embodiments, one or more of the antisense strand extension nucleotides comprise nucleotides that are complementary to the corresponding PNPLA3 mRNA sequence. In some embodiments, one or more of the antisense strand extension nucleotides comprise nucleotides that are not complementary to the corresponding PNPLA3 mRNA sequence.

In some embodiments, a PNPLA3 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the PNPLA3 mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a PNPLA3 RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the PNPLA3 mRNA sequence.

Examples of sequences used in forming PNPLA3 RNAi agents are provided in Tables 2, 3, and 4. In some embodiments, a PNPLA3 RNAi agent antisense strand includes a sequence of any of the sequences in Tables 2 or 3. In certain embodiments, a PNPLA3 RNAi agent antisense strand comprises or consists of any one of the modified sequences in Table 3. In some embodiments, a PNPLA3 RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2 or 3. In some embodiments, a PNPLA3 RNAi agent sense strand includes the sequence of any of the sequences in Tables 2 or 4. In some embodiments, a PNPLA3 RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2 or 4. In certain embodiments, a PNPLA3 RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The PNPLA3 RNAi agents disclosed herein may also be comprised of one or more modified nucleotides. In some embodiments, substantially all of the nucleotides of the sense strand and substantially all of the nucleotides of the antisense strand of the PNPLA3 RNAi agent are modified nucleotides. The PNPLA3 RNAi agents disclosed herein may further be comprised of one or more modified internucleoside linkages, e.g., one or more phosphorothioate linkages. In some embodiments, a PNPLA3 RNAi agent contains one or more modified nucleotides and one or more modified internucleoside linkages. In some embodiments, a 2'-modified nucleotide is combined with modified internucleoside linkage.

In some embodiments, a PNPLA3 RNAi agent is prepared or provided as a salt, mixed salt, or a free-acid. In some embodiments, a PNPLA3 RNAi agent is prepared as a sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administering of the oligonucleotide construct.

In some embodiments, a PNPLA3 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides, 2'-fluoro nucleotides (also referred to herein as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single PNPLA3 RNAi agent or even in a single nucleotide thereof. The PNPLA3 RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and O-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See. e.g., U.S. Pat. No. 5,998,203). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

Modified Internucleoside Linkages

In some embodiments, one or more nucleotides of a PNPLA3 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a PNPLA3 RNAi agent can contain 1, 2, 3, 4, 5, or 6 phosphorothioate linkages, an antisense strand of a PNPLA3 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a PNPLA3 RNAi agent can contain 1, 2, 3, or 4 phosphorothioate linkages, an antisense strand of a PNPLA3 RNAi agent can contain 1, 2, 3, or 4 phosphorothioate linkages, or both the sense strand and the antisense strand independently can contain 1, 2, 3, or 4 phosphorothioate linkages.

In some embodiments, a PNPLA3 RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkages are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a PNPLA3 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a PNPLA3 RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues. (See, e.g., F. Czaudema, Nucleic Acids Res., 2003, 31(11), 2705-16).

Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 6 below.

PNPLA3 RNAi Agents

The PNPLA3 RNAi agents disclosed herein are designed to target specific positions on a PNPLA3 gene (e.g., SEQ ID NO: 1).

NM_025225.2 *Homo sapiens* Patatin Like Phospholipase Domain Containing 3 (PNPLA3), mRNA (SEQ ID NO: 1):

ATGGTCCGAGGGGGCGGGGCTGACGTCGCGCTGGGAATGCCCTGGCCGA

GACACTGAGGCAGGGTAGAGAGCGCTTGCGGGCGCCGGGCGGAGCTGCTG

CGGATCAGGACCCGAGCCGATTCCCGATCCCGACCCAGATCCTAACCCGC

GCCCCCGCCCCGCCGCCGCCGCCATGTACGACGCAGAGCGCGGCTGGAGC

TTGTCCTTCGCGGGCTGCGGCTTCCTGGGCTTCTACCACGTCGGGGCGAC

CCGCTGCCTGAGCGAGCACGCCCCGCACCTCCTCCGCGACGCGCGCATGT

TGTTCGGCGCTTCGGCCGGGCGTTGCACTGCGTCGGCGTCCTCTCCGGT

ATCCCGCTGGAGCAGACTCTGCAGGTCCTCTCAGATCTTGTGCGGAAGGC

CAGGAGTCGGAACATTGGCATCTTCCATCCATCCTTCAACTTAAGCAAGT

TCCTCCGACAGGGTCTCTGCAAATGCCTCCCGGCCAATGTCCACCAGCTC

ATCTCCGGCAAAATAGGCATCTCTCTTACCAGAGTGTCTGATGGGGAAAA

CGTTCTGGTGTCTGACTTTCGGTCCAAAGACGAAGTCGTGGATGCCTTGG

TATGTTCCTGCTTCATCCCCTTCTACAGTGGCCTTATCCCTCCTTCCTTC

AGAGGCGTGCGATATGTGGATGGAGGAGTGAGTGACAACGTACCCTTCAT

TGATGCCAAAACAACCATCACCGTGTCCCCCTTCTATGGGGAGTACGACA

TCTGCCCTAAAGTCAAGTCCACGAACTTTCTTCATGTGGACATCACCAAG

CTCAGTCTACGCCTCTGCACAGGGAACCTCTACCTTCTCTCGAGAGCTTT

TGTCCCCCGGATCTCAAGGTGCTGGGAGAGATATGCCTTCGAGGATATT

TGGATGCATTCAGGTTCTTGGAAGAGAAGGGCATCTGCAACAGGCCCCAG

CCAGGCCTGAAGTCATCCTCAGAAGGGATGGATCCTGAGGTCGCCATGCC

CAGCTGGGCAAACATGAGTCTGGATTCTTCCCCGGAGTCGGCTGCCTTGG

CTGTGAGGCTGGAGGGAGATGAGCTGCTAGACCACCTGCGTCTCAGCATC

CTGCCCTGGGATGAGAGCATCCTGGACACCCTCTCGCCCAGGCTCGCTAC

AGCACTGAGTGAAGAAATGAAAGACAAAGGTGGATACATGAGCAAGATTT

GCAACTTGCTACCCATTAGGATAATGTCTTATGTAATGCTGCCCTGTACC

CTGCCTGTGGAATCTGCCATTGCGATTGTCCAGAGACTGGTGACATGGCT

TCCAGATATGCCCGACGATGTCCTGTGGTTGCAGTGGGTGACCTCACAGG

TGTTCACTCGAGTGCTGATGTGTCTGCTCCCCGCCTCCAGGTCCCAAATG

CCAGTGAGCAGCCAACAGGCCTCCCCATGCACACCTGAGCAGGACTGGCC

CTGCTGGACTCCCTGCTCCCCAAGGGCTGTCCAGCAGAGACCAAAGCAG

AGGCCACCCCGCGGTCCATCCTCAGGTCCAGCCTGAACTTCTTCTTGGGC

AATAAAGTACCTGCTGGTGCTGAGGGGCTCTCCACCTTTCCCAGTTTTTC

ACTAGAGAAGAGTCTGTGAGTCACTTGAGGAGGCGAGTCTAGCAGATTCT

TTCAGAGGTGCTAAAGTTTCCCATCTTTGTGCAGCTACCTCCGCATTGCT

GTGTAGTGACCCCTGCCTGTGACGTGGAGGATCCCAGCCTCTGAGCTGAG

TTGGTTTTATGAAAAGCTAGGAAGCAACCTTTCGCCTGTGCAGCGGTCCA

GCACTTAACTCTAATACATCAGCATGCGTTAATTCAGCTGGTTGGGAAAT

GACACCAGGAAGCCCAGTGCAGAGGGTCCCTTACTGACTGTTTCGTGGCC

CTATTAATGGTCAGACTGTTCCAGCATGAGGTTCTTAGAATGACAGGTGT

TTGGATGGGTGGGGCCTTGTGATGGGGGGTAGGCTGGCCCATGTGTGAT

CTTGTGGGTGGAGGGAAGAGAATAGCATGATCCCACTTCCCCATGCTGT

GGGAAGGGGTGCAGTTCGTCCCCAAGAACGACACTGCCTGTCAGGTGGTC

TGCAAAGATGATAACCTTGACTACTAAAAACGTCTCCATGGCGGGGTAA

CAAGATGATAATCTACTTAATTTTAGAACACCTTTTTCACCTAACTAAAA

TAATGTTTAAAGAGTTTTGTATAAAAATGTAAGGAAGCGTTGTTACCTGT

TGAATTTTGTATTATGTGAATCAGTGAGATGTTAGTAGAATAAGCCTTAA

AAAAAAAAAAATCGGTTGGGTGCAGTGGCACACGGCTGTAATCCCAGCAC

TTTGGGAGGCCAAGGTTGGCAGATCACCTGAGGTCAGGAGTTCAAGACCA

GTCTGGCCAACATAGCAAAACCCTGTCTCTACTAAAAATACAAAAATTAT

CTGGGCATGGTGGTGCATGCCTGTAATCCCAGCTATTCGGAAGGCTGAGG

CAGGAGAATCACTTGAACCCAGGAGGCGGAGGTTGCGGTGAGCTGAGATT

GCACCATTTCATTCCAGCCTGGGCAACATGAGTGAAAGTCTGACTCAAAA

-continued

AAAAAAAATTTAAAAAACAAAATAATCTAGTGTGCAGGGCATTCACCTCA

GCCCCCCAGGCAGGAGCCAAGCACAGCAGGAGCTTCCGCCTCCTCTCCAC

TGGAGCACACAACTTGAACCTGGCTTATTTTCTGCAGGGACCAGCCCAC

ATGGTCAGTGAGTTTCTCCCCATGTGTGGCGATGAGAGAGTGTAGAAATA

AAGAC

As defined herein, an antisense strand sequence is designed to target a PNPLA3 gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target a PNPLA3 gene at position 2180 requires that when base pairing to the gene, the 5' terminal nucleobase of the antisense strand is aligned with position 2198 of the PNPLA3 gene.

As provided herein, a PNPLA3 RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a PNPLA3 RNAi agent disclosed herein that is designed to target position 2180 of a PNPLA3 gene, the 5' terminal nucleobase of the antisense strand of the of the PNPLA3 RNAi agent must be aligned with position 2198 of the gene; however, the 5' terminal nucleobase of the antisense strand may be, but is not required to be, complementary to position 2200 of a PNPLA3 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the PNPLA3 RNAi agent (e.g., whether the PNPLA3 RNAi agent is designed to target a PNPLA3 gene at position 2180, at position 1586, at position 1179, or at some other position) is important to the level of inhibition achieved by the PNPLA3 RNAi agent.

In some embodiments, the PNPLA3 RNAi agents disclosed herein target a PNPLA3 gene at or near the positions of the PNPLA3 gene sequence shown in Table 1. In some embodiments, the antisense strand of a PNPLA3 RNAi agent disclosed herein includes a core stretch sequence that is fully, substantially, or at least partially complementary to a target PNPLA3 19-mer sequence disclosed in Table 1.

TABLE 1

PNPLA3 19-mer mRNA Target Sequences (taken from homo sapiens patatin like phospholipase domain containing 3 (PNPLA3), mRNA, GenBank NM_025225.2 (SEQ ID NO: 1))[1]

| SEQ ID No. | PNPLA3 19-mer Target Sequences (5' → 3') | Corresponding Positions of Sequence on SEQ ID NO: 1 | Targeted Gene Position (as referred to herein) |
|---|---|---|---|
| 2 | ACCUUUUUCACCUAACUAA | 2180-2198 | 2180 |
| 3 | CUUUCCCAGUUUUUCACUA | 1586-1604 | 1586 |
| 4 | GGUGGAUACAUGAGCAAGA | 1179-1197 | 1179 |
| 5 | GGUCCAAAGACGAAGUCGU | 571-589 | 571 |
| 6 | AACGUACCCUUCAUUGAUG | 687-705 | 687 |
| 7 | CUGAGUUGGUUUUAUGAAA | 1746-1764 | 1746 |
| 8 | AGCAAGAUUUGCAACUUGC | 1191-1209 | 1191 |

[1]When referring to gene positions herein, Applicant uses Genebank NM_025225.2 as the reference gene for human PNPLA3. On or about Feb. 9, 2020, the gene sequence was updated as NM_025225.3. While referencing the updated gene would change the number identified as the "Targeted Gene Position" in Table 1 above, this has no impact on the nucleotide sequences used in the RNAi agents disclosed here.

In some embodiments, a PNPLA3 RNAi agent includes an antisense strand wherein position 19 of the antisense strand (5'→3') is capable of forming a base pair with position 1 of a 19-mer target sequence disclosed in Table 1. In some embodiments, a PNPLA3 RNAi agent includes an antisense strand wherein position 1 of the antisense strand (5'→3') is capable of forming a base pair with position 19 of the 19-mer target sequence disclosed in Table 1.

In some embodiments, a PNPLA3 RNAi agent includes an antisense strand wherein position 2 of the antisense strand (5'→3') is capable of forming a base pair with position 18 of the 19-mer target sequence disclosed in Table 1. In some embodiments, a PNPLA3 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the PNPLA3 gene, or can be non-complementary to the PNPLA3 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a PNPLA3 RNAi agent antisense strand comprises the sequence of nucleotides (from 5' end→3' end) 2-18, 2-19, 2-20, or 2-21 of any of the antisense strand sequences in Table 2 or Table 3. In some embodiments, a PNPLA3 RNAi sense strand comprises the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences in Table 2 or Table 4.

In some embodiments, a PNPLA3 RNAi agent antisense strand comprises the sequence of nucleotides (from 5' end→3' end) 2-18, 2-19, 2-20, or 2-21 of any of the antisense strand sequences of SEQ ID NOs: 46-60, 176, 181 and 188. In some embodiments, a PNPLA3 RNAi sense strand comprises the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences of SEQ ID NOs: 2, 3, 4, 9-20, 214, 219 and 220.

In some embodiments, a PNPLA3 RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences in Table 2 or Table 4.

In some embodiments, a PNPLA3 RNAi agent is comprised of (i) an antisense strand comprising the sequence of nucleotides (from 5' end→3' end) 2-18 or 2-19 of any of the antisense strand sequences of SEQ ID NOs: 46-60, 176, 181 and 188, and (ii) a sense strand comprising the sequence of nucleotides (from 5' end→3' end) 3-21, 2-21, 1-21, 3-20, 2-20, 1-20, 3-19, 2-19, 1-19, 3-18, 2-18, or 1-18 of any of the sense strand sequences of SEQ ID NOs: 2, 3, 4, 9-20, 214, 219 and 220.

In some embodiments, the PNPLA3 RNAi agents include core 19-mer nucleotide sequences shown in the following Table 2.

TABLE 2

PNPLA3 RNAi Agent Antisense Strand and Sense Strand Core Stretch Base Sequences
(N = any nucleobase; I = hypoxanthine (inosine nucleotide; ($A^{2N}$) = 2-aminoadenine nucleotide

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 46 | UUAGUUAGGUGAAAAAGGU | 2 | ACCUUUUUCACCUAACUAA | 2180-2198 | 2180 |
| 47 | NUAGUUAGGUGAAAAAGGU | 9 | ACCUUUUUCACCUAACUAN | 2180-2198 | 2180 |
| 48 | NUAGUUAGGUGAAAAAGGN | 10 | NCCUUUUUCACCUAACUAN | 2180-2198 | 2180 |
| 49 | UUAGUUAGGUGAAAAAGGU | 11 | ACCUUUUUCACCUAACU($A^{2N}$)A | 2180-2198 | 2180 |
| 50 | NUAGUUAGGUGAAAAAGGU | 12 | ACCUUUUUCACCUAACU($A^{2N}$)N | 2180-2198 | 2180 |
| 51 | NUAGUUAGGUGAAAAAGGN | 13 | NCCUUUUUCACCUAACU($A^{2N}$)N | 2180-2198 | 2180 |
| 52 | UAGUGAAAAACUGGGAAAG | 3 | CUUUCCCAGUUUUUCACUA | 1586-1604 | 1586 |
| 53 | NAGUGAAAAACUGGGAAAG | 14 | CUUUCCCAGUUUUUCACUN | 1586-1604 | 1586 |
| 54 | NAGUGAAAAACUGGGAAAN | 15 | NUUUCCCAGUUUUUCACUN | 1586-1604 | 1586 |
| 55 | UCUUGCUCAUGUAUCCACC | 4 | GGUGGAUACAUGAGCAAGA | 1179-1197 | 1179 |
| 56 | NCUUGCUCAUGUAUCCACC | 16 | GGUGGAUACAUGAGCAAGN | 1179-1197 | 1179 |
| 57 | NCUUGCUCAUGUAUCCACN | 17 | NGUGGAUACAUGAGCAAGN | 1179-1197 | 1179 |
| 58 | UCUUGCUCAUGUAUCCACC | 18 | GGUGGAUACAUGAICAAGA | 1179-1197 | 1179 |
| 59 | NCUUGCUCAUGUAUCCACC | 19 | GGUGGAUACAUGAICAAGN | 1179-1197 | 1179 |
| 60 | NCUUGCUCAUGUAUCCACN | 20 | NGUGGAUACAUGAICAAGN | 1179-1197 | 1179 |
| 61 | ACGACUUCGUCUUUGGACC | 5 | GGUCCAAAGACGAAGUCGU | 571-589 | 571 |
| 62 | UCGACUUCGUCUUUGGACC | 21 | GGUCCAAAGACGAAGUCGA | 571-589 | 571 |
| 63 | NCGACUUCGUCUUUGGACC | 22 | GGUCCAAAGACGAAGUCGN | 571-589 | 571 |
| 64 | NCGACUUCGUCUUUGGACN | 23 | NGUCCAAAGACGAAGUCGN | 571-589 | 571 |
| 65 | ACGACUUCGUCUUUGGACC | 24 | GGUCCAAAGACGAAGUCIU | 571-589 | 571 |
| 66 | UCGACUUCGUCUUUGGACC | 25 | GGUCCAAAGACGAAGUCIA | 571-589 | 571 |
| 67 | NCGACUUCGUCUUUGGACC | 26 | GGUCCAAAGACGAAGUCIN | 571-589 | 571 |
| 68 | NCGACUUCGUCUUUGGACN | 27 | NGUCCAAAGACGAAGUCIN | 571-589 | 571 |
| 69 | ACGACUUCGUCUUUGGACC | 28 | GGUCCAAAGACIAAGUCIU | 571-589 | 571 |
| 70 | UCGACUUCGUCUUUGGACC | 29 | GGUCCAAAGACIAAGUCIA | 571-589 | 571 |
| 71 | NCGACUUCGUCUUUGGACC | 30 | GGUCCAAAGACIAAGUCIN | 571-589 | 571 |
| 72 | NCGACUUCGUCUUUGGACN | 31 | NGUCCAAAGACIAAGUCIN | 571-589 | 571 |
| 73 | ACGACUUCGUCUUUGGACC | 32 | GGUCCAAAGACGAAIUCGU | 571-589 | 571 |

TABLE 2-continued

PNPLA3 RNAi Agent Antisense Strand and Sense Strand Core Stretch Base Sequences
(N = any nucleobase; I = hypoxanthine (inosine nucleotide; (A$^{2N}$) = 2-aminoadenine nucleotide

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 74 | UCGACUUCGUCUUUGGACC | 33 | GGUCCAAAGACGAAIUCGA | 571-589 | 571 |
| 75 | NCGACUUCGUCUUUGGACC | 34 | GGUCCAAAGACGAAIUCGN | 571-589 | 571 |
| 76 | NCGACUUCGUCUUUGGACN | 35 | NGUCCAAAGACGAAIUCGN | 571-589 | 571 |
| 257 | CAUCAAUGAAGGGUACGUU | 6 | AACGUACCCUUCAUUGAUG | 687-705 | 687 |
| 78 | UAUCAAUGAAGGGUACGUU | 36 | AACGUACCCUUCAUUGAUA | 687-705 | 687 |
| 77 | NAUCAAUGAAGGGUACGUU | 37 | AACGUACCCUUCAUUGAUN | 687-705 | 687 |
| 79 | NAUCAAUGAAGGGUACGUN | 38 | NACGUACCCUUCAUUGAUN | 687-705 | 687 |
| 258 | UUUCAUAAAACCAACUCAG | 7 | CUGAGUUGGUUUUAUGAAA | 1746-1764 | 1746 |
| 80 | NUUCAUAAAACCAACUCAG | 39 | CUGAGUUGGUUUUAUGAAN | 1746-1764 | 1746 |
| 81 | NUUCAUAAAACCAACUCAN | 40 | NUGAGUUGGUUUUAUGAAN | 1746-1764 | 1746 |
| 82 | GCAAGUUGCAAAUCUUGCU | 8 | AGCAAGAUUUGCAACUUGC | 1191-1209 | 1191 |
| 83 | UCAAGUUGCAAAUCUUGCU | 41 | AGCAAGAUUUGCAACUUGA | 1191-1209 | 1191 |
| 84 | UCAAGUUGCAAAUCUUGCG | 42 | CGCAAGAUUUGCAACUUGA | 1191-1209 | 1191 |
| 85 | NCAAGUUGCAAAUCUUGCU | 43 | AGCAAGAUUUGCAACUUGN | 1191-1209 | 1191 |
| 86 | NCAAGUUGCAAAUCUUGCG | 44 | CGCAAGAUUUGCAACUUGN | 1191-1209 | 1191 |
| 87 | NCAAGUUGCAAAUCUUGCN | 45 | NGCAAGAUUUGCAACUUGN | 1191-1209 | 1191 |

The PNPLA3 RNAi agent sense strands and antisense strands that comprise or consist of the sequences in Table 2 can be modified nucleotides or unmodified nucleotides. In some embodiments, the PNPLA3 RNAi agents having the sense and antisense strand sequences that comprise or consist of the sequences in Table 2 are all or substantially all modified nucleotides.

In some embodiments, the antisense strand of a PNPLA3 RNAi agent disclosed herein differs by 0, 1, 2, or 3 nucleotides from any of the antisense strand sequences in Table 2. In some embodiments, the antisense strand of a PNPLA3 RNAi agent disclosed herein differs by 0, 1, 2, or 3 nucleotides from any of the antisense strand sequences of SEQ ID NOs: 46-60, 176, 181 and 188. In some embodiments, the sense strand of a PNPLA3 RNAi agent disclosed herein differs by 0, 1, 2, or 3 nucleotides from any of the sense strand sequences in Table 2. In some embodiments, the sense strand of a PNPLA3 RNAi agent disclosed herein differs by 0, 1, 2, or 3 nucleotides from any of the sense strand sequences of SEQ ID NOs: 2, 3, 4, 9-20, 214, 219 and 220.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand.

In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified PNPLA3 RNAi agent antisense strands, as well as their underlying unmodified nucleobase sequences, are provided in Table 3. Certain modified PNPLA3 RNAi agent sense strands, as well as their underlying unmodified nucleobase sequences, are provided in Table 4. In forming PNPLA3 RNAi agents, each of the nucleotides in each of the underlying base sequences listed in Tables 3 and 4, as well as in Table 2, above, can be a modified nucleotide.

The PNPLA3 RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, a PNPLA3 RNAi agent antisense strand comprises a nucleotide sequence of any of the sequences in Table 2 or Table 3.

In some embodiments, a PNPLA3 RNAi agent comprises or consists of a duplex having the nucleobase sequences of the sense strand and the antisense strand of any of the sequences in Table 2, Table 3 or Table 4. In some embodiments, a PNPLA3 RNAi agent comprises or consists of a duplex sequence with SEQ ID NOs: (176 and 214); (90 and 131); (181 and 219); (95 and 136); (188 and 220) and/or (102 and 137). In some embodiments, the PNPLA3 RNAi agent duplex sequence comprising SEQ ID NOs: (176 and 214); (90 and 131); (181 and 219); (95 and 136); (188 and 220) or (102 and 137) are prepared or provided as a sodium salt, mixed salt, or a free-acid.

Examples of antisense strands containing modified nucleotides are provided in Table 3. Examples of sense strands containing modified nucleotides are provided in Table 4.

As used in Tables 3 and 4, the following notations are used to indicate modified nucleotides and linking groups:

A=adenosine-3'-phosphate;
C=cytidine-3'-phosphate;
G=guanosine-3'-phosphate;
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
i=2'-O-methylinosine-3'-phosphate
is =2'-O-methylinosine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
AUNA=2',3'-seco-adenosine-3'-phosphate, see Table 6
AUNAS=2',3'-seco-adenosine-3'-phosphorothioate, see Table 6
CUNA=2',3'-seco-cytidine-3'-phosphate, see Table 6
CUNAS=2',3'-seco-cytidine-3'-phosphorothioate, see Table 6
GUNA=2',3'-seco-guanosine-3'-phosphate, see Table 6
GUNAS=2',3'-seco-guanosine-3'-phosphorothioate, see Table 6
UUNA=2',3'-seco-uridine-3'-phosphate, see Table 6
UUNAS=2',3'-seco-uridine-3'-phosphorothioate, see Table 6
a_2N=2'-O-methyl-2-aminoadenosine-3'-phosphate, see Table 6
a_2Ns=2'-O-methyl-2-aminoadenosine-3'-phosphorothioate, see Table 6
(invAb)=inverted abasic deoxyribonucleotide, see Table 6
(invAb)s=inverted abasic deoxyribonucleotide-5'-phosphorothioate, see Table 6

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see. e.g., Table 6). Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the PNPLA3 RNAi agents and compositions of PNPLA3 RNAi agents disclosed herein.

Certain examples of targeting ligands, targeting groups, and linking groups used with the PNPLA3 RNAi agents disclosed herein are provided below in Table 6. More specifically, targeting groups and linking groups (which together can form a targeting ligand) include (NAG37) and (NAG37)s, for which their chemical structures are provided below in Table 6. Each sense strand and/or antisense strand can have any targeting ligands, targeting groups, or linking groups listed herein, as well as other groups, conjugated to the 5' and/or 3' end of the sequence.

TABLE 3

PNPLA3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| J1M00002-AS | usCfsasUfcAfaUfgAfaGfgGfuAfcGfuUfsg | 88 | UCAUCAAUGAAGGGUACGUUG | 174 |
| J1M00004-AS | usCfsasUfcAfaUfgAfaGfgGfuAfcGfuCfsg | 89 | UCAUCAAUGAAGGGUACGUCG | 175 |
| J1M00006-AS | usAfsgsUfgAfaAfaAfcUfgGfgAfaAfgGfsu | 90 | UAGUGAAAACUGGGAAAGGU | 176 |
| J1M00008-AS | usAfsgsUfgAfaAfaAfcUfgGfgAfaAfgGfsg | 91 | UAGUGAAAACUGGGAAAGGG | 177 |
| J1M00010-AS | asAfsasUfcUfuGfcUgcAfuGfuAfuCfcAfsc | 92 | AAAUCUUGCUCAUGUAUCCAC | 178 |

TABLE 3-continued

PNPLA3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| J1M00012-AS | usAfscsUfuGfaCfuUfuAfgGfgCfaGfaUfsg | 93 | UACUUGACUUUAGGGCAGAUG | 179 |
| J1M00014-AS | usAfscsUfuGfaCfuUfuAfgGfgCfaGfaCfsg | 94 | UACUUGACUUUAGGGCAGACG | 180 |
| J1M00016-AS | usUfsasGfuUfaGfuGfAfaAfaAfgGfuGfsu | 95 | UUAGUUAGGUGAAAAGGUGU | 181 |
| J1M00020-AS | usCfsusUfgCfuCfaUfgUfaUfcCgaCgcUfsg | 96 | UCUUGCUCAUGUAUCCACCUG | 182 |
| J1M00023-AS | asCfsgsAfcUfuCfgUfcUfuUfgGfaCfcGfsa | 97 | ACGACUUCGUCUUUGGACCGA | 183 |
| J1M00025-AS | usAfsusCgaAfuGfaAfgGfgUfaCfgUfuGfsg | 98 | UAUCAAUGAAGGGUACGUUGG | 184 |
| J1M00027-AS | usCfscsAfaAfuAfuCfcUfcGfaAfgGfcAfsg | 99 | UCCAAAUAUCCUCGAAGGCAG | 185 |
| J1M00029-AS | usUfsgsAfaAfaAfcUfgGfgAfaAfgGfuGfsg | 100 | UUGAAAACUGGGAAAGGUGG | 186 |
| J1M00031-AS | usUfscsAfuAfaAfaCfcAfaCfuCfaGfcUfsc | 101 | UUCAUAAAACCAACUCAGCUC | 187 |
| J1M00032-AS | usCfsusUfgCfU$_{UNA}$CfaUfgUfaUfcCfaCfcUfsg | 102 | UCUUGCUCAUGUAUCCACCUG | 188 |
| J1M00034-AS | asGfsasAfcGfU$_{UNA}$UfuUfcCfcCfaUfcAfgAfsc | 103 | AGAACGUUUCCCCAUCAGAC | 189 |
| J1M00036-AS | asGfsasAfcGfU$_{UNA}$UfuUfcCfcCfaUfcAfgusu | 104 | AGAACGUUUCCCCAUCAGUU | 190 |
| J1M00038-AS | usAfscsAfcCfagaacGfuUfuUfcCgcCfsa | 105 | UACACCAGAACGUUUUCCCCA | 191 |
| J1M00040-AS | usGfsasAfaGfU$_{UNA}$CfaGfaCfaCfcAfgAfaCfsg | 106 | UGAAAGUCAGACACCAGAACG | 192 |
| J1M00042-AS | usAfsasGfgGfU$_{UNA}$AfcGfuUfgUfcAgcUfcAfsc | 107 | UAAGGGUACGUUGUCACUCAC | 193 |
| J1M00046-AS | usAfscsUfuUfagggcAfgAfuGfuCfgUfsg | 108 | UACUUUAGGGCAGAUGUCGUG | 194 |
| J1M00050-AS | usGfsusAfgCfaAfgUfuGfcAfaAfuCfuCfsg | 109 | UGUAGCAAGUUGCAAAUCUCG | 195 |
| J1M00052-AS | asCfsgsAfcUfU$_{UNA}$CfgUfcUfuUfgGfaCfcGfsa | 110 | ACGACUUCGUCUUUGGACCGA | 196 |
| J1M00057-AS | asCfsasAfgAfuCfuGfaGfaGfgAfcCfuGfsc | 111 | ACAAGAUCUGAGAGGACCUGC | 197 |
| J1M00059-AS | usCfsasAfuGfaAfgGfgUfaCfgUfuGfuCfsg | 112 | UCAAUGAAGGGUACGUUGUCG | 198 |
| J1M00063-AS | asAfsusCfuUfgCfuCfaUfgUfaUfcCfaCfsc | 113 | AAUCUUGCUCAUGUAUCCACC | 199 |
| J1M00072-AS | usUfsgsUfcAfuUfcCfcCfaAfcCfaGfcUfsg | 114 | UUGUCAUUUCCCAACCAGCUG | 200 |
| J1M00074-AS | usAfsgsUfgAfaAfaAfcUfgGfgAfaAfgGfsc | 115 | UAGUGAAAACUGGGAAAGGC | 201 |
| J1M00077-AS | usCfsusUfgCfuCfaUfgUfaUfcCfaCfcUfsu | 116 | UCUUGCUCAUGUAUCCACCUU | 202 |
| J1M00079-AS | usCfsusUfgCfuCfaUfgUfaUfcCfaCfcUfsc | 117 | UCUUGCUCAUGUAUCCACCUC | 203 |
| J1M00082-AS | usUfsasGfuUfaGfuGfaAfaAfaAfgGfuGfsc | 118 | UUAGUUAGGUGAAAAGGUGC | 204 |
| J1M00113-AS | cPrpusUfsasGfuUfaGfuGfUfgAfaAfaAfgGfuGfsu | 119 | UUAGUUAGGUGAAAAGGUGU | 205 |
| J1M00114-AS | usUfsasGfuU$_{UNA}$aGfuGfUfgAfaAfaAfgGfuGfsu | 120 | UUAGUUAGGUGAAAAGGUGU | 205 |
| J1M00115-AS | usUfsasGfuUfA$_{UNA}$GfgUfgAfaAfaAfgGfuGfsu | 121 | UUAGUUAGGUGAAAAGGUGU | 205 |
| J1M00116-AS | usUfsasGfuUfaG$_{UNA}$gUfgAfaAfaAfgGfuGfsu | 122 | UUAGUUAGGUGAAAAGGUGU | 205 |
| J1M00121-AS | asUfscsCfaAfaUfaUfcCfuCfgAfaGfcAfsa | 123 | AUCCAAAUAUCCUCGAAGGCA | 206 |
| J1M00123-AS | usCfsasUfgUfaUfcCfaCfcUfuUfgUfcUfsu | 124 | UCAUGUAUCCACCUUUGUCUU | 207 |
| J1M00125-AS | usGfscsAfaAfuCfuUfgCfuCfaUfgUfaUfsc | 125 | UGCAAAUCUUGCUCAUGUAUC | 208 |
| J1M00127-AS | usCfsasAfgUfuGfcAfaAfuCfuUfgCfuCfsa | 126 | UCAAGUUGCAAAUCUUGCUCA | 209 |
| J1M00129-AS | usCfsasAfgUfuGfcAfaAfuCfuUfgCfuCfsg | 127 | UCAAGUUGCAAAUCUUGCUCG | 210 |
| J1M00133-AS | usUfsusCfaUfaAfaAfgcCfaAfcUfcAfgCfsu | 128 | UUUCAUAAAACCAACUCAGCU | 211 |

TABLE 4

PNPLA3 RNAi Agent Sense Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| J1M00001-SS | (NAG37)s(invAb)scaacguacCfCfUfucauugaugas(invAb) | 129 | CAACGUACCCUUCAUUGAUGA | 212 |
| J1M00003-SS | (NAG37)s(invAb)scgacguacCfCfUfucauugaugas(invAb) | 130 | CGACGUACCCUUCAUUGAUGA | 213 |
| J1M00005-SS | (NAG37)s(invAb)saccuuuccCfAfGfuuuuucacuas(invAb) | 131 | ACCUUUCCCAGUUUUUCACUA | 214 |
| J1M00007-SS | (NAG37)s(invAb)scccuuuccCfAfGfuuuuucacuas(invAb) | 132 | CCCUUUCCCAGUUUUUCACUA | 215 |
| J1M00009-SS | (NSG37)s(invAb)sguggauacAfUfGfagcaagauuus(invAb) | 133 | GUGGAUACAUGAGCAAGAUUU | 216 |
| J1M00011-SS | (NSG37)s(invAb)scaucugccCfUfAfaagucaaguas(invAb) | 134 | CAUCUGCCCUAAAGUCAAGUA | 217 |
| J1M00013-SS | (NSG37)s(invAb)scgucugccCfUfAfaagucaaguas(invAb) | 135 | CGUCUGCCCUAAAGUCAAGUA | 218 |
| J1M00015-SS | (NSG37)s(invAb)sacaccuuuUfUfCfaccuaacuaas(invAb) | 136 | ACACCUUUUUCACCUAACUAA | 219 |
| J1M00019-SS | (NSG37)s(invAb)scagguggaUfAfCfaugagcaagas(invAb) | 137 | CAGGUGGAUACAUGAGCAAGA | 220 |
| J1M00021-SS | (NSG37)s(invAb)scagguggaUfAfCfaugaicaagas(invAb) | 138 | CAGGUGGAUACAUGAICAAGA | 221 |
| J1M00022-SS | (NSG37)s(invAb)sucgguccaAfAfGfacgaagucius(invAb) | 139 | UCGGUCCAAAGACGAAGUCIU | 222 |
| J1M00024-SS | (NSG37)s(invAb)sccaacguaCfCfCfuucauugauas(invAb) | 140 | CCAACGUACCCUUCAUUGAUA | 223 |
| J1M00026-SS | (NSG37)s(invAb)scugccuucGfAfGfgauauuuigas(invAb) | 141 | CUGCCUUCGAGGAUAUUUIGA | 224 |
| J1M00028-SS | (NSG37)s(invAb)sccaccuuuCfCfCfaguuuuucaas(invAb) | 142 | CCACCUUUCCCAGUUUUUCAA | 225 |
| J1M00030-SS | (NSG37)s(invAb)sgagcugagUfUfGfguuuaugaas(invAb) | 143 | GAGCUGAGUUGGUUUAUGAA | 226 |
| J1M00033-SS | (NSG37)s(invAb)sgucugaugGfGfGfaaaacguucus(invAb) | 144 | GUCUGAUGGGGAAAACGUUCU | 227 |
| J1M00035-SS | (NSG37)s(invAb)scugaugGfGfGfaaaacguucuuus(invAb) | .45 | CUGAUGGGGAAAACGUUCUUU | 228 |
| J1M00037-SS | (NSG37)s(invAb)suggggaaaAfCfGfuucugiuguas(invAb) | 146 | UGGGGAAAACGUUCUGIUGUA | 229 |
| J1M00039-SS | (NSG37)s(invAb)scguucugguUfGfUfcugacuuucas(invAb) | 147 | CGUUCGGUGUCUGACUUUCA | 230 |
| J1M00041-SS | (NSG37)s(invAb)sgugagugaCfAfAfcguacccuuas(invAb) | 148 | GUGAGUGACAACGUACCCUUA | 231 |
| J1M00045-SS | (NSG37)s(invAb)scacgacauCfUfGfcccuaaaguas(invAb) | 149 | CACGACAUCUGCCCUAAAGUA | 232 |
| J1M00049-SS | (NSG37)s(invAb)scgagauuuGfCfAfacuuicuacas(invAb) | 150 | CGAGAUUUGCAACUUICUACA | 233 |
| J1M00051-SS | (NSG37)s(invAb)sucgguccaAfAfGfacgaagucgus(invAb) | 151 | UCGGUCCAAAGACGAAGUCGU | 234 |
| J1M00053-SS | (NSG37)s(invAb)sucgguccaAfAfGfacgaaiucgus(invAb) | 152 | UCGGUCCAAAGACGAAIUCGU | 235 |
| J1M00054-SS | (NSG37)s(invAb)sccaccuuuUfUfCfaccuaacua_2Nas(invAb) | 153 | CCACCUUUUUCACCUAACU(A$^{2N}$)A | 236 |
| J1M00056-SS | (NSG37)s(invAb)sgcagiuccUfCfUfcagaucuugus(invAb) | 154 | GCAGIUCCUCUCAGAUCUUGU | 237 |
| J1M00058-SS | (NSG37)s(invAb)scgacaacgUfAfCfccuucauugas(invAb) | 155 | CGACAACGUACCCUUCAUUGA | 238 |
| J1M00062-SS | (NSG37)s(invAb)sgguggauaCfAfUfgagcaagauus(invAb) | 156 | GGUGGAUACAUGAGCAAGAUU | 239 |
| J1M00071-SS | (NSG37)s(invAb)scagcugguUfGfGfgaaaugacaas(invAb) | 157 | CAGCUGGUUGGGAAAUGACAA | 240 |
| J1M00073-SS | (NSG37)s(invAb)sgccuuuccCfAfGfuuuuucacuas(invAb) | 158 | GCCUUUCCCAGUUUUUCACUA | 241 |
| J1M00076-SS | (NSG37)s(invAb)saaagguggaUfAfCfaugaicaagas(invAb) | 159 | AAGGUGGAUACAUGAICAAGA | 242 |
| J1M00078-SS | (NSG37)s(invAb)sgagguggaUfAfCfaugaicaagas(invAb) | 160 | GAGGUGGAUACAUGAICAAGA | 243 |
| J1M00080-SS | (NSG37)s(invAb)sa_2NagguggaUfAfCfaugaicaagas(invAb) | 161 | (A$^{2N}$)AGGUGGAUACAUGAICAAGA | 244 |
| J1M00081-SS | (NSG37)s(invAb)sgcaccuuuUfUfCfaccuaacuaas(invAb) | 162 | GCACCUUUUUCACCUAACUAA | 245 |
| J1M00083-SS | (NSG37)s(invAb)sgcaccuuuUfUfCfaccuaacua_2Nas(invAb) | 163 | GCACCUUUUUCACCUAACUAA | 246 |
| J1M00084-SS | (NSG37)s(invAb)sa_2NcaccuuuUfUfCfaccuaacuaas(invAb) | 164 | (A$^{2N}$)CACCUUUUUCACCUAACUAA | 247 |
| J1M00117-SS | (NSG37)s(invAb)sacaccuuuUfUfCfaccuaacua_2Nas(invAb) | 165 | ACACCUUUUUCACCUAACU(A$^{2N}$)A | 248 |

TABLE 4-continued

PNPLA3 RNAi Agent Sense Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| J1M00118-SS | (NSG37)s(invAb)sa_2NcaccuuuUfUfCfaccuaacua_2Nas(invAb) | 166 | ($A^{2N}$)CACCUUUUCACCUAACUAA | 249 |
| J1M00119-SS | (NSG37)s(invAb)sacAfcCfuUfuUfUfCfaccuaacuaas(invAb) | 167 | ACACCUUUUCACCUAACUAA | 250 |
| J1M00120-SS | (NSG37)s(invAb)sugccuucgAfGfGfauauuuggaus(invAb) | 168 | UGCCUUCGAGGAUAUUUGGAU | 251 |
| J1M00122-SS | (NSG37)s(invAb)sa_2NagacaaaGfGfUfggauacaugas(invAb) | 169 | ($A^{2N}$)AGACAAAGGUGGAUACAUGA | 252 |
| J1M00124-SS | (NSG37)s(invAb)sga_2NuacaugAfGfCfaagauuugcas(invAb) | 170 | G($A^{2N}$)UACAUGAGCAAGAUUUGCA | 253 |
| J1M00126-SS | (NSG37)s(invAb)sugagcaaAfuUfUfugcaacuugas(invAb) | 171 | UGAGCAAGAUUUGCAACUUGA | 254 |
| J1M00128-SS | (NSG37)s(invAb)scgagcaagAfUfUfugcaacuugas(invAb) | 172 | CGAGCAAGAUUUGCAACUUGA | 255 |
| J1M00132-SS | (NSG37)s(invAb)sagcugaguUfGfGfuuuuaugaaas(invAb) | 173 | AGCUGAGUUGGUUUUAUGAAA | 256 |

($A^{2N}$) = 2-aminoadenine nucleotide;
I = hypoxanthine (inosine) nucleotide

The PNPLA3 RNAi agents described herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of a PNPLA3 RNAi agent disclosed herein differs by 0, 1, 2, or 3 nucleotides from any of the antisense strand sequences in Table 3. In some embodiments, the sense strand of a PNPLA3 RNAi agent disclosed herein differs by 0, 1, 2, or 3 nucleotides from any of the sense strand sequences in Table 4.

In some embodiments, a PNPLA3 RNAi agent antisense strand comprises a nucleotide sequence of any of the sequences in Table 2 or Table 3. In some embodiments, a PNPLA3 RNAi agent antisense strand comprises the sequence of nucleotides (from 5' end→3' end) 1-17, 2-17, 1-18, 2-18, 1-19, 2-19, 1-20, 2-20, 1-21, or 2-21, of any of the sequences in Table 2 or Table 3. In certain embodiments, a PNPLA3 RNAi agent antisense strand comprises or consists of a modified sequence of any one of the modified sequences in Table 3.

In some embodiments, a PNPLA3 RNAi agent sense strand comprises the nucleotide sequence of any of the sequences in Table 2 or Table 4. In some embodiments, a PNPLA3 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, or 4-21, of any of the sequences in Table 2 or Table 4. In certain embodiments, a PNPLA3 RNAi agent sense strand comprises or consists of a modified sequence of any one of the modified sequences in Table 4.

For the PNPLA3 RNAi agents disclosed herein, the nucleotide at position 1 of the antisense strand (from 5' end→3' end) can be perfectly complementary to a PNPLA3 gene, or can be non-complementary to a PNPLA3 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the PNPLA3 RNAi agent has a sense strand consisting of the modified sequence of any of the modified sequences in Table 4, and an antisense strand consisting of the modified sequence of any of the modified sequences in Table 3. Certain representative sequence pairings are exemplified by the Duplex ID Nos. shown in Tables 5A and 5B.

In some embodiments, a PNPLA3 RNAi agent comprises, consists of, or consists essentially of a duplex represented by any one of the Duplex ID Nos. presented herein. In some embodiments, a PNPLA3 RNAi agent comprises the sense strand and antisense strand nucleotide sequences of any of the duplexes represented by any of the Duplex ID Nos. presented herein. In some embodiments, a PNPLA3 RNAi agent comprises the sense strand and antisense strand nucleotide sequences of any of the duplexes represented by any of the Duplex ID Nos. presented herein and a targeting group and/or linking group wherein the targeting group and/or linking group is covalently linked (i.e., conjugated) to the sense strand or the antisense strand. In some embodiments, a PNPLA3 RNAi agent includes the sense strand and antisense strand modified nucleotide sequences of any of the Duplex ID Nos. presented herein. In some embodiments, a PNPLA3 RNAi agent comprises the sense strand and antisense strand modified nucleotide sequences of any of the Duplex ID Nos. presented herein and a targeting group and/or linking group, wherein the targeting group and/or linking group is covalently linked to the sense strand or the antisense strand.

In some embodiments, a PNPLA3 RNAi agent comprises an antisense strand and a sense strand having the nucleotide sequences of any of the antisense strand/sense strand duplexes of Table 2 or Tables 5A and 5B, and further comprises a targeting group or targeting ligand. In some embodiments, a PNPLA3 RNAi agent comprises an antisense strand and a sense strand having the nucleotide sequences of any of the antisense strand/sense strand duplexes of Table 2 or Tables 5A and 5B, and further comprises an asialoglycoprotein receptor ligand targeting group.

A targeting group, with or without a linker, can be linked to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In some embodiments, a PNPLA3 RNAi agent comprises an antisense strand and a sense strand having the nucleotide sequences of any of the antisense strand/sense strand duplexes of Table 2 or Tables 5A and 5B, and further comprises a targeting ligand selected from the group consisting of: (NAG37) and (NAG37)s, each as defined in Table 6.

In some embodiments, a PNPLA3 RNAi agent comprises an antisense strand and a sense strand having the modified nucleotide sequence of any of the antisense strand and/or sense strand nucleotide sequences in Table 3 or Table 4.

In some embodiments, a PNPLA3 RNAi agent comprises an antisense strand and a sense strand having a modified nucleotide sequence of any of the antisense strand and/or sense strand nucleotide sequences of any of the duplexes Tables 5A and 5B, and further comprises an asialoglycoprotein receptor ligand targeting group.

In some embodiments, a PNPLA3 RNAi agent comprises, consists of, or consists essentially of any of the duplexes of Tables 5A and 5B.

TABLE 5A

PNPLA3 RNAi Agents Duplexes with Corresponding Sense and Antisense Strand ID Numbers

| Duplex ID | Antisense Strand ID | Sense Strand ID |
|---|---|---|
| J1D00001 | J1M00002-AS | J1M00001-SS |
| J1D00002 | J1M00004-AS | J1M00003-SS |
| J1D00003 | J1M00006-AS | J1M00005-SS |
| J1D00004 | J1M00008-AS | J1M00007-SS |
| J1D00005 | J1M00010-AS | J1M00009-SS |
| J1D00006 | J1M00012-AS | J1M00011-SS |
| J1D00007 | J1M00014-AS | J1M00013-SS |

TABLE 5A-continued

PNPLA3 RNAi Agents Duplexes with Corresponding Sense and Antisense Strand ID Numbers

| Duplex ID | Antisense Strand ID | Sense Strand ID |
|---|---|---|
| J1D00008 | J1M00016-AS | J1M00015-SS |
| J1D00010 | J1M00020-AS | J1M00019-SS |
| J1D00011 | J1M00020-AS | J1M00021-SS |
| J1D00012 | J1M00023-AS | J1M00022-SS |
| J1D00013 | J1M00025-AS | J1M00024-SS |
| J1D00014 | J1M00027-AS | J1M00026-SS |
| J1D00015 | J1M00029-AS | J1M00028-SS |
| J1D00016 | J1M00031-AS | J1M00030-SS |
| J1D00017 | J1M00032-AS | J1M00019-SS |
| J1D00018 | J1M00034-AS | J1M00033-SS |
| J1D00019 | J1M00036-AS | J1M00035-SS |
| J1D00020 | J1M00038-AS | J1M00037-SS |
| J1D00021 | J1M00040-AS | J1M00039-SS |
| J1D00022 | J1M00042-AS | J1M00041-SS |
| J1D00024 | J1M00046-AS | J1M00045-SS |
| J1D00026 | J1M00050-AS | J1M00049-SS |
| J1D00027 | J1M00052-AS | J1M00051-SS |
| J1D00028 | J1M00052-AS | J1M00022-SS |
| J1D00029 | J1M00023-AS | J1M00053-SS |
| J1D00032 | J1M00057-AS | J1M00056-SS |
| J1D00033 | J1M00059-AS | J1M00058-SS |
| J1D00035 | J1M00063-AS | J1M00062-SS |
| J1D00040 | J1M00072-AS | J1M00071-SS |
| J1D00041 | J1M00074-AS | J1M00073-SS |
| J1D00043 | J1M00077-AS | J1M00076-SS |
| J1D00044 | J1M00079-AS | J1M00078-SS |
| J1D00045 | J1M00077-AS | J1M00080-SS |
| J1D00046 | J1M00082-AS | J1M00081-SS |
| J1D00047 | J1M00082-AS | J1M00083-SS |
| J1D00048 | J1M00016-AS | J1M00084-SS |
| J1D00074 | J1M00113-AS | J1M00015-SS |
| J1D00075 | J1M00114-AS | J1M00015-SS |
| J1D00076 | J1M00115-AS | J1M00015-SS |
| J1D00077 | J1M00116-AS | J1M00015-SS |
| J1D00078 | J1M00016-AS | J1M00117-SS |
| J1D00079 | J1M00016-AS | J1M00118-SS |
| J1D00080 | J1M00016-AS | J1M00119-SS |
| J1D00081 | J1M00121-AS | J1M00120-SS |
| J1D00082 | J1M00123-AS | J1M00122-SS |
| J1D00083 | J1M00125-AS | J1M00124-SS |
| J1D00084 | J1M00127-AS | J1M00126-SS |
| J1D00085 | J1M00129-AS | J1M00128-SS |
| J1D00087 | J1M00133-AS | J1M00132-SS |

TABLE 5B

PNPLA3 RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| J1D00001 | J1M00002-AS | 88 | 174 | J1M00001-SS | 129 | 212 |
| J1D00002 | J1M00004-AS | 89 | 175 | J1M00003-SS | 130 | 213 |
| J1D00003 | J1M00006-AS | 90 | 176 | J1M00005-SS | 131 | 214 |
| J1D00004 | J1M00008-AS | 91 | 177 | J1M00007-SS | 132 | 215 |
| J1D00005 | J1M00010-AS | 92 | 178 | J1M00009-SS | 133 | 216 |
| J1D00006 | J1M00012-AS | 93 | 179 | J1M00011-SS | 134 | 217 |
| J1D00007 | J1M00014-AS | 94 | 180 | J1M00013-SS | 135 | 218 |
| J1D00008 | J1M00016-AS | 95 | 181 | J1M00015-SS | 136 | 219 |
| J1D00010 | J1M00020-AS | 96 | 182 | J1M00019-SS | 137 | 220 |
| J1D00011 | J1M00020-AS | 96 | 183 | J1M00021-SS | 138 | 221 |
| J1D00012 | J1M00023-AS | 97 | 184 | J1M00022-SS | 139 | 222 |
| J1D00013 | J1M00025-AS | 98 | 185 | J1M00024-SS | 140 | 223 |
| J1D00014 | J1M00027-AS | 99 | 186 | J1M00026-SS | 141 | 224 |
| J1D00015 | J1M00029-AS | 100 | 187 | J1M00028-SS | 142 | 225 |
| J1D00016 | J1M00031-AS | 101 | 188 | J1M00030-SS | 143 | 226 |
| J1D00017 | J1M00032-AS | 102 | 189 | J1M00019-SS | 137 | 220 |

TABLE 5B-continued

PNPLA3 RNAi Agents Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| J1D00018 | J1M00034-AS | 103 | 190 | J1M00033-SS | 144 | 227 |
| J1D00019 | J1M00036-AS | 104 | 191 | J1M00035-SS | 145 | 228 |
| J1D00020 | J1M00038-AS | 105 | 192 | J1M00037-SS | 146 | 229 |
| J1D00021 | J1M00040-AS | 106 | 193 | J1M00039-SS | 147 | 230 |
| J1D00022 | J1M00042-AS | 107 | 194 | J1M00041-SS | 148 | 231 |
| J1D00024 | J1M00046-AS | 108 | 195 | J1M00045-SS | 149 | 232 |
| J1D00026 | J1M00050-AS | 109 | 196 | J1M00049-SS | 150 | 233 |
| J1D00027 | J1M00052-AS | 110 | 197 | J1M00051-SS | 151 | 234 |
| J1D00028 | J1M00052-AS | 110 | 198 | J1M00022-SS | 152 | 222 |
| J1D00029 | J1M00023-AS | 97 | 183 | J1M00053-SS | 153 | 235 |
| J1D00032 | J1M00057-AS | 111 | 199 | J1M00056-SS | 154 | 237 |
| J1D00033 | J1M00059-AS | 112 | 200 | J1M00058-SS | 155 | 238 |
| J1D00035 | J1M00063-AS | 113 | 201 | J1M00062-SS | 156 | 239 |
| J1D00040 | J1M00072-AS | 114 | 202 | J1M00071-SS | 157 | 240 |
| J1D00041 | J1M00074-AS | 115 | 203 | J1M00073-SS | 158 | 241 |
| J1D00043 | J1M00077-AS | 116 | 204 | J1M00076-SS | 159 | 242 |
| J1D00044 | J1M00079-AS | 117 | 205 | J1M00078-SS | 160 | 243 |
| J1D00045 | J1M00077-AS | 116 | 206 | J1M00080-SS | 161 | 244 |
| J1D00046 | J1M00082-AS | 118 | 207 | J1M00081-SS | 162 | 245 |
| J1D00047 | J1M00082-AS | 118 | 207 | J1M00083-SS | 163 | 246 |
| J1D00048 | J1M00016-AS | 95 | 181 | J1M00084-SS | 164 | 247 |
| J1D00074 | J1M00113-AS | 119 | 210 | J1M00015-SS | 136 | 219 |
| J1D00075 | J1M00114-AS | 120 | 211 | J1M00015-SS | 136 | 219 |
| J1D00076 | J1M00115-AS | 121 | 212 | J1M00015-SS | 136 | 219 |
| J1D00077 | J1M00116-AS | 122 | 213 | J1M00015-SS | 136 | 219 |
| J1D00078 | J1M00016-AS | 95 | 181 | J1M00117-SS | 165 | 248 |
| J1D00079 | J1M00016-AS | 95 | 181 | J1M00118-SS | 166 | 249 |
| J1D00080 | J1M00016-AS | 95 | 181 | J1M00119-SS | 167 | 250 |
| J1D00081 | J1M00121-AS | 123 | 206 | J1M00120-SS | 168 | 251 |
| J1D00082 | J1M00123-AS | 124 | 207 | J1M00122-SS | 169 | 252 |
| J1D00083 | J1M00125-AS | 125 | 208 | J1M00124-SS | 170 | 253 |
| J1D00084 | J1M00127-AS | 126 | 209 | J1M00126-SS | 171 | 254 |
| J1D00085 | J1M00129-AS | 127 | 210 | J1M00128-SS | 172 | 255 |
| J1D00087 | J1M00133-AS | 128 | 211 | J1M00132-SS | 173 | 256 |

In some embodiments, a PNPLA3 RNAi agent is prepared or provided as a salt, mixed salt, or a free-acid. The RNAi agents described herein, upon delivery to a cell expressing a PNPLA3 gene, inhibit or knockdown expression of one or more PNPLA3 genes in vivo and/or in vitro.

Targeting Ligands or Groups, Linking Groups, and Delivery Vehicles

In some embodiments, a PNPLA3 RNAi agent is conjugated to one or more non-nucleotide groups including, but not limited to, a targeting group, a linking group, a targeting ligand, a delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, a PNPLA3 RNAi agent contains a non-nucleotide group linked to the 3' and/or 5' end of the sense strand. In some embodiments, a non-nucleotide group is linked to the 5' end of a PNPLA3 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules.

In some embodiments, a targeting group is linked to an RNAi agent using a linker, such as a PEG linker or one, two, or three abasic and/or ribitol (abasic ribose) residues, which can in some instances serve as linkers. In some embodiments, a targeting ligand comprises a galactose-derivative cluster.

The PNPLA3 RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

In some embodiments, a targeting group comprises an asialoglycoprotein receptor ligand. As used herein, an asialoglycoprotein receptor ligand is a ligand that contains a moiety having affinity for the asialoglycoprotein receptor. As noted herein, the asialoglycoprotein receptor is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative, also referred to as monovalent or monodentate) or multimeric (e.g., having multiple galactose derivatives). The galactose derivative or galactose derivative cluster can be attached to the 3' or 5' end of the sense or antisense strand of the RNAi agent using methods known in the art. The preparation of targeting ligands, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see. e.g., U.S. Pat. No. 5,885,968; Biessen et al. J. Med. Chem. 1995 Vol. 39 p. 1538-1546). In some embodiments, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering a PNPLA3 RNAi agent to a liver cell in vivo. Such pharmaceutical compositions can include, for example, a PNPLA3 RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

A targeting ligand or targeting group can be linked to the 3' or 5' end of a sense strand or an antisense strand of a PNPLA3 RNAi agent disclosed herein.

Targeting ligands include, but are not limited to (NAG37) and (NAG37)s as defined in Table 6. Other targeting groups and targeting ligands, including galactose cluster targeting ligands, are known in the art.

In some embodiments, a linking group is conjugated to the RNAi agent. The linking group facilitates covalent linkage of the agent to a targeting group, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

In some embodiments, a targeting group is linked internally to a nucleotide on the sense strand and/or the antisense strand of the RNAi agent. In some embodiments, a targeting group is linked to the RNAi agent via a linker.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage can optionally include a spacer that increases the distance between the two joined atoms. A spacer can further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, when two or more RNAi agents are included in a single composition, each of the RNAi agents may be linked to the same targeting group or two a different targeting groups (i.e., targeting groups having different chemical structure). In some embodiments, targeting groups are linked to the PNPLA3 RNAi agents disclosed herein without the use of an additional linker. In some embodiments, the targeting group itself is designed having a linker or other site to facilitate conjugation readily present. In some embodiments, when two or more PNPLA3 RNAi agents are included in a single molecule, each of the RNAi agents may utilize the same linker or different linkers (i.e., linkers having different chemical structures).

Any of the PNPLA3 RNAi agent nucleotide sequences listed in Tables 2, 3, or 4, whether modified or unmodified, can contain 3' and/or 5' targeting group(s) or linking group(s). Any of the PNPLA3 RNAi agent sequences listed in Table 3 or 4, or are otherwise described herein, which contain a 3' or 5' targeting group or linking group, can alternatively contain no 3' or 5' targeting group or linking group, or can contain a different 3' or 5' targeting group or linking group including, but not limited to, those depicted in Table 6. Any of the PNPLA3 RNAi agent duplexes listed in Tables 5A and 5B, whether modified or unmodified, can further comprise a targeting group or linking group, including, but not limited to, those depicted in Table 6, and the targeting group or linking group can be attached to the 3' or 5' terminus of either the sense strand or the antisense strand of the PNPLA3 RNAi agent duplex.

Examples of targeting groups and linking groups (which when combined can form targeting ligands) are provided in Table 6. Table 4 provides several embodiments of PNPLA3 RNAi agent sense strands having a targeting group or linking group linked to the 5' or 3' end.

TABLE 6

Structures Representing Various Modified Nucleotides, Targeting Ligands or Targeting Groups, Capping Residues, and Linking Groups

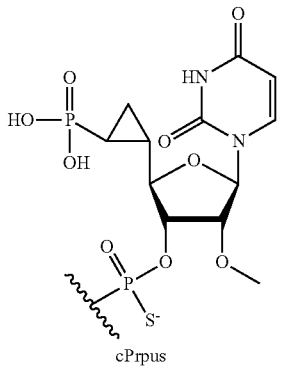

cPrpus

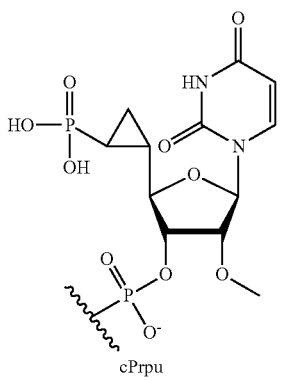

cPrpu

TABLE 6-continued

Structures Representing Various Modified Nucleotides, Targeting Ligands or Targeting Groups, Capping Residues, and Linking Groups

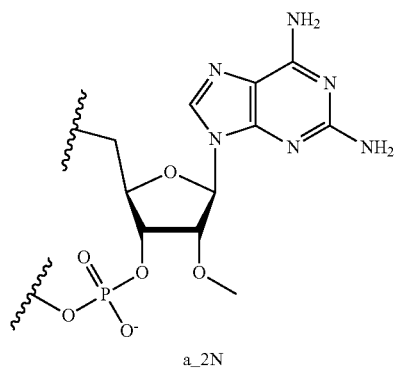

a_2N

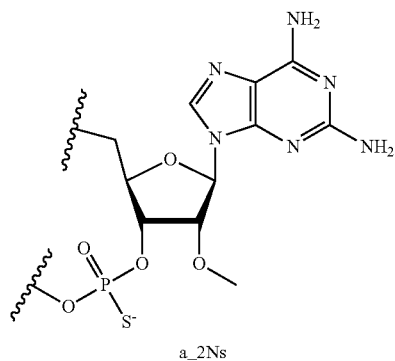

a_2Ns

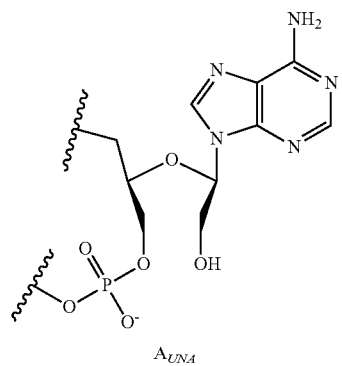

$A_{UNA}$

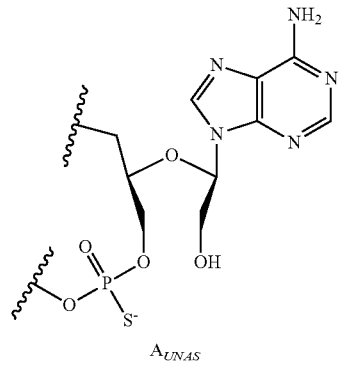

$A_{UNAS}$

TABLE 6-continued
Structures Representing Various Modified Nucleotides, Targeting Ligands or Targeting Groups, Capping Residues, and Linking Groups
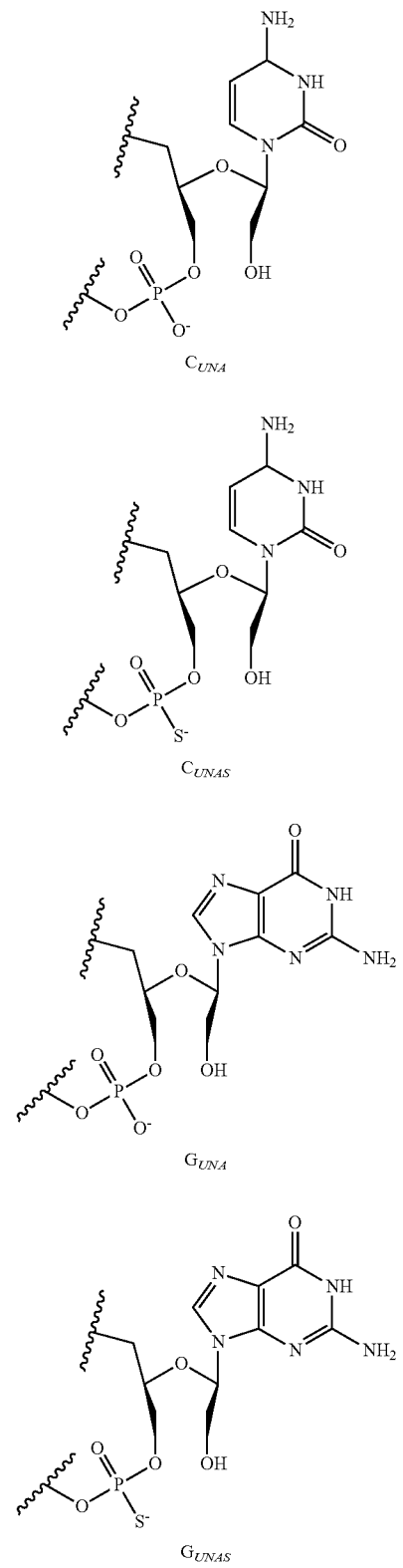
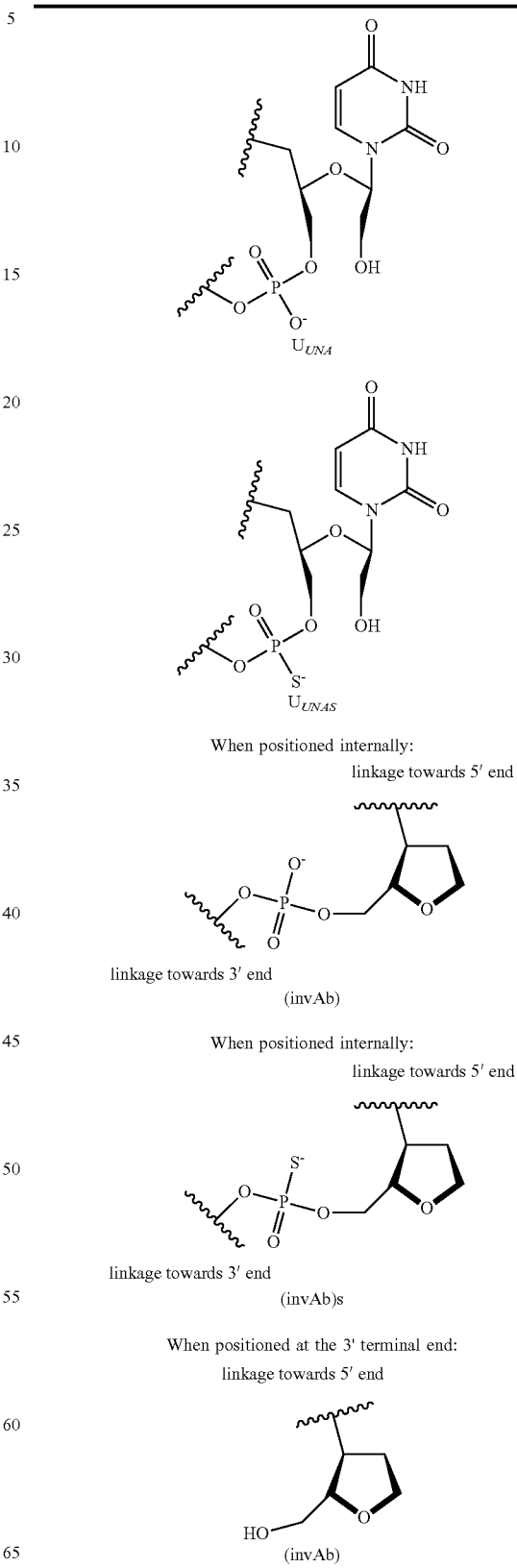

TABLE 6-continued

Structures Representing Various Modified Nucleotides, Targeting Ligands or Targeting Groups, Capping Residues, and Linking Groups

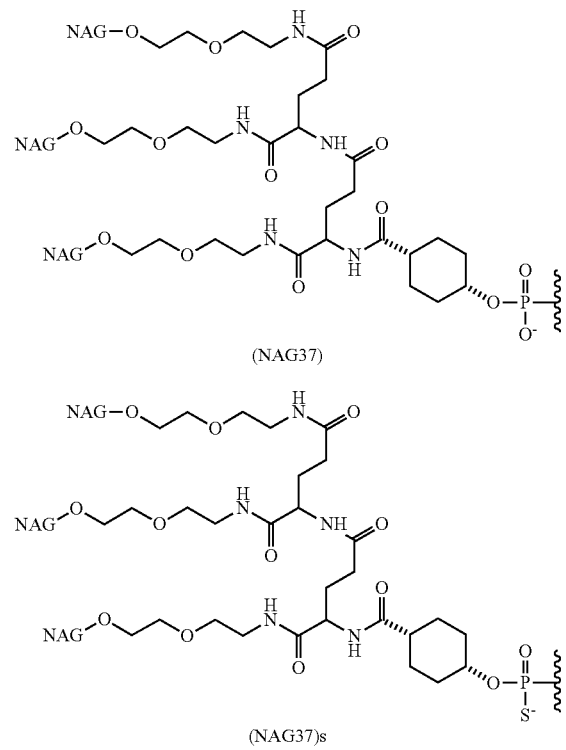

(NAG37)

(NAG37)s

In each of the above structures in Table 6, NAG comprises an N-acetyl-galactosamine or another galactose derivative, as would be understood by a person of ordinary skill in the art to be attached in view of the structures above and description provided herein.

Each (NAGx) may be attached to a PNPLA3 RNAi agent via a phosphate group (as in (NAG37)), or a phosphorothioate group, (as is (NAG37)s), or another linking group.

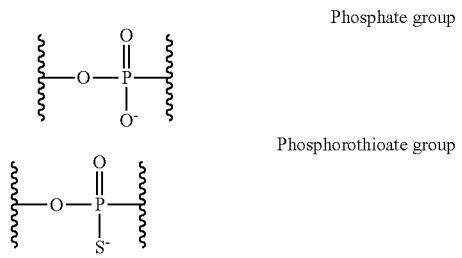

Phosphate group

Phosphorothioate group

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), hydrogels, cyclodextrins, biodegradable nanocapsules, and bioadhesive microspheres, proteinaceous vectors, or other delivery systems suitable for nucleic acid or oligonucleotide delivery as known and available in the art.

Pharmaceutical Compositions and Formulations

The PNPLA3 RNAi agents disclosed herein can be prepared as pharmaceutical compositions or formulations (also referred to herein as "medicaments"). In some embodiments, pharmaceutical compositions include at least one PNPLA3 RNAi agent. These pharmaceutical compositions are particularly useful in the inhibition of the expression of the target mRNA in a target cell, a group of cells, a tissue, or an organism.

The pharmaceutical compositions can be used to treat a subject having a disease, disorder, or condition that would benefit from reduction in the level of the target PNPLA3 mRNA, or inhibition in expression of the target gene. The pharmaceutical compositions can be used to treat a subject at risk of developing a disease, disorder, or condition that would benefit from reduction of the level of the target mRNA or an inhibition in expression the target gene. In one embodiment, the method includes administering a PNPLA3 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a PNPLA3 RNAi agent, thereby forming a pharmaceutical formulation or medicament suitable for in vivo delivery to a subject, including a human.

The pharmaceutical compositions that include a PNPLA3 RNAi agent and methods disclosed herein decrease the level of the target mRNA in a cell, group of cells, group of cells, tissue, organ, or subject, including by administering to the subject a therapeutically effective amount of a herein described PNPLA3 RNAi agent, thereby inhibiting the expression of PNPLA3 mRNA in the subject. In some embodiments, the subject has been previously identified or diagnosed as having a pathogenic upregulation of the target gene in the targeted cell or tissue. In some embodiments, the subject has been previously identified or diagnosed as having NAFLD, NASH, hepatic fibrosis, and/or alcoholic or non-alcoholic liver disease, such as cirrhosis. In some embodiments, the subject has been suffering from symptoms associated with NAFLD, NASH, hepatic fibrosis, and/or alcoholic or non-alcoholic liver disease, such as cirrhosis.

In some embodiments, the described pharmaceutical compositions including a PNPLA3 RNAi agent are used for treating or managing clinical presentations associated with NAFLD, NASH, hepatic fibrosis, alcoholic or non-alcoholic liver diseases, including cirrhosis, and/or over-expression of PNPLA3 in a subject. In some embodiments, a therapeutically (including prophylactically) effective amount of one or more of pharmaceutical compositions is administered to a subject in need of such treatment. In some embodiments, administration of any of the disclosed PNPLA3 RNAi agents can be used to decrease the number, severity, and/or frequency of symptoms of a disease in a subject.

The described pharmaceutical compositions that include a PNPLA3 RNAi agent can be used to treat at least one symptom in a subject having a disease or disorder that would benefit from reduction or inhibition in expression of PNPLA3 mRNA. In some embodiments, the subject is administered a therapeutically effective amount of one or more pharmaceutical compositions that include a PNPLA3 RNAi agent thereby treating the symptom. In other embodiments, the subject is administered a prophylactically effective amount of one or more PNPLA3 RNAi agents, thereby preventing or inhibiting the at least one symptom.

The route of administration is the path by which a PNPLA3 RNAi agent is brought into contact with the body. In general, methods of administering drugs and oligonucleotides and nucleic acids for treatment of a mammal are well known in the art and can be applied to administration of the compositions described herein. The PNPLA3 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including a PNPLA3 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., PNPLA3 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, NJ) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

In some embodiments, pharmaceutical formulations that include the PNPLA3 RNAi agents disclosed herein suitable for subcutaneous administration can be prepared in an aqueous sodium phosphate buffer (e.g., the PNPLA3 RNAi agent formulated in 0.5 mM sodium phosphate monobasic, 0.5 mM sodium phosphate dibasic, in water)

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for oral administration of the PNPLA3 RNAi agents disclosed herein can also be prepared. In some embodiments, the PNPLA3 RNAi agents disclosed herein are administered orally. In some embodiments, the PNPLA3 RNAi agents disclosed herein are formulated in a capsule for oral administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The PNPLA3 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another PNPLA3 RNAi agent (e.g., a PNPLA3 RNAi agent that targets a different sequence within the PNPLA3 target). In other embodiments, the second therapeutic can be a small molecule drug, an antibody, an antibody fragment, or an aptamer.

In some embodiments, the described PNPLA3 RNAi agent(s) are optionally combined with one or more additional therapeutics. The PNPLA3 RNAi agent and additional therapeutic(s) can be administered in a single composition or they can be administered separately. In some embodiments, the one or more additional therapeutics is administered separately in separate dosage forms from the RNAi agent (e.g., the PNPLA3 RNAi agent is administered by subcutaneous injection, while the additional therapeutic involved in the method of treatment dosing regimen is administered orally). In some embodiments, the described PNPLA3 RNAi agent(s) are administered to a subject in need thereof via subcutaneous injection, and the one or more optional additional therapeutics are administered orally, which together provide for a treatment regimen for diseases and conditions associated with NAFLD, NASH, hepatic fibrosis, and/or alcoholic or non-alcoholic liver diseases, including cirrhosis. In some embodiments, the described PNPLA3 RNAi agent(s) are administered to a subject in need thereof via subcutaneous injection, and the one or more optional additional therapeutics are administered via a separate subcutaneous injection. In some embodiments, the PNPLA3 RNAi agent and one or more additional therapeutics are combined into a single dosage form (e.g., a "cocktail" formulated into a single composition for subcutaneous injection). The PNPLA3 RNAi agents, with or without the one or more additional therapeutics, can be combined with one or more excipients to form pharmaceutical compositions.

Generally, an effective amount of a PNPLA3 RNAi agent will be in the range of from about 0.1 to about 100 mg/kg of body weight/dose, e.g., from about 1.0 to about 50 mg/kg of body weight/dose. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. Dosing may be weekly, bi-weekly, monthly, or at any other interval depending on the dose of PNPLA3 RNAi agent administered, the activity level of the particular PNPLA3 RNAi agent, and the desired level of inhibition for the particular subject. The Examples herein show suitable levels for inhibition in certain animal species. The amount administered will depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including a PNPLA3 RNAi agent can be combined with an excipient or with a second therapeutic agent or treatment including, but not limited to: a second or other RNAi agent, a small molecule drug, an antibody, an antibody fragment, peptide and/or an aptamer.

The described PNPLA3 RNAi agents, when added to pharmaceutically acceptable excipients or adjuvants, can be packaged into kits, containers, packs, or dispensers. The pharmaceutical compositions described herein may be packaged in pre-filled syringes, pen injectors, autoinjectors, infusion bags/devices, or vials.

Methods of Treatment and Inhibition of Expression

The PNPLA3 RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from reduction and/or inhibition in expression of PNPLA3 mRNA and/or PNPLA3 protein levels, for example, a subject that has been diagnosed with or is suffering from symptoms related to NAFLD, NASH, hepatic fibrosis, or alcoholic or non-alcoholic liver diseases, including cirrhosis.

In some embodiments, the subject is administered a therapeutically effective amount of any one or more PNPLA3 RNAi agents. Treatment of a subject can include therapeutic and/or prophylactic treatment. The subject is administered a therapeutically effective amount of any one or more PNPLA3 RNAi agents described herein. The subject can be a human, patient, or human patient. The subject may be an adult, adolescent, child, or infant. Administration of a pharmaceutical composition described herein can be to a human being or animal.

The PNPLA3 RNAi agents described herein can be used to treat at least one symptom in a subject having a PNPLA3-related disease or disorder, or having a disease or disorder that is mediated at least in part by PNPLA3 gene expression. In some embodiments, the PNPLA3 RNAi agents are used to treat or manage a clinical presentation of a subject with a disease or disorder that would benefit from or be mediated at least in part by a reduction in PNPLA3 mRNA. The subject is administered a therapeutically effective amount of one or more of the PNPLA3 RNAi agents or PNPLA3 RNAi agent-containing compositions described herein. In some embodiments, the methods disclosed herein comprise administering a composition comprising a PNPLA3 RNAi agent described herein to a subject to be treated. In some embodiments, the subject is administered a prophylactically effective amount of any one or more of the described PNPLA3 RNAi agents, thereby treating the subject by preventing or inhibiting the at least one symptom.

In certain embodiments, the present disclosure provides methods for treatment of diseases, disorders, conditions, or pathological states mediated at least in part by PNPLA3 gene expression, in a patient in need thereof, wherein the methods include administering to the patient any of the PNPLA3 RNAi agents described herein.

In some embodiments, the gene expression level and/or mRNA level of a PNPLA3 gene in a subject to whom a described PNPLA3 RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the PNPLA3 RNAi agent or to a subject not receiving the PNPLA3 RNAi agent. The gene expression level and/or mRNA level in the subject may be reduced in a cell, group of cells, and/or tissue of the subject. In some embodiments, the PNPLA3 gene expression is inhibited by at least about 50%, 55%, 60%, 65%, 66%, 67%, 68%, 69%, 70%, or greater than 70% in the cytoplasm of hepatocytes relative to the subject prior to being administered the PNPLA3 RNAi agent or to a subject not receiving the PNPLA3 RNAi agent.

In some embodiments, the PNPLA3 protein level in a subject to whom a described PNPLA3 RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the PNPLA3 RNAi agent or to a subject not receiving the PNPLA3 RNAi agent. The protein level in the subject may be reduced in a cell, group of cells, tissue, blood, and/or other fluid of the subject.

A reduction in PNPLA3 mRNA levels and PNPLA3 protein levels can be assessed by any methods known in the art. As used herein, a reduction or decrease in PNPLA3 mRNA level and/or protein level are collectively referred to herein as a reduction or decrease in PNPLA3 or inhibiting or reducing the expression of PNPLA3. The Examples set forth herein illustrate known methods for assessing inhibition of PNPLA3 gene expression. The person of ordinary skill in the art would further know suitable methods for assessing inhibition of PNPLA3 gene expression in vivo and/or in vitro.

In some embodiments, disclosed herein are methods of treatment (including prophylactic or preventative treatment) of diseases, disorders, or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of a PNPLA3 RNAi agent that includes an antisense strand that is at least partially complementary to the portion of the PNPLA3 mRNA having the sequence in Table 1. In some embodiments, disclosed herein are methods of treatment (including prophylactic or preventative treatment) of diseases or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of a PNPLA3 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of treatment (including prophylactic or preventative treatment) of diseases or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of a PNPLA3 RNAi agent that includes a sense strand that comprises any of the sequences in Tables 2 or 4, and an antisense strand comprising the sequence of any of the sequences in Tables 2 or 3 that is at least partially complementary to the sense strand.

In some embodiments, disclosed herein are methods for inhibiting expression of a PNPLA3 gene in a cell, wherein the methods include administering to the cell a PNPLA3 RNAi agent that includes an antisense strand that is at least partially complementary to the portion of the PNPLA3 mRNA having the sequence in Table 1. In some embodiments, disclosed herein are methods of inhibiting expression of a PNPLA3 gene in a cell, wherein the methods include administering to a cell a PNPLA3 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of inhibiting expression of a PNPLA3 gene in a cell, wherein the methods include administering a PNPLA3 RNAi agent that includes a sense strand that comprises any of the sequences in Tables 2 or 4, and an antisense strand that includes the sequence of any of the sequences in Tables 2 or 3 that is at least partially complementary to the sense strand.

The use of PNPLA3 RNAi agents provides methods for therapeutic (including prophylactic) treatment of diseases/disorders associated with NAFLD, NASH, hepatic fibrosis, alcoholic or non-alcoholic liver diseases, including cirrhosis, and/or enhanced or elevated PNPLA3 expression. The described PNPLA3 RNAi agents mediate RNA interference to inhibit the expression of one or more genes necessary for production of PNPLA3 protein. PNPLA3 RNAi agents can also be used to treat or prevent various diseases, disorders, or conditions, including NAFLD, NASH, hepatic fibrosis, and/or alcoholic or non-alcoholic liver diseases, including cirrhosis. Furthermore, compositions for delivery of PNPLA3 RNAi agents to liver cells in vivo are described.

Cells, Tissues, Organs, and Non-Human Organisms

Cells, tissues, organs, and non-human organisms that include at least one of the PNPLA3 RNAi agents described herein are contemplated. The cell, tissue, organ, or non-human organism is made by delivering the RNAi agent to the cell, tissue, organ or non-human organism.

Illustrative Embodiments

Provided here are illustrative embodiments of the disclosed technology. These embodiments are illustrative only and do not limit the scope of the present disclosure or of the claims attached hereto.

Embodiment 1. An RNAi agent for inhibiting expression of a PNPLA3 gene, comprising:
an antisense strand comprising at least 17 contiguous nucleotides differing by 0 or 1 nucleotides from any one of the sequences of SEQ ID NOs: 46-87, 174-211, 257, and 258; and a sense strand comprising a nucleotide sequence that is at least partially complementary to the antisense strand.

Embodiment 2. The RNAi agent of embodiment 1, wherein the antisense strand comprises nucleotides 2-18 of any one of the sequences of SEQ ID NOs: 46-87, 174-211, 257, and 258.

Embodiment 3. The RNAi agent of embodiment 1 or embodiment 2, wherein the sense strand comprises a nucleotide sequence of at least 17 contiguous nucleotides differing by 0 or 1 nucleotides from any one of the sense strand sequences of SEQ ID NOs: 2-45 and 212-256, and wherein the sense strand has a region of at least 85% complementarity over the 17 contiguous nucleotides to the antisense strand.

Embodiment 4. The RNAi agent of any one of embodiments 1-3, wherein at least one nucleotide of the RNAi agent is a modified nucleotide or includes a modified internucleoside linkage.

Embodiment 5. The RNAi agent of any one of embodiments 1-3, wherein all or substantially all of the nucleotides of the sense and/or antisense strand of the RNAi agent are modified nucleotides.

Embodiment 6. The RNAi agent of any one of embodiments 4-5, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

Embodiment 7. The RNAi agent of embodiment 5, wherein all or substantially all of the modified nucleotides are 2'-O-methyl nucleotides, 2'-fluoro nucleotides, or combinations thereof.

Embodiment 8. The RNAi agent of any one of embodiments 1-7, wherein the antisense strand comprises the nucleotide sequence of any one of the modified antisense strand sequences of SEQ ID NOs: 88-128.

Embodiment 9. The RNAi agent of any one of embodiments 1-8, wherein the sense strand comprises the nucleotide sequence of any of the modified sense strand sequences of SEQ ID NOs: 129-173.

Embodiment 10. The RNAi agent of embodiment 1, wherein the antisense strand comprises the nucleotide sequence of any one of the modified sequences of SEQ ID NOs: 88-128 and the sense strand comprises the nucleotide sequence of any one of the modified sequences of SEQ ID NOs: 129-173.

Embodiment 11. The RNAi agent of any one of embodiments 1-10, wherein the RNAi agent is linked to a targeting ligand.

Embodiment 12. The RNAi agent of embodiment 11, wherein the targeting ligand comprises n-acetyl-galactosamine.

Embodiment 13. The RNAi agent of embodiment 11 or 12, wherein the targeting ligand comprises the structure of (NAG37) or (NAG37)s.

Embodiment 14. The RNAi agent of any one of embodiments 11-14, wherein the targeting ligand is linked to the sense strand.

Embodiment 15. The RNAi agent of embodiment 15, wherein the targeting ligand is linked to the 5' terminal end of the sense strand.

Embodiment 16. The RNAi agent of any one of embodiments 1-16, wherein the sense strand is between 18 and 30 nucleotides in length, and the antisense strand is between 18 and 30 nucleotides in length.

Embodiment 17. The RNAi agent of embodiment 17, wherein the sense strand and the antisense strand are each between 18 and 27 nucleotides in length.

Embodiment 18. The RNAi agent of embodiment 18, wherein the sense strand and the antisense strand are each between 18 and 24 nucleotides in length.

Embodiment 19. The RNAi agent of embodiment 19, wherein the sense strand and the antisense strand are each 21 nucleotides in length.

Embodiment 20. The RNAi agent of any one of embodiments 17-20, wherein the RNAi agent has two blunt ends.

Embodiment 21. The RNAi agent of any one of embodiments 1-21, wherein the sense strand comprises one or two terminal caps.

Embodiment 22. The RNAi agent of any one of embodiments 1-22, wherein the sense strand comprises one or two inverted abasic residues.

Embodiment 23. The RNAi agent of embodiment 1, wherein the RNAi agent is comprised of a sense strand and an antisense strand that form a duplex sequence of any one of the duplexes with SEQ ID NOs as listed in Table 5B.

Embodiment 24. The RNAi agent of any one of embodiments 1-23, wherein the sense strand further includes inverted abasic residues at the 3' terminal end of the nucleotide sequence, at the 5' end of the nucleotide sequence, or at both.

Embodiment 25. The RNAi agent of embodiment 1, comprising an antisense strand that comprises, consists of, or consists essentially of a modified nucleotide sequence that differs by 0 or 1 nucleotides from one of the nucleotide sequences of SEQ ID NOs: 88-128, wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; s represents a phosphorothioate linkage; and wherein all or substantially all of the nucleotides on the sense strand are modified nucleotides.

Embodiment 26. The RNAi agent of embodiment 1, wherein the sense strand comprises, consists of, or consists essentially of a modified nucleotide sequence that differs by 0 or 1 nucleotides from one of the nucleotide sequences of SEQ ID NOs: 129-173, wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; s represents a phosphorothioate linkage; and wherein all or substantially all of the nucleotides on the antisense strand are modified nucleotides.

Embodiment 27. The RNAi agent of any one of embodiments 24-26, wherein the sense strand further includes inverted abasic residues at the 3' terminal end of the nucleotide sequence, at the 5' end of the nucleotide sequence, or at both.

Embodiment 28. The RNAi agent of any one of embodiments 24-27, wherein the sense strand of the RNAi agent is linked to a targeting ligand.

Embodiment 29. The RNAi agent of embodiment 28, wherein the targeting ligand has affinity for the asialoglycoprotein receptor.

Embodiment 30. The RNAi agent of embodiment 29, wherein the targeting ligand comprises N-acetyl-galactosamine.

Embodiment 31. The RNAi agent of embodiment 1, wherein the targeting ligand comprises:

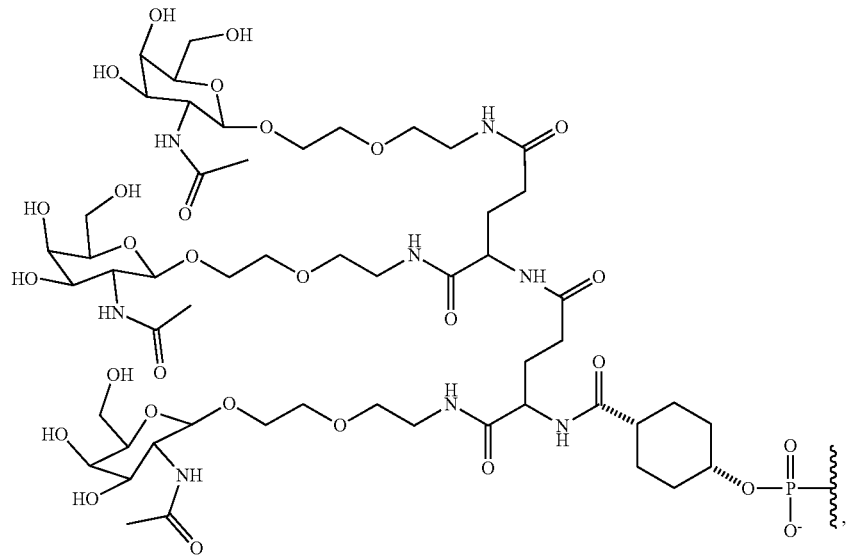

or

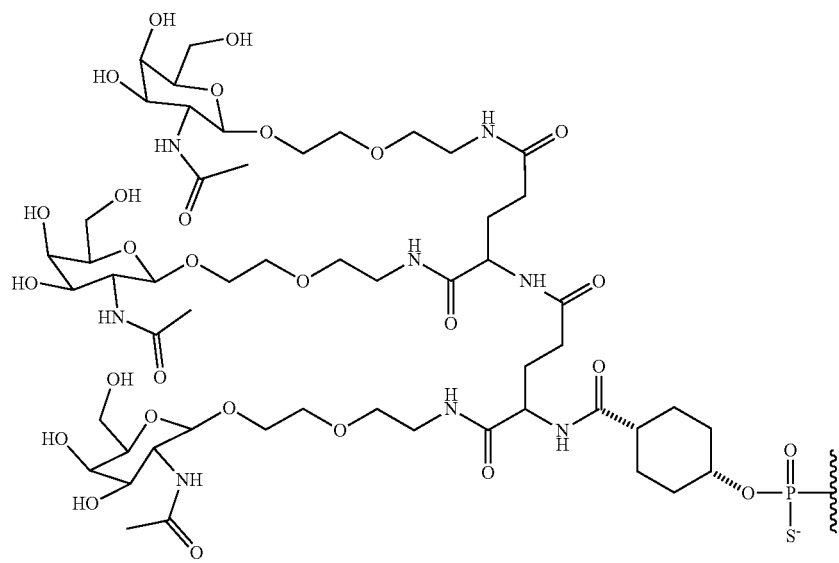

Embodiment 32. The RNAi agent of embodiment 1, wherein the antisense strand consists of the modified nucleotide sequence of SEQ ID NO: 88-128 and the sense strand consists of the modified nucleotide sequence of SEQ ID NO: 129-173, wherein a, c, g, and u are 2'-O-methyl adenosine, cytidine, guanosine, and uridine, respectively; Af, Cf, Gf, and Uf are 2'-fluoro adenosine, cytidine, guanosine, and uridine, respectively; s is a phosphorothioate linkage; (invAb) is an inverted abasic deoxyribose residue; and (NAG37)s has the following chemical structure:

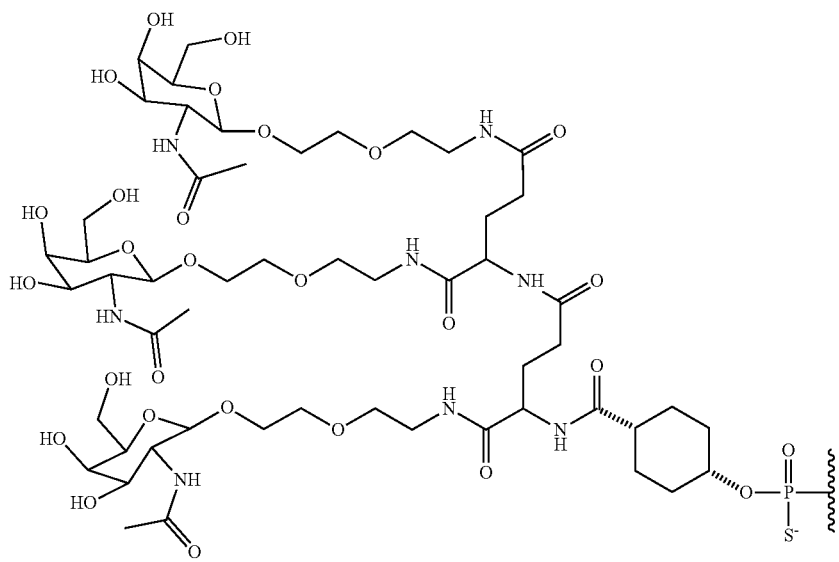

Embodiment 33. A composition comprising the RNAi agent of any one of embodiments 1-32, wherein the composition further comprises a pharmaceutically acceptable excipient.

Embodiment 34. A method for inhibiting expression of a PNPLA3 gene in a cell, the method comprising introducing into a cell an effective amount of an RNAi agent of any one of embodiments 1-32 or the composition of any one of embodiments 33.

Embodiment 35. The method of embodiment 34, wherein the cell is within a subject.

Embodiment 36. The method of embodiment 35, wherein the subject is a human subject.

Embodiment 37. The method of any one of embodiments 34-36, wherein the PNPLA3 gene expression is inhibited by at least about 30%.

Embodiment 38. A method of treating a PNPLA3-related disease or disorder, the method comprising administering to a human subject in need thereof a therapeutically effective amount of the composition of embodiment 33.

Embodiment 39. The method of embodiment 38, wherein the disease is NAFLD, NASH, hepatic fibrosis, alcoholic fatty liver disease, or cirrhosis.

Embodiment 40. The method of any one of embodiments 34-39, wherein the RNAi agent is administered at a dose of about 0.05 mg/kg to about 5.0 mg/kg of body weight of the human subject.

Embodiment 41. The method of any one of embodiments 34-40, wherein the RNAi agent is administered in two or more doses.

Embodiment 42. Use of the RNAi agent of any one of embodiments 1-32 or the composition according to embodiment 33, for the treatment of a disease, disorder, or symptom that is mediated at least in part PNPLA3 gene expression.

Embodiment 43. Use according to embodiment 42, wherein the symptom is cirrhosis of the liver.

Embodiment 44. Use of the RNAi agent of any one of embodiments 1-32 or the composition according to embodiment 33, for the preparation of a pharmaceutical compositions for treating a disease, disorder, or symptom that is mediated at least in part by PNPLA3 gene expression.

Embodiment 45. Use of the RNAi agent according to any one of embodiments 42 to 44, wherein the disease is NAFLD, NASH, hepatic fibrosis, or an alcoholic or non-alcoholic liver disease such as cirrhosis.

Embodiment 46. Use of the composition of embodiment 33, wherein the RNAi agent is administered at a dose of about 0.05 mg/kg to about 5.0 mg/kg of body weight of the human subject.

The above provided embodiments and items are now illustrated with the following, non-limiting examples.

EXAMPLES

Example 1. Synthesis of PNPLA3 RNAi Agents

PNPLA3 RNAi agent duplexes shown in Tables 5A and 5B, above, were synthesized in accordance with the following general procedures:

A. Synthesis.

The sense and antisense strands of the RNAi agents were synthesized according to phosphoramidite technology on solid phase used in oligonucleotide synthesis. Such standard synthesis is generally known in the art. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). The monomer positioned at the 3' end of the respective strand was attached to the solid support as a starting point for synthesis. All RNA and 2'-modified RNA phosphoramidites were purchased from Thermo Fisher Scientific (Milwaukee, WI, USA) or Hongene Biotech (Shanghai, PRC). The 2'-O-methyl phosphoramidites included the following: (5'-O-dimehoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite.

The 2'-deoxy-2'-fluoro-phosphoramidites carried the same protecting groups as the 2'-O-methyl amidites. 5'-(4,4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. 5'-dimethoxytrityl-2'-O-methyl-inosine-3'-O-(2-cyanoethyl-N,N-diisopropylamino) phosphoramidites were purchased from Glen Research (Virginia) or Hongene Biotech. The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA) or SAFC (St Louis, MO, USA). 5'-O-dimethoxytrityl-$N^2$, $N^6$-(phenoxyacetate)-2'-O-methyl-diaminopurine-3'-(2-cyanoethyl-N,N-diisopropylamino) phosphoramidites were obtained from ChemGenes or Hongene Biotech.

Targeting ligand-containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, MA, USA) in anhydrous Acetonitrile was employed. Unless specifically identified as a "naked" RNAi agent having no targeting ligand present, each of the PNPLA3 RNAi agent duplexes synthesized and tested in the following Examples utilized N-acetyl-galactosamine as "NAG" in the targeting ligand chemical structures represented in Table 6.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel® SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1×Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1×Phosphate-Buffered Saline. The solution absorbance at 260 nm was then multiplied by a conversion factor and the dilution factor to determine the duplex concentration. The conversion factor used was either 0.050 mg/(mL cm) or was calculated from an experimentally determined extinction coefficient.

Example 2. PNPLA3-SEAP Mouse Model

To evaluate certain PNPLA3 RNAi agents, a PNPLA3-SEAP mouse model was used. Six- to eight-week-old female C57BlJ6 albino mice or ICR mice, depending on availability, were transiently transfected in vivo with plasmid by hydrodynamic tail vein injection, administered at least 29 days prior to administration of a PNPLA3 RNAi agent or control. Two types of SEAP plasmids were prepared. The first plasmid contains the human PNPLA3 cDNA sequence (GenBank NM_025225.2 (SEQ ID NO:1)) inserted into the 3' UTR of the SEAP (secreted human placental alkaline phosphatase) reporter gene. Due to perceived instability of the full length transcript over time, a second plasmid was synthesized that included a truncated version of the human PNPLA3 cDNA sequence (specifically nucleotides 501-2210 of GenBank NM_025225.2). One of the two plasmids were selected to transfect into mice. 50 μg of the respective plasmid in Ringer's Solution in a total volume of 10% of the animal's body weight was injected into mice via the tail vein to create PNPLA3-SEAP model mice. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737). Inhibition of expression of PNPLA3 by a PNPLA3 RNAi agent results in concomitant inhibition of SEAP expression, which is measured. Prior to administration of a treatment (between day −7 and day 1 pre-dose), SEAP expression levels in serum were measured by the Phospha-Light™ SEAP Reporter Gene Assay System (Invitrogen), and the mice were grouped according to average SEAP levels.

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C. Serum was collected and measured by the Phospha-Light™ SEAP Reporter Gene Assay System (Invitrogen) according to the manufacturer's instructions. Serum SEAP levels for each animal can be normalized to the control group of mice injected with vehicle control in order to account for the non-treatment related decline in PNPLA3 expression with this model. To do so, first, the SEAP level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal vehicle control group. Alternatively, the serum SEAP levels for each animal was assessed by normalizing to pre-treatment levels only.

Example 3. In Vivo Testing of PNPLA3 RNAi Agents in PNPLA3-SEAP Mice

The PNPLA3-SEAP mouse model described in Example 2, above, using the plasmid containing the full length human PNPLA3 transcript was used. At day 1, each mouse was given a single subcutaneous administration of 200 μl/20 g animal weight containing either 3.0 mg/kg (mpk) of a PNPLA3 RNAi agent formulated in saline, or vehicle control (saline with no RNAi agent), according to the following Table 7.

TABLE 7

Targeted Positions and Dosing Groups of Example 3

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 688 | 3.0 mg/kg J1D00001 | Single injection on day 1 |
| 3 | 688 | 3.0 mg/kg J1D00002 | Single injection on day 1 |
| 4 | 1586 | 3.0 mg/kg J1D00004 | Single injection on day 1 |
| 5 | 2180 | 3.0 mg/kg J1D00008 | Single injection on day 1 |
| 6 | 1179 | 3.0 mg/kg J1D00010 | Single injection on day 1 |
| 7 | 1179 | 3.0 mg/kg J1D00011 | Single injection on day 1 |
| 8 | 571 | 3.0 mg/kg J1D00012 | Single injection on day 1 |
| 9 | 1745 | 3.0 mg/kg J1D00016 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agents J1D00001 (Group 2) and J1D00002 (Group 3) included nucleotide sequences that were designed to inhibit expression of a PNPLA3 gene at position 688 of the gene; the PNPLA3 RNAi agent J1D00004 (Group 4) included nucleotide sequences that were designed to inhibit expression of a PNPLA3 gene at position 1586 of the gene; the PNPLA3 RNAi agent J1D00008 (Group 5) included nucleotide sequences that were designed to inhibit expression of a PNPLA3 gene at position 2180 of the gene; the PNPLA3 RNAi agents J1D00010 (Group 6) and J1D00011 (Group 7) included nucleotide sequences that were designed to inhibit expression of a PNPLA3 gene at position 1179 of the gene; the PNPLA3 RNAi agent J1D00012 (Group 8) included nucleotide sequences that were designed to inhibit expression of a PNPLA3 gene at position 571 of the gene; the PNPLA3 RNAi agent J1D00016 (Group 9) included nucleotide sequences that were designed to inhibit expression of a PNPLA3 gene at position 1745 of the gene. (See, e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 8 and 9:

TABLE 8

Average SEAP Normalized to Pre-Treatment (Day −1) in full length transcript PNPLA3-SEAP Mice from Example 3

| Group ID | Day 8 Ave SEAP | Day 8 Std Dev (+/−) | Day 15 Avg SEAP | Day 15 Std Dev (+/−) | Day 22 Avg SEAP | Day 22 Std Dev (+/−) |
|---|---|---|---|---|---|---|
| Group 1 (Saline vehicle) | 0.402 | 0.136 | 0.398 | 0.097 | 0.285 | 0.159 |
| Group 2 (3.0 mg/kg J1D00001) | 0.325 | 0.120 | 0.260 | 0.129 | 0.144 | 0.068 |
| Group 3 (3.0 mg/kg J1D00002) | 0.279 | 0.076 | 0.237 | 0.114 | 0.174 | 0.019 |
| Group 4 (3.0 mg/kg J1D00004) | 0.186 | 0.055 | 0.145 | 0.065 | 0.073 | 0.038 |
| Group 5 (3.0 mg/kg J1D00008) | 0.160 | 0.027 | 0.115 | 0.034 | 0.073 | 0.026 |
| Group 6 (3.0 mg/kg J1D00010) | 0.298 | 0.054 | 0.299 | 0.104 | 0.203 | 0.084 |
| Group 7 (3.0 mg/kg J1D00011) | 0.264 | 0.052 | 0.194 | 0.077 | 0.095 | 0.054 |
| Group 8 (3.0 mg/kg J1D00012) | 0.170 | 0.047 | 0.159 | 0.053 | 0.113 | 0.045 |
| Group 9 (3.0 mg/kg J1D00016) | 0.302 | 0.108 | 0.246 | 0.079 | 0.162 | 0.054 |

* As noted in Example 2, above, the gradual reduction in SEAP in the vehicle control group (Group 1) over time is due to the loss of the SEAP reporter gene in the cells of the mice due to natural cell replication in the animals, and is not the result of any inhibitory compound.

TABLE 9

Average SEAP Normalized to Pre-Treatment (Day −1) and Vehicle Control in full length transcript PNPLA3-SEAP Mice from Example 3

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) |
|---|---|---|---|---|---|---|
| Group 1 (Saline vehicle) | 1.000 | 0.339 | 1.000 | 0.244 | 1.000 | 0.558 |
| Group 2 (3.0 mg/kg J1D00001) | 0.809 | 0.298 | 0.655 | 0.325 | 0.505 | 0.240 |
| Group 3 (3.0 mg/kg J1D00002) | 0.693 | 0.190 | 0.597 | 0.288 | 0.610 | 0.067 |
| Group 4 (3.0 mg/kg J1D00004) | 0.462 | 0.136 | 0.365 | 0.163 | 0.258 | 0.132 |
| Group 5 (3.0 mg/kg J1D00008) | 0.399 | 0.066 | 0.289 | 0.085 | 0.257 | 0.092 |
| Group 6 (3.0 mg/kg J1D00010) | 0.742 | 0.133 | 0.751 | 0.262 | 0.715 | 0.296 |
| Group 7 (3.0 mg/kg J1D00011) | 0.657 | 0.130 | 0.487 | 0.194 | 0.332 | 0.189 |
| Group 8 (3.0 mg/kg J1D00012) | 0.422 | 0.117 | 0.399 | 0.133 | 0.397 | 0.157 |
| Group 9 (3.0 mg/kg J1D00016) | 0.752 | 0.270 | 0.619 | 0.198 | 0.567 | 0.188 |

Example 4. In Vivo Testing of PNPLA3 RNAi Agents in PNPLA3-SEAP Mice

The PNPLA3-SEAP mouse model described in Example 2, above, using the plasmid containing the full length human PNPLA3 transcript was used. At day 1, each mouse was given a single subcutaneous administration of 200 µl/20 g animal weight containing either 3.0 mg/kg (mpk) of a PNPLA3 RNAi agent formulated in saline, or vehicle control (saline with no RNAi agent), according to the following Table 10.

TABLE 10

Targeted Positions and Dosing Groups of Example 4

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 2180 | 3.0 mg/kg J1D00008 | Single injection on day 1 |
| 3 | 886 | 3.0 mg/kg J1D00014 | Single injection on day 1 |
| 4 | 1584 | 3.0 mg/kg J1D00015 | Single injection on day 1 |
| 5 | 553 | 3.0 mg/kg J1D00021 | Single injection on day 1 |
| 6 | 680 | 3.0 mg/kg J1D00022 | Single injection on day 1 |
| 7 | 1182 | 3.0 mg/kg J1D00005 | Single injection on day 1 |
| 8 | 746 | 3.0 mg/kg J1D00024 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agent J1D00008 (Group 2) included nucleotide sequences that were designed to inhibit expression of a PNPLA3 gene at position 2180 of the gene; the PNPLA3 RNAi agent J1D00014 (Group 3) included nucleotide sequences that were designed to inhibit expression of a PNPLA3 gene at position 886 of the gene; the PNPLA3 RNAi agent J1D00015 (Group 4) included nucleotide sequences that were designed to inhibit expression of a PNPLA3 gene at position 1584 of the gene; the PNPLA3 RNAi agent J1D00021 (Group 5) included nucleotide sequences that were designed to inhibit expression of a PNPLA3 gene at position 553 of the gene; the PNPLA3 RNAi agent J1D00022 (Group 6) included nucleotide sequences that were designed to inhibit expression of a PNPLA3 gene at position 680 of the gene; the PNPLA3 RNAi agent J1D00005 (Group 7) included nucleotide sequences that were designed to inhibit expression of a PNPLA3 gene at position 1182 of the gene; and the PNPLA3 RNAi agent J1D00024 (Group 8) included nucleotide sequences that were designed to inhibit expression of a PNPLA3 gene at position 746 of the gene. (See. e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 11 and 12:

TABLE 11

Average SEAP Normalized to Pre-Treatment (Day −1) in full length transcript PNPLA3-SEAP Mice from Example 4

| Group ID | Day 8 | | Day 15 | | Day 22 | |
|---|---|---|---|---|---|---|
| | Avg SEAP | Std Dev (+/−) | Avg SEAP | Std Dev (+/−) | Avg SEAP | Std Dev (+/−) |
| Group 1 (Saline vehicle) | 0.857 | 0.471 | 1.737 | 0.769 | 0.260 | 0.148 |
| Group 2 (3.0 mg/kg J1D00008) | 0.344 | 0.128 | 0.679 | 0.375 | 0.095 | 0.044 |
| Group 3 (3.0 mg/kg J1D00014) | 1.221 | 0.267 | 2.307 | 0.878 | 0.363 | 0.192 |
| Group 4 (3.0 mg/kg J1D00015) | 0.424 | 0.078 | 0.885 | 0.279 | 0.130 | 0.030 |
| Group 5 (3.0 mg/kg J1D00021) | 0.832 | 0.299 | 1.891 | 0.903 | 0.320 | 0.141 |
| Group 6 (3.0 mg/kg J1D00022) | 0.527 | 0.259 | 1.223 | 0.547 | 0.190 | 0.097 |
| Group 7 (3.0 mg/kg J1D00005) | 0.817 | 0.323 | 1.291 | 0.618 | 0.235 | 0.149 |
| Group 8 (3.0 mg/kg J1D00024) | 0.700 | 0.143 | 2.079 | 0.821 | 0.470 | 0.207 |

* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 12

Average SEAP Normalized to Pre-Treatment (Day −1) amd Vehicle Control in full length transcript PNPLA3-SEAP Mice from Example 4

| Group ID | Day 8 | | Day 15 | | Day 22 | |
|---|---|---|---|---|---|---|
| | Avg SEAP | Std Dev (+/−) | Avg SEAP | Avg (+/−) | Std Dev SEAP | Avg (+/−) |
| Group 1 (Saline vehicle) | 1.000 | 0.550 | 1.000 | 0.443 | 1.000 | 0.568 |
| Group 2 (3.0 mg/kg J1D00008) | 0.401 | 0.149 | 0.391 | 0.216 | 0.367 | 0.170 |
| Group 3 (3.0 mg/kg J1D00014) | 1.426 | 0.312 | 1.328 | 0.505 | 1.397 | 0.737 |
| Group 4 (3.0 mg/kg J1D00015) | 0.495 | 0.091 | 0.510 | 0.160 | 0.500 | 0.117 |
| Group 5 (3.0 mg/kg J1D00021) | 0.971 | 0.349 | 1.089 | 0.520 | 1.231 | 0.541 |
| Group 6 (3.0 mg/kg J1D00022) | 0.615 | 0.302 | 0.704 | 0.315 | 0.732 | 0.371 |
| Group 7 (3.0 mg/kg J1D00005) | 0.954 | 0.377 | 0.743 | 0.356 | 0.905 | 0.574 |
| Group 8 (3.0 mg/kg J1D00024) | 0.817 | 0.167 | 1.197 | 0.473 | 1.808 | 0.796 |

Example 5. In Vivo Testing of PNPLA3 RNAi Agents in PNPLA3-SEAP Mice

The PNPLA3-SEAP mouse model was used as described in Example 2, above, using the plasmid containing the truncated version of the human PNPLA3 transcript. At day 1, each mouse was given a single subcutaneous administration of 200 μl/20 g animal weight containing either 3.0 mg/kg (mpk) of a PNPLA3 RNAi agent formulated in saline, or vehicle control (saline with no RNAi agent), according to the following Table 13.

TABLE 13

Targeted Positions and Dosing Groups of Example 5

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 571 | 3.0 mg/kg J1D00012 | Single injection on day 1 |
| 3 | 571 | 3.0 mg/kg J1D00027 | Single injection on day 1 |
| 4 | 571 | 3.0 mg/kg J1D00028 | Single injection on day 1 |
| 5 | 571 | 3.0 mg/kg J1D00029 | Single injection on day 1 |
| 6 | 1179 | 3.0 mg/kg J1D00011 | Single injection on day 1 |
| 7 | 1179 | 3.0 mg/kg J1D00017 | Single injection on day 1 |
| 8 | 1586 | 3.0 mg/kg J1D00004 | Single injection on day 1 |
| 9 | 1586 | 3.0 mg/kg J1D00003 | Single injection on day 1 |
| 10 | 1586 | 3.0 mg/kg J1D00041 | Single injection on day 1 |
| 11 | 2180 | 3.0 mg/kg J1D00008 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agents J1D00012 (Group 2), J1D00027 (Group 3), J1D00028 (Group 4), J1D00029 (Group 5) each included nucleotide sequences that were designed to inhibit expression of a PNPLA3 gene at position 571 of the gene; the PNPLA3 RNAi agents J1D00011 (Group 6) and J1D00017 (Group 7) included nucleotide sequences that were designed to inhibit expression of a PNPLA3 gene at position 1179 of the gene; the PNPLA3 RNAi agents J1D00004 (Group 8), J1D00003 (Group 9), and J1D00041 (Group 10) included nucleotide sequences that were designed to inhibit expression of a PNPLA3 gene at position 1586 of the gene; and the PNPLA3 RNAi agent J1D00008 (Group 11) included nucleotide sequences that were designed to inhibit expression of a PNPLA3 gene at position 2180 of the gene. (See. e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 14 and 15:

TABLE 14

Average SEAP Normalized to Pre-Treatment (Day −1) in truncated transcript PNPLA3-SEAP Mice from Example 5

| | Day 15 | | Day 22 | | Day 29 | |
|---|---|---|---|---|---|---|
| Group ID | Avg SEAP | Std Dev (+/−) | Avg SEAP | Avg (+/−) | Std Dev SEAP | Avg (+/−) |
| Group 1 (Saline vehicle) | 0.746 | 0.164 | 0.446 | 0.258 | 0.677 | 0.725 |
| Group 2 (3.0 mg/kg J1D00012) | 0.109 | 0.056 | 0.130 | 0.063 | 0.235 | 0.151 |
| Group 3 (3.0 mg/kg J1D00027) | 0.132 | 0.084 | 0.199 | 0.126 | 0.249 | 0.190 |
| Group 4 (3.0 mg/kg J1D00028) | 0.194 | 0.083 | 0.294 | 0.074 | 0.328 | 0.089 |
| Group 5 (3.0 mg/kg J1D00029) | 0.108 | 0.035 | 0.090 | 0.033 | 0.161 | 0.107 |
| Group 6 (3.0 mg/kg J1D00011) | 0.192 | 0.138 | 0.175 | 0.061 | 0.279 | 0.069 |
| Group 7 (3.0 mg/kg J1D00017) | 0.085 | 0.049 | 0.151 | 0.054 | 0.317 | 0.088 |
| Group 8 (3.0 mg/kg J1D00004) | 0.066 | 0.094 | 0.083 | 0.120 | 0.141 | 0.198 |
| Group 9 (3.0 mg/kg J1D00003) | 0.026 | 0.007 | 0.024 | 0.007 | 0.039 | 0.008 |
| Group 10 (3.0 mg/kg J1D00041) | 0.037 | 0.029 | 0.060 | 0.039 | 0.073 | 0.018 |
| Group 11 (3.0 mg/kg J1D00008) | 0.091 | 0.071 | 0.216 | 0.235 | 0.285 | 0.219 |

* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 15

Average SEAP Normalized to Pre-Treatment (Day −1) and Vehicle Control in truncated transcript PNPLA3-SEAP Mice from Example 5

| | Day 8 | | Day 15 | | Day 22 | | Day 29 | |
|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.000 | 0.224 | 1.000 | 0.220 | 1.000 | 0.578 | 1.000 | 1.071 |
| Group 2 (3.0 mg/kg J1D00012) | 0.194 | 0.094 | 0.146 | 0.075 | 0.290 | 0.142 | 0.346 | 0.222 |
| Group 3 (3.0 mg/kg J1D00027) | 0.172 | 0.134 | 0.177 | 0.113 | 0.445 | 0.283 | 0.368 | 0.280 |
| Group 4 (3.0 mg/kg J1D00028) | 0.246 | 0.101 | 0.260 | 0.112 | 0.659 | 0.167 | 0.484 | 0.131 |
| Group 5 (3.0 mg/kg J1D00029) | 0.225 | 0.117 | 0.145 | 0.047 | 0.203 | 0.074 | 0.237 | 0.158 |
| Group 6 (3.0 mg/kg J1D00011) | 0.383 | 0.179 | 0.257 | 0.185 | 0.391 | 0.136 | 0.412 | 0.101 |

TABLE 15-continued

Average SEAP Normalized to Pre-Treatment (Day −1) and Vehicle Control in truncated transcript PNPLA3-SEAP Mice from Example 5

|  | Day 8 | | Day 15 | | Day 22 | | Day 29 | |
| --- | --- | --- | --- | --- | --- | --- | --- | --- |
| Group ID | Avg SEAP | Std Dev (+/−) | Avg SEAP | Std Dev (+/−) | Avg SEAP | Std Dev (+/−) | Avg SEAP | Std Dev (+/−) |
| Group 7 (3.0 mg/kg J1D00017) | 0.265 | 0.147 | 0.114 | 0.066 | 0.339 | 0.120 | 0.467 | 0.129 |
| Group 8 (3.0 mg/kg J1D00004) | 0.095 | 0.075 | 0.089 | 0.126 | 0.186 | 0.268 | 0.208 | 0.293 |
| Group 9 (3.0 mg/kg J1D00003) | 0.084 | 0.023 | 0.035 | 0.010 | 0.054 | 0.015 | 0.057 | 0.012 |
| Group 10 (3.0 mg/kg J1D00041) | 0.094 | 0.041 | 0.048 | 0.037 | 0.126 | 0.081 | 0.102 | 0.025 |
| Group 11 (3.0 mg/kg J1D00008) | 0.169 | 0.057 | 0.119 | 0.092 | 0.451 | 0.491 | 0.397 | 0.305 |

Each of the PNPLA3 RNAi agents in each of the dosing groups (i.e., Groups 2 through 11) showed reduction in SEAP as compared to the vehicle control (Group 1) at all measured timepoints.

Example 6. In Vivo Testing of PNPLA3 RNAi Agents in PNPLA3-SEAP Mice

The PNPLA3-SEAP mouse model was used as described in Example 2, above, using the plasmid containing the truncated version of the human PNPLA3 transcript. At day 1, each mouse was given a single subcutaneous administration of 200 μl/20 g animal weight containing either 3.0 mg/kg (mpk) of a PNPLA3 RNAi agent formulated in saline, or vehicle control (saline with no RNAi agent), according to the following Table 16.

TABLE 16

Targeted Positions and Dosing Groups of Example 6

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 2180 | 3.0 mg/kg J1D00008 | Single injection on day 1 |
| 3 | 2180 | 3.0 mg/kg J1D00046 | Single injection on day 1 |
| 4 | 2180 | 3.0 mg/kg J1D00047 | Single injection on day 1 |
| 5 | 2180 | 3.0 mg/kg J1D00048 | Single injection on day 1 |
| 6 | 1179 | 3.0 mg/kg J1D00011 | Single injection on day 1 |
| 7 | 1179 | 3.0 mg/kg J1D00043 | Single injection on day 1 |
| 8 | 1179 | 3.0 mg/kg J1D00044 | Single injection on day 1 |
| 9 | 1179 | 3.0 mg/kg J1D00045 | Single injection on day 1 |
| 10 | 544 | 3.0 mg/kg J1D00020 | Single injection on day 1 |
| 11 | 1195 | 3.0 mg/kg J1D00026 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agents J1D00008 (Group 2), J1D00046 (Group 3), J1D00047 (Group 4), and J1D00048 (Group 5) each included nucleotide sequences that were designed to inhibit expression of a PNPLA3 gene at position 2180 of the gene; the PNPLA3 RNAi agents J1D00011 (Group 6), J1D00043 (Group 7), J1D00044 (Group 8), and J1D00045 (Group 9) included nucleotide sequences that were designed to inhibit expression of a PNPLA3 gene at position 1179 of the gene; the PNPLA3 RNAi agent J1D00020 (Group 10) included nucleotide sequences that were designed to inhibit expression of a PNPLA3 gene at position 544 of the gene; and the PNPLA3 RNAi agent J1D00026 (Group 11) included nucleotide sequences that were designed to inhibit expression of a PNPLA3 gene at position 1195 of the gene. (See. e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 17 and 18:

TABLE 17

Average SEAP Normalized to Pre-Treatment (Day −1) in truncated transcript PNPLA3-SEAP Mice from Example 6

|  | Day 8 | | Day 15 | | Day 22 | | Day 29 | |
| --- | --- | --- | --- | --- | --- | --- | --- | --- |
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.434 | 0.237 | 1.189 | 0.385 | 0.616 | 0.022 | 1.323 | 0.693 |
| Group 2 (3.0 mg/kg J1D00008) | 0.328 | 0.215 | 0.356 | 0.186 | 0.329 | 0.129 | 1.342 | 0.529 |
| Group 3 (3.0 mg/kg J1D00046) | 0.254 | 0.240 | 0.356 | 0.478 | 0.303 | 0.338 | 0.370 | 0.210 |
| Group 4 (3.0 mg/kg J1D00047) | 0.219 | 0.080 | 0.127 | 0.042 | 0.106 | 0.017 | 0.488 | 0.072 |
| Group 5 (3.0 mg/kg J1D00048) | 0.153 | 0.055 | 0.158 | 0.064 | 0.175 | 0.078 | 0.463 | 0.126 |
| Group 6 (3.0 mg/kg J1D00011) | 0.782 | 0.468 | 0.874 | 0.597 | 0.461 | 0.361 | 0.714 | 0.582 |
| Group 7 (3.0 mg/kg J1D00043) | 0.713 | 0.539 | 0.981 | 0.784 | 0.939 | 0.725 | 1.364 | 0.975 |
| Group 8 (3.0 mg/kg J1D00044) | 0.683 | 0.113 | 0.539 | 0.143 | 0.355 | 0.096 | 0.891 | 0.217 |
| Group 9 (3.0 mg/kg J1D00045) | 0.479 | 0.309 | 0.547 | 0.101 | 0.383 | 0.201 | 0.935 | 0.361 |

TABLE 17-continued

Average SEAP Normalized to Pre-Treatment (Day −1) in truncated
transcript PNPLA3-SEAP Mice from Example 6

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 10 (3.0 mg/kg J1D00020) | 0.726 | 0.575 | 0.906 | 0.856 | 0.506 | 0.376 | 1.255 | 1.244 |
| Group 11 (3.0 mg/kg J1D00026) | 0.590 | 0.431 | 0.395 | 0.434 | 0.351 | 0.322 | 0.703 | 0.293 |

* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 18

Average SEAP Normalized to Pre-Treatment (Day −1) and Vehicle Control in truncated
transcript PNPLA3-SEAP Mice from Example 6

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline vehicle) | 1.000 | 0.165 | 1.000 | 0.323 | 1.000 | 0.035 | 1.000 | 0.524 |
| Group 2 (3.0 mg/kg J1D00008) | 0.229 | 0.150 | 0.299 | 0.156 | 0.535 | 0.209 | 1.014 | 0.400 |
| Group 3 (3.0 mg/kg J1D00046) | 0.177 | 0.167 | 0.299 | 0.402 | 0.492 | 0.549 | 0.280 | 0.159 |
| Group 4 (3.0 mg/kg J1D00047) | 0.153 | 0.056 | 0.107 | 0.035 | 0.173 | 0.028 | 0.369 | 0.055 |
| Group 5 (3.0 mg/kg J1D00048) | 0.107 | 0.038 | 0.133 | 0.054 | 0.283 | 0.127 | 0.350 | 0.095 |
| Group 6 (3.0 mg/kg J1D00011) | 0.545 | 0.326 | 0.735 | 0.502 | 0.749 | 0.586 | 0.540 | 0.440 |
| Group 7 (3.0 mg/kg J1D00043) | 0.497 | 0.375 | 0.825 | 0.660 | 1.524 | 1.177 | 1.031 | 0.737 |
| Group 8 (3.0 mg/kg J1D00044) | 0.476 | 0.079 | 0.453 | 0.120 | 0.576 | 0.157 | 0.674 | 0.164 |
| Group 9 (3.0 mg/kg J1D00045) | 0.334 | 0.215 | 0.460 | 0.085 | 0.621 | 0.327 | 0.706 | 0.272 |
| Group 10 (3.0 mg/kg J1D00020) | 0.506 | 0.401 | 0.762 | 0.720 | 0.822 | 0.611 | 0.949 | 0.940 |
| Group 11 (3.0 mg/kg J1D00026) | 0.411 | 0.300 | 0.333 | 0.365 | 0.569 | 0.523 | 0.531 | 0.222 |

Example 7. In Vivo Testing of PNPLA3 RNAi Agents in PNPLA3-SEAP Mice

The PNPLA3-SEAP mouse model was used as described in Example 2, above, using the plasmid containing the truncated version of the human PNPLA3 transcript. At day 1, each mouse was given a single subcutaneous administration of 200 µl/20 g animal weight containing either 1.5 mg/kg (mpk) of a PNPLA3 RNAi agent formulated in saline, or vehicle control (saline with no RNAi agent), according to the following Table 19.

TABLE 19

Targeted Positions and Dosing Groups of Example 7

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 2180 | 1.5 mg/kg J1D00008 | Single injection on day 1 |
| 3 | 538 | 1.5 mg/kg J1D00018 | Single injection on day 1 |
| 4 | 538 | 1.5 mg/kg J1D00019 | Single injection on day 1 |
| 5 | 687 | 1.5 mg/kg J1D00013 | Single injection on day 1 |
| 6 | 751 | 1.5 mg/kg J1D00006 | Single injection on day 1 |
| 7 | 751 | 1.5 mg/kg J1D00007 | Single injection on day 1 |
| 8 | 1181 | 1.5 mg/kg J1D00035 | Single injection on day 1 |
| 9 | 685 | 1.5 mg/kg J1D00033 | Single injection on day 1 |
| 10 | 373 | 1.5 mg/kg J1D00032 | Single injection on day 1 |
| 11 | 1837 | 1.5 mg/kg J1D00040 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agent J1D00008 (Group 2) included nucleotide sequences that were designed to inhibit expression of a PNPLA3 gene at position 2180 of the gene; the PNPLA3 RNAi agents J1D000018 (Group 3) and J1D00019 (Group 4) included nucleotide sequences that were designed to inhibit expression of a PNPLA3 gene at position 538 of the gene; the PNPLA3 RNAi agent J1D00013 (Group 5) included nucleotide sequences that were designed to inhibit expression of a PNPLA3 gene at position 687 of the gene; the PNPLA3 RNAi agents J1D000006 (Group 6) and J1D00007 (Group 7) included nucleotide sequences that were designed to inhibit expression of a PNPLA3 gene at position 751 of the gene; the PNPLA3 RNAi agent J1D00035 (Group 8) included nucleotide sequences that were designed to inhibit expression of a PNPLA3 gene at position 1181 of the gene; the PNPLA3 RNAi agent J1D00033 (Group 9) included nucleotide sequences that were designed to inhibit expression of a PNPLA3 gene at position 685 of the gene; the PNPLA3 RNAi agent J1D00032 (Group 10) included nucleotide sequences that were designed to inhibit expression of a PNPLA3 gene at position 373 of the gene; and the PNPLA3 RNAi agent J1D00040 (Group 11) included nucleotide sequences that were designed to inhibit expression of a PNPLA3 gene at position 1837 of the gene. (See, e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 20 and 21:

TABLE 20

Average SEAP Normalized to Pre-Treatment (Day −1) in truncated transcript in PNPLA3-SEAP Mice from Example 7

| Group ID | Day 8 | | Day 15 | | Day 22 | | Day 29 | |
| --- | --- | --- | --- | --- | --- | --- | --- | --- |
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 0.302 | 0.188 | 0.192 | 0.105 | 0.209 | 0.194 | 0.167 | 0.145 |
| Group 2 (1.5 mg/kg J1D00008) | 0.083 | 0.035 | 0.113 | 0.105 | 0.127 | 0.105 | 0.148 | 0.119 |
| Group 3 (1.5 mg/kg J1D00018) | 0.505 | 0.344 | 0.561 | 0.425 | 0.455 | 0.295 | 0.424 | 0.283 |
| Group 4 (1.5 mg/kg J1D00019) | 0.293 | 0.152 | 0.329 | 0.169 | 0.337 | 0.215 | 0.291 | 0.203 |
| Group 5 (1.5 mg/kg J1D00013) | 0.101 | 0.099 | 0.084 | 0.065 | 0.076 | 0.061 | 0.110 | 0.115 |
| Group 6 (1.5 mg/kg J1D00006) | 0.221 | 0.140 | 0.265 | 0.265 | 0.218 | 0.232 | 0.126 | 0.191 |
| Group 7 (1.5 mg/kg J1D00007) | 0.257 | 0.102 | 0.237 | 0.172 | 0.162 | 0.082 | 0.177 | 0.088 |
| Group 8 (1.5 mg/kg J1D00035) | 0.548 | 0.504 | 0.344 | 0.278 | 0.406 | 0.361 | 0.413 | 0.395 |
| Group 9 (1.5 mg/kg J1D00033) | 0.481 | 0.154 | 0.270 | 0.126 | 0.204 | 0.114 | 0.258 | 0.115 |
| Group 10 (1.5 mg/kg J1D00032) | 0.687 | 0.145 | 0.831 | 0.243 | 0.639 | 0.270 | 0.464 | 0.093 |
| Group 11 (1.5 mg/kg J1D00040) | 0.237 | 0.101 | 0.190 | 0.085 | 0.182 | 0.100 | 0.162 | 0.137 |

\* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 21

Average SEAP Normalized to Pre-Treatment (Day −1) and Vehicle Control in truncated transcript in PNPLA3-SEAP Mice from Example 7

| Group ID | Day 8 | | Day 15 | | Day 22 | | Day 29 | |
| --- | --- | --- | --- | --- | --- | --- | --- | --- |
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.000 | 0.621 | 1.000 | 0.549 | 1.000 | 0.927 | 1.000 | 0.868 |
| Group 2 (1.5 mg/kg J1D00008) | 0.275 | 0.117 | 0.588 | 0.547 | 0.606 | 0.503 | 0.887 | 0.710 |
| Group 3 (1.5 mg/kg J1D00018) | 1.673 | 1.139 | 2.924 | 2.217 | 2.175 | 1.408 | 2.536 | 1.691 |
| Group 4 (1.5 mg/kg J1D00019) | 0.969 | 0.502 | 1.713 | 0.879 | 1.611 | 1.028 | 1.737 | 1.214 |
| Group 5 (1.5 mg/kg J1D00013) | 0.335 | 0.327 | 0.440 | 0.341 | 0.364 | 0.293 | 0.657 | 0.686 |
| Group 6 (1.5 mg/kg J1D00006) | 0.730 | 0.462 | 1.383 | 1.379 | 1.043 | 1.108 | 0.753 | 1.144 |
| Group 7 (1.5 mg/kg J1D00007) | 0.850 | 0.339 | 1.234 | 0.894 | 0.772 | 0.393 | 1.057 | 0.527 |
| Group 8 (1.5 mg/kg J1D00035) | 1.814 | 1.669 | 1.794 | 1.451 | 1.939 | 1.724 | 2.471 | 2.365 |
| Group 9 (1.5 mg/kg J1D00033) | 1.592 | 0.509 | 1.409 | 0.658 | 0.974 | 0.545 | 1.541 | 0.685 |
| Group 10 (1.5 mg/kg J1D00032) | 2.274 | 0.479 | 4.330 | 1.265 | 3.050 | 1.292 | 2.772 | 0.559 |
| Group 11 (1.5 mg/kg J1D00040) | 0.784 | 0.335 | 0.991 | 0.445 | 0.870 | 0.476 | 0.967 | 0.817 |

Example 8. In Vivo Testing of PNPLA3 RNAi Agents in PNPLA3-SEAP Mice

The PNPLA3-SEAP mouse model was used as described in Example 2, above, using the plasmid containing the truncated version of the human PNPLA3 transcript. At day 1, each mouse was given a single subcutaneous administration of 200 μl/20 g animal weight containing either 1.5 mg/kg (mpk) of a PNPLA3 RNAi agent formulated in saline, or vehicle control (saline with no RNAi agent), according to the following Table 22.

TABLE 22

Targeted Positions and Dosing Groups of Example 8

| Group | Targeted Gene Position (within SEQ ID NO: 1) | RNAi Agent and Dose | Dosing Regimen |
| --- | --- | --- | --- |
| 1 | N/A | Saline (no RNAi agent) | Single injection on day 1 |
| 2 | 2180 | 1.5 mg/kg J1D00008 | Single injection on day 1 |
| 3 | 2180 | 1.5 mg/kg J1D00074 | Single injection on day 1 |
| 4 | 2180 | 1.5 mg/kg J1D00075 | Single injection on day 1 |
| 5 | 2180 | 1.5 mg/kg J1D00076 | Single injection on day 1 |
| 6 | 2180 | 1.5 mg/kg J1D00077 | Single injection on day 1 |
| 7 | 2180 | 1.5 mg/kg J1D00078 | Single injection on day 1 |

TABLE 22-continued

Targeted Positions and Dosing Groups of Example 8

| Group | Targeted Gene Position (within SEQ ID NO: 1) | RNAi Agent and Dose | Dosing Regimen |
|---|---|---|---|
| 8 | 2180 | 1.5 mg/kg J1D00048 | Single injection on day 1 |
| 9 | 2180 | 1.5 mg/kg J1D00079 | Single injection on day 1 |
| 10 | 2180 | 1.5 mg/kg J1D00080 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agents in each Group (i.e., Groups 2-10) each included nucleotide sequences that were designed to inhibit expression of a PNPLA3 gene at position 2180 of the gene. (See. e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 23 and 24:

TABLE 23

Average SEAP Normalized to Pre-Treatment (Day −1) in truncated transcript PNPLA3-SEAP Mice from Example 8

| | Day 8 | | Day 15 | | Day 22 | | Day 29 | |
|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.134 | 0.219 | 0.851 | 0.295 | 0.826 | 0.637 | 0.759 | 0.471 |
| Group 2 (1.5 mg/kg J1D00008) | 0.367 | 0.080 | 0.267 | 0.138 | 0.374 | 0.202 | 0.410 | 0.309 |
| Group 3 (1.5 mg/kg J1D00074) | 0.205 | 0.063 | 0.211 | 0.072 | 0.276 | 0.108 | 0.396 | 0.182 |
| Group 4 (1.5 mg/kg J1D00075) | 0.705 | 0.202 | 0.673 | 0.370 | 0.634 | 0.415 | 0.571 | 0.427 |
| Group 5 (1.5 mg/kg J1D00076) | 0.484 | 0.312 | 0.307 | 0.200 | 0.315 | 0.301 | 0.260 | 0.189 |
| Group 6 (1.5 mg/kg J1D00077) | 0.445 | 0.293 | 0.290 | 0.186 | 0.400 | 0.329 | 0.310 | 0.207 |
| Group 7 (1.5 mg/kg J1D00078) | 0.190 | 0.099 | 0.153 | 0.122 | 0.289 | 0.292 | 0.291 | 0.255 |
| Group 8 (1.5 mg/kg J1D00048) | 0.341 | 0.194 | 0.389 | 0.306 | 0.345 | 0.089 | 0.418 | 0.232 |
| Group 9 (1.5 mg/kg J1D00079) | 0.213 | 0.105 | 0.174 | 0.189 | 0.285 | 0.249 | 0.311 | 0.248 |
| Group 10 (1.5 mg/kg J1D00080) | 0.270 | 0.143 | 0.277 | 0.159 | 0.439 | 0.309 | 0.525 | 0.411 |

\* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 24

Average SEAP Normalized to Pre-Treatment (Day −1) and Vehicle Control in truncated transcript PNPLA3-SEAP Mice from Example 8

| | Day 8 | | Day 15 | | Day 22 | | Day 29 | |
|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.000 | 0.193 | 1.000 | 0.347 | 1.000 | 0.771 | 1.000 | 0.620 |
| Group 2 (1.5 mg/kg J1D00008) | 0.324 | 0.071 | 0.314 | 0.162 | 0.453 | 0.245 | 0.540 | 0.408 |
| Group 3 (1.5 mg/kg J1D00074) | 0.181 | 0.056 | 0.248 | 0.085 | 0.334 | 0.131 | 0.522 | 0.240 |
| Group 4 (1.5 mg/kg J1D00075) | 0.621 | 0.178 | 0.791 | 0.435 | 0.768 | 0.503 | 0.752 | 0.563 |
| Group 5 (1.5 mg/kg J1D00076) | 0.426 | 0.275 | 0.361 | 0.235 | 0.382 | 0.365 | 0.343 | 0.250 |
| Group 6 (1.5 mg/kg J1D00077) | 0.393 | 0.258 | 0.341 | 0.219 | 0.484 | 0.398 | 0.409 | 0.273 |
| Group 7 (1.5 mg/kg J1D00078) | 0.168 | 0.087 | 0.180 | 0.144 | 0.350 | 0.353 | 0.384 | 0.337 |
| Group 8 (1.5 mg/kg J1D00048) | 0.300 | 0.171 | 0.457 | 0.359 | 0.418 | 0.108 | 0.551 | 0.306 |
| Group 9 (1.5 mg/kg J1D00079) | 0.188 | 0.093 | 0.204 | 0.222 | 0.345 | 0.301 | 0.410 | 0.327 |
| Group 10 (1.5 mg/kg J1D00080) | 0.238 | 0.126 | 0.326 | 0.187 | 0.531 | 0.374 | 0.692 | 0.542 |

Each of the PNPLA3 RNAi agents in each of the dosing groups (i.e., Groups 2 through 10) showed reduction in SEAP as compared to the vehicle control (Group 1) at all measured timepoints.

Example 9. In Vivo Testing of PNPLA3 RNAi Agents in PNPLA3-SEAP Mice

The PNPLA3-SEAP mouse model was used as described in Example 2, above, using the plasmid containing the truncated version of the human PNPLA3 transcript. At day 1, each mouse was given a single subcutaneous administration of 200 μl/20 g animal weight containing 1.5 mg/kg (mpk) of a PNPLA3 RNAi agent formulated in saline, or vehicle control (saline with no RNAi agent), which included the dosing groups according to the following Table 25.

TABLE 25

Targeted Positions and Dosing Groups of Example 9

| Group | Targeted Gene Position (within SEQ ID NO: 1) | RNAi Agent and Dose | Dosing Regimen |
|---|---|---|---|
| 1 | N/A | Saline (no RNAi agent) | Single injection on day 1 |
| 2 | 2180 | 1.5 mg/kg J1D00008 | Single injection on day 1 |
| 3 | 887 | 1.5 mg/kg J1D00081 | Single injection on day 1 |
| 4 | 1185 | 1.5 mg/kg J1D00083 | Single injection on day 1 |
| 5 | 1191 | 1.5 mg/kg J1D00084 | Single injection on day 1 |
| 6 | 1191 | 1.5 mg/kg J1D00085 | Single injection on day 1 |
| 7 | 1746 | 1.5 mg/kg J1D00087 | Single injection on day 1 |
| 8 | 1173 | 1.5 mg/kg J1D00082 | Single injection on day 1 |

Each of the PNPLA3 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-5 for specific modifications and structure information related to the PNPLA3 RNAi agents, including (NAG37)s ligand). The PNPLA3 RNAi agent J1D00008 (Group 2) included nucleotide sequences that were designed to inhibit expression of a PNPLA3 gene at position 2180 of the gene; the PNPLA3 RNAi agent J1D00081 (Group 3) included nucleotide sequences that were designed to inhibit expression of a PNPLA3 gene at position 887 of the gene; the PNPLA3 RNAi agent J1D00083 (Group 4) included nucleotide sequences that were designed to inhibit expression of a PNPLA3 gene at position 1185 of the gene; the PNPLA3 RNAi agents J1D00084 (Group 5) and J1D00085 (Group 6) each included nucleotide sequences that were designed to inhibit expression of a PNPLA3 gene at position 1191 of the gene; the PNPLA3 RNAi agent J1D00087 (Group 7) included nucleotide sequences that were designed to inhibit expression of a PNPLA3 gene at position 1746 of the gene; and the PNPLA3 RNAi agent J1D00082 (Group 8) included nucleotide sequences that were designed to inhibit expression of a PNPLA3 gene at position 1173 of the gene. (See. e.g., SEQ ID NO:1 and Table 2 for the PNPLA3 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, day 22, and day 29, and SEAP expression levels were determined pursuant to the procedure set forth in Example 2, above. Data from the experiment are shown in the following Tables 26 and 27:

TABLE 26

Average SEAP Normalized to Pre-Treatment (Day −1) in truncated transcript PNPLA3-SEAP Mice from Example 9

| Group ID | Day 8 | | Day 15 | | Day 22 | | Day 29 | |
|---|---|---|---|---|---|---|---|---|
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 0.668 | 0.265 | 0.578 | 0.386 | 0.522 | 0.289 | 1.227 | 1.269 |
| Group 2 (1.5 mg/kg J1D00008) | 0.236 | 0.177 | 0.149 | 0.116 | 0.448 | 0.343 | 0.822 | 0.725 |
| Group 3 (1.5 mg/kg J1D00081) | 0.339 | 0.160 | 0.254 | 0.179 | 0.320 | 0.192 | 0.529 | 0.330 |
| Group 4 (1.5 mg/kg J1D00083) | 0.524 | 0.404 | 0.332 | 0.304 | 0.375 | 0.227 | 0.564 | 0.517 |
| Group 5 (1.5 mg/kg J1D00084) | 0.304 | 0.200 | 0.158 | 0.142 | 0.185 | 0.167 | 0.343 | 0.364 |
| Group 6 (1.5 mg/kg J1D00085) | 0.506 | 0.241 | 0.320 | 0.241 | 0.355 | 0.220 | 0.718 | 0.497 |
| Group 7 (1.5 mg/kg J1D00087) | 0.170 | 0.069 | 0.122 | 0.092 | 0.252 | 0.102 | 0.549 | 0.028 |
| Group 8 (1.5 mg/kg J1D00082) | 0.508 | 0.302 | 0.454 | 0.308 | 0.488 | 0.361 | 0.914 | 0.661 |

* As noted in Example 2, above, the gradual reduction in SEAP in the vehicle control group (Group 1) over time is due to the loss of the SEAP reporter gene in the cells of the mice due to the natural cell replication in the animals, and is not the result of any inhibitory compound.

TABLE 27

Average SEAP Normalized to Pre-Treatment (Day −1) amd Vehicle Control in truncated transcript PNPLA3-SEAP Mice from Example 9

| Group ID | Day 8 | | Day 15 | | Day 22 | | Day 29 | |
|---|---|---|---|---|---|---|---|---|
| | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.000 | 0.397 | 1.000 | 0.668 | 1.000 | 0.553 | 1.000 | 1.034 |
| Group 2 (1.5 mg/kg J1D00008) | 0.353 | 0.265 | 0.259 | 0.201 | 0.860 | 0.658 | 0.669 | 0.591 |
| Group 3 (1.5 mg/kg J1D00081) | 0.507 | 0.240 | 0.440 | 0.310 | 0.613 | 0.369 | 0.431 | 0.269 |
| Group 4 (1.5 mg/kg J1D00083) | 0.784 | 0.604 | 0.574 | 0.526 | 0.719 | 0.435 | 0.459 | 0.421 |
| Group 5 (1.5 mg/kg J1D00084) | 0.455 | 0.300 | 0.273 | 0.246 | 0.355 | 0.320 | 0.279 | 0.297 |
| Group 6 (1.5 mg/kg J1D00085) | 0.757 | 0.360 | 0.555 | 0.418 | 0.681 | 0.421 | 0.585 | 0.405 |

TABLE 27-continued

Average SEAP Normalized to Pre-Treatment (Day −1) amd Vehicle Control in truncated transcript PNPLA3-SEAP Mice from Example 9

| Group ID | Day 8 | | Day 15 | | Day 22 | | Day 29 | |
|---|---|---|---|---|---|---|---|---|
| | Avg SEAP | Std Dev (+/−) | Avg SEAP | Std Dev (+/−) | Avg SEAP | Std Dev (+/−) | Avg SEAP | Std Dev (+/−) |
| Group 7 (1.5 mg/kg J1D00087) | 0.255 | 0.103 | 0.211 | 0.160 | 0.483 | 0.195 | 0.448 | 0.022 |
| Group 8 (1.5 mg/kg J1D00082) | 0.759 | 0.452 | 0.786 | 0.534 | 0.935 | 0.693 | 0.745 | 0.539 |

Example 10. In Vivo Testing of PNPLA3 RNAi Agents in Cynomolgus Monkeys

PNPLA3 RNAi agents J1D00003, J1D00008, and J1D00017 were evaluated in cynomolgus monkeys (cynos). On days 1 and 43, four cynos for each group (n=4) were administered a subcutaneous injection of 0.4 mL/kg (approximately 1.5 mL volume, depending on animal mass) containing 4.0 mg/kg (10 mg/mL) of the respective PNPLA3 RNAi agent, formulated in saline, or the saline vehicle alone with no RNAi agent to serve as a control (See Table 28 below).

TABLE 28

Targeted Positions and Dosing Groups of Example 10

| Group | Targeted Gene Position (within SEQ ID NO: 1) | RNAi Agent and Dose | Dosing Regimen (on days 1 and 43) |
|---|---|---|---|
| 1 | N/A | Saline (no RNAi agent) | Single subcutaneous injection |
| 2 | 1586 | 4.0 mg/kg J1D00003 | Single subcutaneous injection |
| 3 | 2180 | 4.0 mg/kg J1D00008 | Single subcutaneous injection |
| 4 | 1179 | 4.0 mg/kg J1D00017 | Single subcutaneous injection |

The PNPLA3 RNAi agents included modified nucleotides and a tridentate N-acetyl-galactosamine-containing targeting ligand ((NAG37)s) conjugated to the 5'-terminal end of the sense strand, as shown in Tables 3-6. PNPLA3 RNAi agent J1D00003 (Group 2) included nucleotide sequences that were designed to inhibit expression of a PNPLA3 gene at position 1586 of the gene; PNPLA3 RNAi agent J1D00008 (Group 3) included nucleotide sequences that were designed to inhibit expression of a PNPLA3 gene at position 2180 of the gene; and PNPLA3 RNAi agent J1D00017 (Group 4) included nucleotide sequences that were designed to inhibit expression of a PNPLA3 gene at position 1179 of the gene.

On days −13 (pre-dose), 15, 29, 57, and 76, liver biopsies were taken. On the date of each biopsy collection, cynos were anesthetized and laparoscopy was used to extract two liver tissue samples approximately 80 mg to 120 mg each. The biopsy samples were then homogenized, and levels of PNPLA3 mRNA in the cyno livers were measured by RT-qPCR. Resulting values were then normalized to the pre-dose (in this case, at day −13) PNPLA3 mRNA measurements. The resulting mRNA data are reflected in the following Table 29:

TABLE 29

PNPLA3 mRNA Levels Normalized to Pre-Dose (Day −13) from Example 10 for Each Group (n = 4)

| | Day 15 | | | Day 29 | | |
|---|---|---|---|---|---|---|
| | Relative PNPLA3 mRNA Expression | Low Error | High Error | Relative PNPLA3 mRNA Expression | Low Error | High Error |
| Group 1: Saline | 0.768 | 0.144 | 0.178 | 0.616 | 0.138 | 0.178 |
| Group 2: J1D00003 | 0.624 | 0.222 | 0.345 | 0.468 | 0.178 | 0.287 |

TABLE 29-continued

PNPLA3 mRNA Levels Normalized to Pre-Dose (Day −13) from Example 10 for Each Group (n = 4)

| Group 3: J1D00008 | 0.486 | 0.065 | 0.074 | 0.455 | 0.120 | 0.164 |
|---|---|---|---|---|---|---|
| Group 4: J1D00017 | 0.671 | 0.211 | 0.307 | 0.517 | 0.088 | 0.105 |

| | Day 57 | | | Day 76 | | |
|---|---|---|---|---|---|---|
| | Relative PNPLA3 mRNA Expression | Low Error | High Error | Relative PNPLA3 mRNA Expression | Low Error | High Error |
| Group 1: Saline | 1.037 | 0.313 | 0.448 | 0.569 | 0.121 | 0.153 |
| Group 2: J1D00003 | 0.449 | 0.176 | 0.290 | 0.649 | 0.321 | 0.636 |
| Group 3: J1D00008 | 0.526 | 0.062 | 0.070 | 0.631 | 0.085 | 0.099 |
| Group 4: J1D00017 | 0.795 | 0.217 | 0.298 | 0.824 | 0.221 | 0.301 |

Example 11. In Vivo Testing of PNPLA3 RNAi Agent J1D00008 in Cynomolgus Monkeys The objective of this study was to evaluate RNAi agent J1D00008 for both depth and duration of knockdown of WT PNPLA3 mRNA in the liver of cynomolgus monkeys (cynos). Knockdown was normalized per animal to baseline measures obtained from liver biopsies performed prior to dosing.

Materials and Methods

Study 1: Cynos were grouped by body weight (2-5 kg) into a saline- (group 1) or RNA-treated group (groups 2-4), n=4 per group. Cynos were dosed twice on days 1 and 43 subcutaneously at 4 mg/kg in 0.4 ml/kg saline. Cynos were fasted overnight for at least 12 hours prior to biopsy and blood draw. Liver biopsy samples were collected from all animals pre-dose and on test days 15, 29, 57, and 76. For each animal, liver biopsy samples (2×, approximately 100 mg each) were collected for PNPLA3 mRNA quantification by qPCR and in situ hybridization (ISH). Blood was collected from a femoral vein from each animal pre-dose and post-dose on Days 15, 29, 57, and 76. For all animals, groups, and timepoints, RNA was isolated from the left lateral liver lobe to perform qRT-PCR, data were normalized to a house-keeping gene (ARFGAP2), and relative expression was compared to baseline/pre-dose biopsy. At the end of the study, PNPLA3 expression was measured in left and right lateral and median liver lobes from groups 1 and 3 to confirm that expression did not vary from lobe to lobe, and that the left lateral lobe was representative. RNAscope®-based in situ hybridization assay (ACDbio, Newark, CA) of cynomolgus monkey liver biopsy was performed. Image-based quantitative software analysis (HALO™ software system, Indica Labs, Albuquerque, NM) was utilized to quantify total PNPLA3 mRNA copies in given liver cell populations.

Study 2: A second non-human primate study was performed as described in Study 1, with the follow modifications or additions. Cynos were grouped by body weight (2-5 kg) into two RNAi-treated groups, n=10 per group. Animals were dosed on days 1 and 29 subcutaneously at 4 mg/kg in saline and followed for 57 days.

Results

From Study 1, measurement of PNPLA3 expression by PCR is shown in FIG. 1 for RNAi agent J1D00008. PNPLA3 mRNA was reduced by 51%, 55%, 47%, and 37% at the respective timepoints normalized to baseline and a housekeeping gene. Subsequent to these results, an in situ hybridization (ISH) was performed to evaluate the intracellular (cytoplasmic vs nuclear) distribution of PNPLA3 mRNA. Approximately 50% of the whole cell PNPLA3 mRNA was observed to be partitioned within the nucleus. This suggests that the RNAi agent J1D00008 was significantly reducing PNPLA3 mRNA at the site of protein translation (i.e. the hepatocyte cytoplasm), but that the knockdown at the whole cell-level was underestimated by qPCR due to the confounding residual nuclear PNPLA3 mRNA pool. Cytoplasmic PNPLA3 mRNA knockdown was thus quantified.

ISH performed on liver biopsies from cynos treated with RNAi agent J1D00008 revealed that significant residual PNPLA3 mRNA was retained in the nucleus of cells supporting the assertion that this pool was confounding knockdown results in whole liver as assessed by qPCR.

Quantification of the ISH images showed that, with RNAi agent J1D00008 treatment, PNPLA3 mRNA was reduced in the cytoplasm by 44-63% over all 76 days (Table 30). Since GalNAc-RNAi agents such as RNAi agent J1D00008 mediate degradation of target mRNA specifically in the cytoplasm of hepatocytes, whole liver quantification of PNPLA3 knockdown is diluted by the relative contribution of PNPLA3 mRNA from non-targeted cell types (e.g. stellate and Kupffer cells). Therefore, a model-based analysis was performed to estimate the reduction of PNPLA3 mRNA specifically in the cytoplasm of hepatocytes, with correction for extra-hepatocyte PNPLA3 mRNA expression. Table 31 lists the relevant assumptions to liver physiology employed in the modeling.

TABLE 30

Quantification of ISH images for whole liver cytoplasm and nuclear PNPLA3 expression relative to baseline (day −13) in study #1.

| Time (day) | Nuclear PNPLA3 mRNA (avg. transcript per cell) | Relative expression | Relative knockdown | Cytoplasm PNPLA3 mRNA (avg. transcript per cell) | Relative expression | Relative knockdown |
|---|---|---|---|---|---|---|
| −13 | 0.52 ± 0.21 | n/a | n/a | 0.62 ± 0.27 | n/a | n/a |
| 15 | 0.43 ± 0.15 | 0.84 | 0.16 | 0.20 ± 0.04 | 0.37 | 0.63 |
| 29 | 0.40 ± 0.13 | 0.85 | 0.15 | 0.21 ± 0.05 | 0.38 | 0.62 |
| 57 | 0.53 ± 0.24 | 1.08 | −0.08 | 0.29 ± 0.11 | 0.50 | 0.50 |
| 76 | 0.70 ± 0.28 | 1.45 | −0.45 | 0.33 ± 0.10 | 0.56 | 0.44 |

Data are means relative to baseline ± SD (n = 4)

TABLE 31

Parameters relevant to liver physiology employed in the modeling.

| Cell type | Liver composition (%) |
|---|---|
| Hepatocyte | 85 |
| Stellate cell (HSC) | 8 |
| Kupffer (others . . . ) | 7 |

| Cell type | Relative PNPLA3 mRNA |
|---|---|
| Hepatocyte | 1x |
| Stellate cell (HSC) | 2x |
| Kupffer (others . . . ) | 1x |

Figure 2:
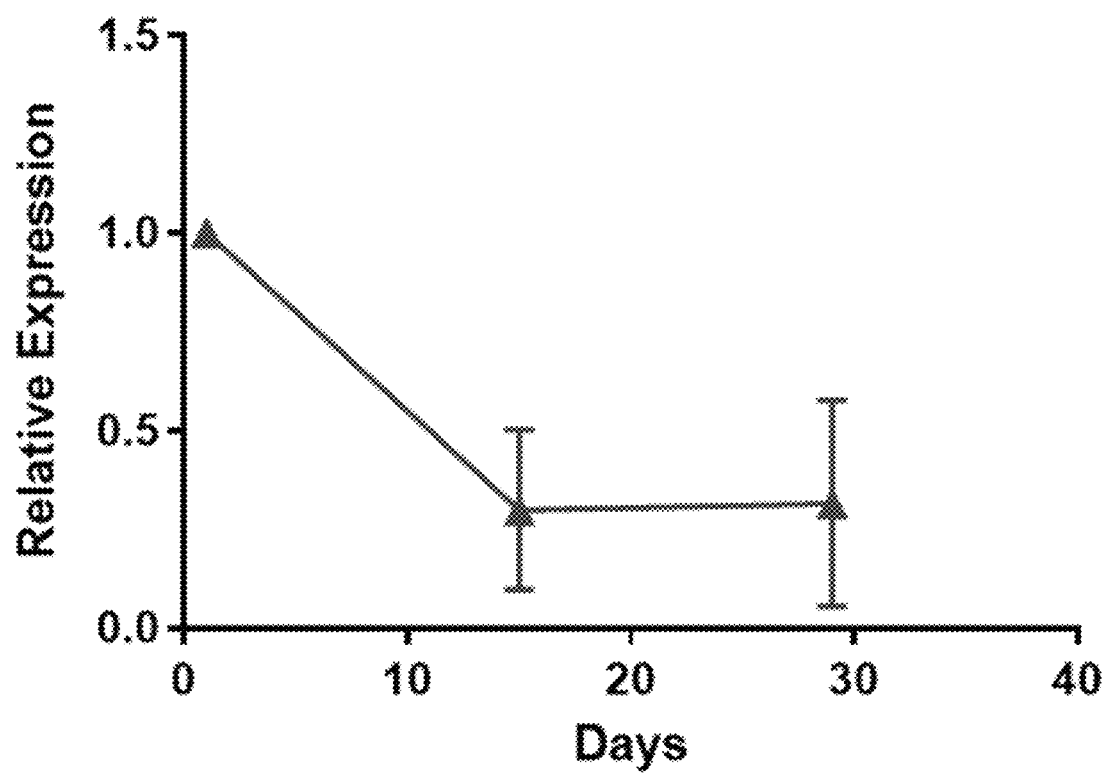
FIG. 2 is a graph depicting the average PNPLA3 mRNA knockdown in the cytoplasm of hepatocytes by quantitative ISH between in all animals tested (study #1 and study #2). Study #2: Data are mean±SD (n=14).

Using this model, PNPLA3 mRNA was reduced by 81% on day 15 and 78% on day 29 in the cytoplasm of hepatocytes after administering a single 4 mg/kg SC dose of RNAi agent J1D00008. When this modeling was repeated in Study 2, a 66% and 65% reduction in PNPLA3 mRNA at days 15 and 29 respectively was achieved. On average across all NHPs tested (n=14) with RNAi agent J1D00008, PNPLA3 mRNA was reduced by 70% in the cytoplasm of hepatocytes on day 15 and day 29 (FIG. 2).

Example 12. Safety

The nonclinical safety of RNAi agent J1D00008 administration for up to 3 months was evaluated in rats and monkeys at doses of up to 500 mg/kg and 300 mg/kg, respectively. In both species, RNAi agent J1D00008 was well tolerated and no adverse signs of toxicity were observed up to the highest doses evaluated.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

The invention claimed is:

1. An RNAi agent for inhibiting expression of a PNPLA3 gene, comprising:
   an antisense strand comprising the nucleotide sequence usUfsasGfuUfaGfgUfgAfaAfaAfgGfuGfsu (SEQ ID NO: 95), wherein nucleotides 1-19 of the antisense strand are complementary to the PNPLA3 mRNA region comprising nucleotides 2180-2198 of SEQ ID NO: 1,
   wherein a, g, and u represent 2'-O-methyl adenosine, 2'-O-methyl guanosine, and 2'-O-methyl uridine, respectively; Af, Gf, and Uf represent 2'-fluoro adenosine, 2'-fluoro guanosine, and 2'-fluoro uridine, respectively; and s represents a phosphorothioate linkage; and
   a sense strand comprising a nucleotide sequence that is at least partially complementary to the antisense strand.

2. The RNAi agent of claim 1, wherein at least one nucleotide of the sense strand of the RNAi agent is a modified nucleotide or includes a modified internucleoside linkage.

3. The RNAi agent of claim 1, wherein all or substantially all of the nucleotides of the sense strand of the RNAi agent are modified nucleotides.

4. The RNAi agent of claim 3, wherein the modified nucleotide is selected from the group consisting of: 2'-O-methyl nucleotide, 2'-fluoro nucleotide, 2'-deoxy nucleotide, 2', 3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate containing nucleotide, cyclopropyl phosphonate containing nucleotide, and 3'-O-methyl nucleotide.

5. The RNAi agent of claim 3, wherein all or substantially all of the modified nucleotides are 2'-O-methyl nucleotides, 2'-fluoro nucleotides, or combinations thereof.

6. The RNAi agent of claim 1, wherein the sense strand comprises the nucleotide sequence acaccuuuUfUfCfaccuaacuaa of SEQ ID NO: 136, wherein a, c, and u represent 2'-O-methyl adenosine, 2'-O-methyl cytidine, and 2'-O-methyl uridine, respectively; and Cf and Uf represent 2'-fluoro cytidine, and 2'-fluoro uridine, respectively.

7. The RNAi agent of claim 1, wherein the RNAi agent is linked to a targeting ligand.

8. The RNAi agent of claim 7, wherein the targeting ligand comprises N-acetyl-galactosamine.

9. The RNAi agent of claim 7, wherein the targeting ligand comprises the structure of (NAG37) or (NAG37)s.

10. The RNAi agent of claim 7, wherein the targeting ligand is linked to the sense strand.

11. The RNAi agent of claim 10, wherein the targeting ligand is linked to the 5' terminal end of the sense strand.

12. The RNAi agent of claim 1, wherein the sense strand is between 18 and 30 nucleotides in length.

13. The RNAi agent of claim 12, wherein the sense strand is between 18 and 27 nucleotides in length.

14. The RNAi agent of claim 13, wherein the sense strand is between 18 and 24 nucleotides in length.

15. The RNAi agent of claim 14, wherein the sense strand is 21 nucleotides in length.

16. The RNAi agent of claim 12, wherein the RNAi agent has two blunt ends.

17. The RNAi agent of claim 1, wherein the sense strand comprises one or two terminal caps.

18. The RNAi agent of claim 1, wherein the sense strand comprises one or two inverted abasic residues.

19. The RNAi agent of claim 1, wherein the RNAi agent is comprised of a sense strand and an antisense strand that form a duplex of SEQ ID NOs: (95 and 136).

20. The RNAi agent of claim 1, wherein the sense strand further includes inverted abasic residues at the 3' terminal end of the nucleotide sequence, at the 5' end of the nucleotide sequence, or at both.

21. The RNAi agent of claim 1, wherein the sense strand comprises a modified nucleotide sequence that differs by 0 or 1 nucleotides from the nucleotide sequence acaccuuuUfUfCfaccuaacuaa of SEQ ID NO: 136;
   wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; and wherein all or substantially all of the nucleotides on the sense strand are modified nucleotides.

22. The RNAi agent of claim 6, wherein the sense strand further includes inverted abasic residues at the 3' terminal end of the nucleotide sequence, at the 5' end of the nucleotide sequence, or at both.

23. The RNAi agent of claim 20, wherein the sense strand of the RNAi agent is linked to a targeting ligand.

24. The RNAi agent of claim 23, wherein the targeting ligand has affinity for the asialoglycoprotein receptor.

25. The RNAi agent of claim 24, wherein the targeting ligand comprises N-acetyl-galactosamine.

26. The RNAi agent of claim 25, wherein the targeting ligand comprises:

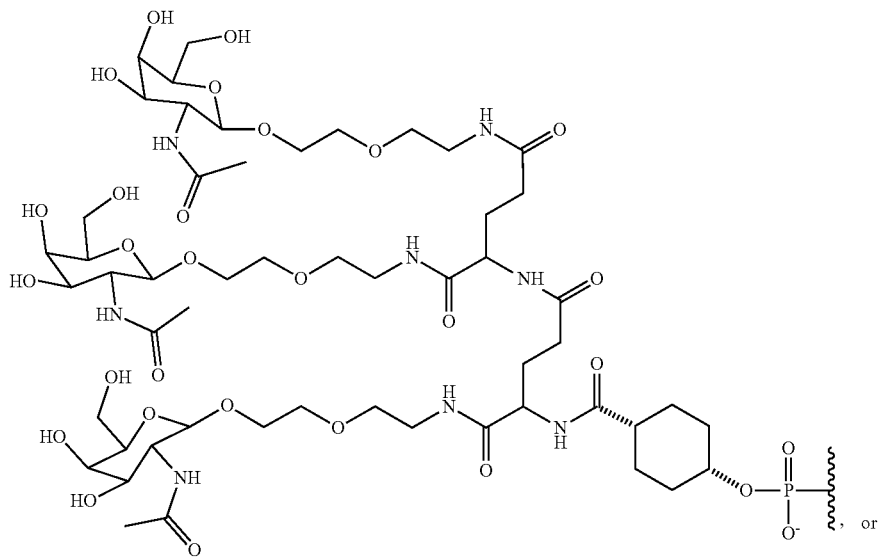

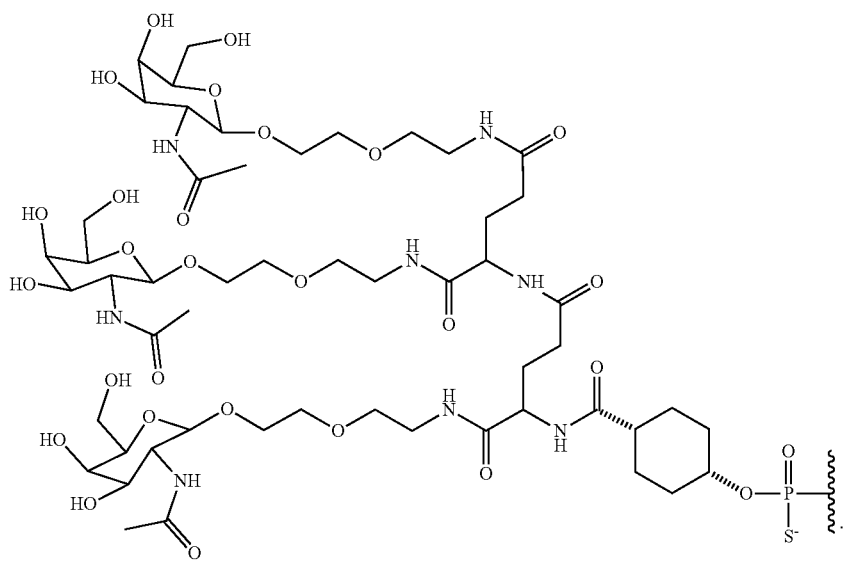

27. The RNAi agent of claim 1, wherein the antisense strand consists of the modified nucleotide sequence usUfsasGfuUfaGfgUfgAfaAfaAfgGfuGfsu (SEQ ID NO: 95), and the sense strand consists of the modified nucleotide sequence (NAG37)s(invAb)sacaccuuuUfUfCfaccuaacuaas (invAb) (SEQ ID NO: 136);

wherein a, c, g, and u are 2'-O-methyl adenosine, 2'-O-methyl cytidine, 2'-O-methyl guanosine, and 2'-O-methyl uridine, respectively; Af, Cf, Gf, and Uf are 2'-fluoro adenosine, 2'-fluoro cytidine, 2'-fluoro guanosine, and 2'-fluoro uridine, respectively; s is a phosphorothioate linkage; (invAb) is an inverted abasic deoxyribose residue; and (NAG37)s has the following chemical structure:

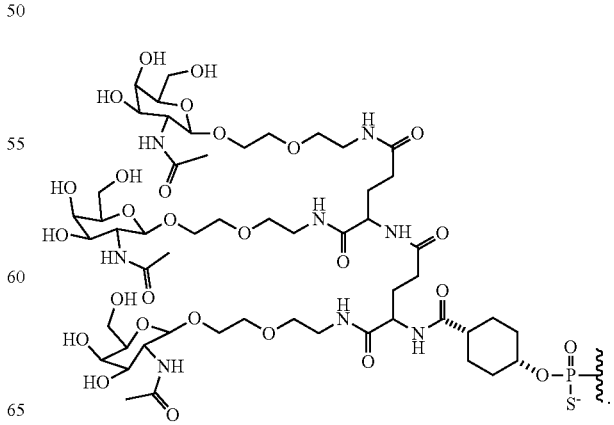

28. A composition comprising the RNAi agent of claim 1, wherein the composition further comprises a pharmaceutically acceptable excipient.

29. A method for inhibiting expression of a PNPLA3 gene in a cell, the method comprising introducing into a cell an effective amount of the RNAi agent of claim 1.

30. The method of claim 29, wherein the cell is within a subject.

31. The method of claim 30, wherein the subject is a human subject.

32. The method of claim 29, wherein the PNPLA3 gene expression is inhibited by at least 30%.

33. The method of claim 29, wherein the cell is within a human subject and the RNAi agent is administered at a dose of 0.05 mg/kg to 5.0 mg/kg of body weight of the human subject.

34. The method of claim 31, wherein the RNAi agent is administered in two or more doses.

* * * * *